United States Patent
Zong et al.

(10) Patent No.: US 12,391,633 B2
(45) Date of Patent: Aug. 19, 2025

(54) METHOD FOR SEPARATING 2-ALKYLANTHRACENES AND USE THEREOF FOR PRODUCING HYDROGEN PEROXIDE

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Baoning Zong, Beijing (CN); Bo Zheng, Beijing (CN); Zhenxing Zhu, Beijing (CN); Zhiyong Pan, Beijing (CN); Siyuan Qie, Beijing (CN); Guohua Gao, Beijing (CN); Jianqi Fei, Beijing (CN); Junyi Mao, Beijing (CN); Xiaojin Tang, Beijing (CN); Lifeng Hu, Beijing (CN); Zheng Liu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 562 days.

(21) Appl. No.: 17/594,434

(22) PCT Filed: Mar. 10, 2020

(86) PCT No.: PCT/CN2020/078563
§ 371 (c)(1),
(2) Date: Oct. 15, 2021

(87) PCT Pub. No.: WO2020/211572
PCT Pub. Date: Oct. 22, 2020

(65) Prior Publication Data
US 2022/0177392 A1 Jun. 9, 2022

(30) Foreign Application Priority Data

Apr. 15, 2019 (CN) .......................... 201910300499.0
Apr. 15, 2019 (CN) .......................... 201910300813.5

(51) Int. Cl.
*C07C 7/00* (2006.01)
*C01B 15/01* (2006.01)
(Continued)

(52) U.S. Cl.
CPC .............. *C07C 7/005* (2013.01); *C01B 15/01* (2013.01); *C01B 15/023* (2013.01); *C07C 2/02* (2013.01);
(Continued)

(58) Field of Classification Search
None
See application file for complete search history.

(56) References Cited

U.S. PATENT DOCUMENTS 3,953,482 A   4/1976   Sugano et al.
4,255,343 A   3/1981   Gosser

FOREIGN PATENT DOCUMENTS

CN     1690035 A      11/2005
CN   106542502 A       3/2017
(Continued)

OTHER PUBLICATIONS

Machine translation of CN109704910A, May 3, 2019; pp. 1-21 (Year: 2019).*

(Continued)

*Primary Examiner* — Medhanit W Bahta
(74) *Attorney, Agent, or Firm* — NKL Law; Allen Xue

(57) ABSTRACT

A method for preparing 2-alkylanthracene includes the step of separating 2-alkylanthracene from a reaction product of anthracene alkylation reaction. The anthracene alkylation reaction is a reaction of anthracene and an alkylation reagent under an alkylation condition and in the presence of an alkylation reaction solvent and a catalyst. The reaction product of the anthracene alkylation reaction contains (Continued)

anthracene and the product of a series of alkylanthracenes containing 2-alkylanthracene.

24 Claims, 4 Drawing Sheets

(51) Int. Cl.
*C01B 15/023* (2006.01)
*C07C 2/02* (2006.01)
*C07C 2/66* (2006.01)
*C07C 2/70* (2006.01)
*C07C 7/04* (2006.01)
*C07C 7/14* (2006.01)
*C07C 15/28* (2006.01)
*C07C 46/04* (2006.01)
*C07C 46/10* (2006.01)

(52) U.S. Cl.
CPC .................. *C07C 2/66* (2013.01); *C07C 2/70* (2013.01); *C07C 7/04* (2013.01); *C07C 7/14* (2013.01); *C07C 15/28* (2013.01); *C07C 46/04* (2013.01); *C07C 46/10* (2013.01); *C07C 2521/04* (2013.01); *C07C 2527/03* (2013.01); *C07C 2529/08* (2013.01); *C07C 2531/025* (2013.01); *C07C 2603/24* (2017.05)

(56) References Cited

FOREIGN PATENT DOCUMENTS

| CN | 106995402 A | 8/2017 |
|---|---|---|
| CN | 107602368 A | 1/2018 |
| CN | 107744828 A | 3/2018 |
| CN | 107746372 A | 3/2018 |
| CN | 109574779 A | 4/2019 |
| CN | 109704910 A | 5/2019 |
| TW | 200623958 A | 7/2006 |
| WO | 03016436 A1 | 2/2003 |
| WO | 2020211572 A1 | 10/2020 |

OTHER PUBLICATIONS

Machine translation of CN107602368A, Ja. 19, 2018; pp. 1-10 (Year: 2018).*

Takeuchi, Tsugio et al.; "Purification method of anthracene by zone melting method and separation crystallization method"; Industrial Chemistry Magazine; vol. 68, No. 3; Year: 1965; pp. 474-476.

Müller, Paul et al. "Rh-catalyzed oxidation of anthracenes to anthraquinones using t-butylhydroperoxide" Tetrahedron Letters, vol. 24, No. 49, Apr. 2, 2001, ISSN: 0040-4039,pp. 5499-5500.

Chen, Min et al. "Alkylation of anthracene to 2-isopropylanthracene catalyzed by Lewis acid ionic liquids" Korean Journal of Chemical Engineering, vol. 26, No. 6, Feb. 16, 2010, ISSN: 0256-1115,pp. 1563-1567.

Wienhöfer, Gerrit et al. "A Novel Process for Selective Ruthenium-Catalyzed Oxidation of Naphthalenes and Phenols", Advanced Synthesis & Catalysis, vol. 352, No. 10, Jun. 30, 2010, ISSN: 1615-4150,pp. 1615-1620.

Gekhman,A. E. et al. "Role of the V(V)/1O2 Complex in Oxidative Reactions in the H2O2/V(V)/AcOH System: Oxidation of Alkenes and Anthracenes", Kinetics and Catalysis, vol. 42, No. 4, Jul. 31, 2001, ISSN: 0023-1584,pp. 496-505.

* cited by examiner

METHOD FOR SEPARATING 2-ALKYLANTHRACENES AND USE THEREOF FOR PRODUCING HYDROGEN PEROXIDE

TECHNICAL FIELD

The invention relates to a separation method of 2-alkylanthracene, in particular to a method for preparing 2-alkylanthraquinone by separating 2-alkylanthracene from the reaction (such as alkylation) of anthracene and then carrying out a catalytic oxidation and a pretreatment method of 2-alkylanthraquinone working fluid.

BACKGROUND TECHNOLOGY

Hydrogen peroxide is an important green basic chemical and has high industrial relevance, China becomes the first major country for the production of hydrogen peroxide since 2008, and the consumption is over 10,000,000 t/a (calculated as 27.5%) in 2015. At present, the technology for producing hydrogen peroxide at home and abroad is mainly an anthraquinone method. The 2-alkylanthraquinone in the technology is used as a "carrier" of the technological process, and the quality and the yield of the hydrogen peroxide are directly influenced.

The phthalic anhydride process is the primary method for producing 2-alkylanthraquinone, but this process has serious pollution problems. 1.76 tons of anhydrous $AlCl_3$ and 4.2 tons of fuming $H_2SO_4$ (20%) are required to be put into the production of 1 ton of 2-ethylanthraquinone, the recovery difficulty of the anhydrous $AlCl_3$ and the fuming $H_2SO_4$ is high, and the post-treatment process is complex.

2-alkylanthraquinone and a mixed solvent (consisting of non-polar solvent and polar solvent) are mixed according to a certain proportion to formulate a working fluid, and the working fluid can be recycled and reused. Hydrogen peroxide can be prepared by the processes of hydrogenation, oxidation, extraction, drying, refining and the like. Since the 2-alkylanthraquinone working fluid contains impurities, it seriously affects the process operation and the product indexes.

Therefore, it is very important to develop a green production process of 2-alkylanthraquinone from the viewpoint of environmental protection and clean production. However, no report has been found about the pretreatment technology of the 2-alkylanthraquinone working fluid, and therefore, a new pretreatment method of the 2-alkylanthraquinone working fluid is also required to be developed.

U.S. Pat. No. 4,255,343 discloses a method for synthesizing 2-tert-pentylanthracene, which comprises the steps of uniformly mixing anthracene, trichlorobenzene and methanesulfonic acid under certain temperature and pressure conditions, and introducing an alkene into a system to perform the alkylation reaction with anthracene. The solid product was mainly the remaining anthracene and the product of a series of alkylanthracenes, wherein anthracene comprises 42 wt % and 2-alkylanthracene comprises 47 wt %, and the remainder comprises disubstituted anthracene products and other by-products. Although this patent provides a process for preparing 2-tert-pentylanthracene by alkylation of anthracene, it does not provide a process for separating 2-alkylanthracene from a complex product system, shifts off the most critical separation problem of the alkylanthracene system with higher boiling/solidifying points, and further fails to provide a subsequent application of 2-alkylanthracene.

TW200623958 discloses a method for catalyzing anthracene alkylation by using ionic liquid, and the catalytic system of the alkylation reaction is a mixture containing 60-93.7 wt % of ionic liquid and 1-8 wt % of aluminum chloride. In the examples, $BmimPF_6$ is used as a solvent, a proper amount of $AlCl_3$ is added to catalyze the alkylation reaction of anthracene and tert-butyl chloride at 70° C., and the yield of the product 2, 6-tert-butyl anthracene is 90%.

Perezromero et al proposed the preparation of the corresponding anthraquinones by oxidizing anthracene or 2-alkylanthracene with $H_2O_2$, the catalyst is Cu-containing TpxCu(NCMe), and the reaction at 80° C. for 2 hours gives the anthracene conversion of 95% and the anthraquinone selectivity of 98%.

U.S. Pat. No. 3,953,482 discloses a process for preparing 2-alkylanthraquinone by oxidizing 2-alkylanthracene with $H_2O_2$. Fatty alcohol is used as solvent, concentrated hydrochloric acid is used as catalyst, $H_2O_2$ (60%) is used as oxidizing agent, and the reaction is performed for 60 min at 40-100° C. under normal pressure. A better reaction effect can be obtained. The conversion of 2-pentylanthracene is 94%, and the selectivity of 2-pentylanthraquinone is as high as 97%. However, the patent uses concentrated hydrochloric acid as catalyst, which is severely corrosive, and the chlorine-containing wastewater generated after the reaction cannot be treated, which brings pressure to environmental protection. In addition, the use of concentrated hydrochloric acid tends to result in chlorination of the anthracene ring, resulting in the formation of alkylanthracene chloride products which are difficult to be separated, resulting in higher chlorine content of the product. The patent proposes an oxidation method of 2-alkylanthracene, but 2-alkylanthracene cannot be separated from the existing resources in the nature and can only be prepared independently. This patent also does not provide an efficient method for obtaining 2-alkylanthracenes, which in turn limits the application of the patent.

As a result, no report is available on a full set of process technology for preparing 2-alkylanthraquinone by using anthracene as feedstock. In addition, the inventor of the present invention found that in the hydrogenation process for preparing hydrogen peroxide by using the 2-alkylanthraquinone working fluid, a noble metal palladium catalyst is generally used, and in the catalytic hydrogenation process in form of fixed bed, the activity and stability of the catalyst is good because the loading amount of palladium in the catalyst is relatively high. However, in the case of catalytic hydrogenation in form of slurry bed or fluidized bed, the loading amount of palladium in the used fine powder catalyst can be significantly reduced, but the catalyst is easily chemically deactivated, and the continuous stability of the production process and the quality of the product cannot be guaranteed. The inventor of the present invention finds out through research that, due to the influence of the sources and the purity of the alkylanthraquinone product and the mixed solvent, the sulfur content of the finally prepared 2-alkylanthraquinone working fluid is about 1-6 mg/kg. These sulfides can lead to the deactivation of the noble metal palladium catalyst in the hydrogenation process of the working fluid and therefore the reduction of the service life of the catalyst, not only increasing the use cost, but also seriously affecting the process efficiency. Therefore, in order to improve the efficiency of the whole process and purify the reaction environment, the 2-alkylanthraquinone working fluid needs to be pretreated for desulfurization and impurity removal.

At present, liquid-phase desulfurization technologies can be divided into hydrodesulfurization technologies and non-hydrodesulfurization technologies, and the hydrodesulfurization technologies are not suitable for the desulfurization treatment process of the 2-alkylanthraquinone working fluid because hydrogen can react with 2-alkylanthraquinone. Non-hydrodesulfurization technologies include oxidative desulfurization, extractive desulfurization, alkylation desulfurization, and adsorption desulfurization and the like. The adsorption desulfurization technology has the advantages of simple operation, mild conditions, small equipment investment, good desulfurization effect, no impurity introduction and the like, and is particularly suitable for the desulfurization process of the 2-alkylanthraquinone working fluid.

Before the research of the present inventors, there is no report on the adsorption desulfurization of 2-alkylanthraquinone working fluid in the prior art. Therefore, no report is made on the use of amorphous alloy as adsorbent for 2-alkylanthraquinone working fluids. Although amorphous alloys have been reported for adsorptive removal of sulfides from fuel oils, however the process and condition of the adsorption requires preventing the adsorption desulfurization processes from contacting with water.

SUMMARY OF THE INVENTION

The purpose of the present invention is to provide a new method for preparing 2-alkylanthraquinone by catalytic oxidation of 2-alkylanthracene separated from the reaction of anthracene on the basis of the prior art, namely an integrated process including the preparation of a reaction product containing alkylanthracene from the reaction of anthracene as feedstock, the separation of the reaction product to produce 2-alkylanthracene, and the oxidation reaction of 2-alkylanthracene to produce 2-alkylanthraquinone.

In addition, the present invention also aims to provide a novel pretreatment method of the 2-alkylanthraquinone working fluid, which can obviously reduce the impurity content and the sulfur content of the working fluid.

Furthermore, the purpose of the present invention is to provide a new method for preparing 2-alkylanthraquinone by catalytic oxidation of 2-alkylanthracene obtained from the alkylation of anthracene, and preparing hydrogen peroxide with 2-alkylanthraquinone on the basis of the prior art, namely an integrated process including the preparation of 2-alkylanthracene through the alkylation reaction of anthracene as feedstock and the separation, the preparation of 2-alkylanthraquinone through the oxidation reaction of 2-alkylanthracene, and the preparation of hydrogen peroxide with 2-alkylanthraquinone.

In one aspect, the present invention provides a method for preparing 2-alkylanthraquinone by catalytic oxidation of 2-alkylanthracene obtained by alkylation of anthracene, which is characterized in that said preparation method comprises the following steps:
(1) contacting anthracene and an alkylation reagent under an alkylation condition and in the presence of an alkylation reaction solvent and a catalyst to perform the alkylation reaction to produce a reaction product containing alkylanthracenes, the alkylation reaction solvent is a combination of solvent A having a dielectric constant of 1-10 at 20° C. and solvent B having a dielectric constant of more than 10 to 50 or less at 20° C.;
(2) separating the reaction product containing alkylanthracenes obtained from step (1), the separation method comprising: the separation of anthracene by melting crystallization and the separation of 2-alkylanthracene by distillation;
(3) contacting 2-alkylanthracene obtained from step (2) with an oxidizing agent under an oxidizing condition and in the presence of an oxidation reaction solvent and a catalyst to perform an oxidation reaction, the oxidizing agent is hydrogen peroxide, the catalyst is one or more of alkaline earth metal oxide, alkaline earth metal hydroxide, oxygen-containing compound of transition metal and oxygen-containing compound of lanthanide series metal.

In this respect, the whole technical route for preparing 2-alkylanthraquinone by catalytic oxidation of 2-alkylanthracene obtained by alkylation of anthracene provided by the present invention is reasonable and feasible, and opens up a new direction for green preparation of 2-alkylanthraquinone. In the method provided by the present invention, the combined solvent is adopted as a reaction medium in the alkylation reaction process, so that the properties of the reaction solvent can be effectively regulated and controlled, the solvation effect is exerted, the solubility of anthracene is improved, and the alkylation reaction is promoted. In the method provided by the present invention, the operation difficulty in the process of separating the anthracene-alkylanthracene product can be remarkably reduced by the melting crystallization-distillation coupling separation technology, and the purity and the total yield of the intermediate target product 2-alkylanthracene are improved.

In the method provided by the present invention, the constructed 2-alkylanthracene catalytic oxidation system is simple and efficient, the difficulty in separating and recovering the catalyst is low, and no corrosivity exists, the equipment investment and the post-treatment cost of the oxidation waste liquor are reduced, and the conversion of 2-alkylanthracene can be effectively realized. Preferably, in the method provided by the present invention, a combined solvent system is used in the reaction process for preparing anthraquinone by the oxidization of 2-alkylanthracene, so that the oxidation reaction of the 2-alkylanthracene can be intensified by adjusting the properties of the solvent, and the reaction selectivity and the product yield can be improved. In addition, the method provided by the present invention also has the advantages of simple process, high efficiency and small pollution.

In an one aspect, the present invention provides a method for preparing 2-alkylanthraquinone by catalytic oxidation of 2-alkylanthracene obtained by separation from the reaction of anthracene, which is characterized in that said preparation method comprises the following steps:
(1) preparing a reaction product containing alkylanthracenes from anthracene;
(2) separating the reaction product containing alkylanthracenes obtained from step (1), the separation method comprising: the separation of anthracene by melting crystallization and the separation of 2-alkylanthracene by distillation;
(3) contacting 2-alkylanthracene obtained in step (2) with an oxidizing agent under an oxidizing condition and in the presence of an oxidation reaction solvent and a catalyst to perform the oxidation reaction, the oxidizing agent is tert-butyl hydroperoxide, the catalyst contains a support and an active component on the support, the active component is one or more of elements under the group VA and transition metals.

In this respect, the whole technical route for preparing 2-alkylanthraquinone by catalytic oxidation of 2-alkylanthracene obtained by separation from the reaction of anthracene provided by the present invention is reasonable and feasible, and opens up a new direction for green preparation of 2-alkylanthraquinone. In the method provided by the present invention, the operation difficulty in the process of separating the anthracene-alkylanthracene product can be remarkably reduced by the melting crystallization-distillation coupling separation technology, and the purity and the total yield of the intermediate target product 2-alkylanthracene are improved. In the method provided by the invention, the constructed 2-alkylanthracene oxidation system has high feedstock conversion, good selectivity, low difficulty in separating and recovering the catalyst, no stream corrosivity and reduced equipment investment. In addition, the method provided by the present invention also has the advantages of simple process, high efficiency and small pollution.

In another aspect, the present invention provides a method for pretreating a 2-alkylanthraquinone working fluid, which is characterized in that the method comprises: contacting the 2-alkylanthraquinone working fluid with an adsorbent in alkali liquor to perform an adsorption desulfurization and impurity removal; separating the 2-alkylanthraquinone working fluid that has been subjected to the adsorption desulfurization and impurity removal; and washing, the adsorbent is an amorphous alloy, and the amorphous alloy contains nickel.

Preferably, the amorphous alloy further contains one or more metals of aluminum, iron, chromium, copper, zinc, molybdenum and cobalt.

Preferably, based on the total weight of amorphous alloy, the content of nickel is 35-95 wt %, the total content of other metals is 5-65 wt %, more preferably, based on the total weight of amorphous alloy, the content of nickel is 50-90 wt %, the total content of other metals is 10-50 wt %.

Preferably, the amorphous alloy contains nickel and aluminum, and one or more metals of iron, chromium, copper, zinc, molybdenum and cobalt, more preferably at least one of a combination of chromium and iron, a combination of chromium and copper, a combination of chromium and molybdenum, a combination of chromium and cobalt; based on the total weight of amorphous alloy, the content of nickel is 35-95 wt %, the content of aluminum is 0.5-40 wt %, the total content of one or more metals of iron, chromium, copper, zinc, molybdenum and cobalt is 0.1-50 wt %, more preferably, based on the total weight of amorphous alloy, the content of nickel is 50-90 wt %, the content of aluminum is 1-30 wt %, the total content of one or more metals of iron, chromium, copper, zinc, molybdenum and cobalt is 1-40 wt %, further preferably, based on the total weight of amorphous alloy, the content of nickel is 50-90 wt %, the content of aluminum is 1-15 wt %, the total content of one or more metals of iron, chromium, copper, zinc, molybdenum and cobalt is 5-40 wt %.

Preferably, the condition for contacting the 2-alkylanthraquinone working fluid with the adsorbent in alkali liquor includes: the temperature is 10-200° C., more preferably 25-170° C., the pressure is 0-3 MPa, more preferably 0-2 MPa; more preferably, the number of contact is 1-5, more preferably 2-4, the time for each contact is 0.01-24 hours, preferably 0.5-8 hours; further preferably, the contact is performed under stirring, the rotation speed of the stirring is 500-2000 rpm, more preferably 800-1200 rpm.

Furthermore, the present invention also provides a method for producing hydrogen peroxide, which comprises the steps of hydrogenating, oxidizing and extracting a 2-alkylanthraquinone working fluid, and is characterized in that the method also comprises a step of pretreating a fresh-formulated 2-alkylanthraquinone working fluid, said pretreating is the method for pretreating a 2-alkylanthraquinone working fluid provided by the present invention.

The pretreatment method of the 2-alkylanthraquinone working fluid provided by the present invention is to perform the adsorption desulfurization and impurity removal by contacting the 2-alkylanthraquinone working fluid with the adsorbent in alkali liquor, i.e. the working fluid, the alkali liquor and the adsorbent are simultaneously contacted to perform the washing with alkali liquor and the adsorption desulfurization, wherein the adsorbent is a nickel-based amorphous alloy. Because the nickel-based amorphous alloy shows excellent stability in the alkali liquor and has good desulfurization activity, the present invention creatively provides the coupling of the alkali washing and the adsorption desulfurization of the 2-alkylanthraquinone working fluid, so that the pretreatment process flow can be shortened, the process efficiency can be improved, and the effects of removing impurities and reducing the sulfur content can become better, thereby effectively solving the problem of poisoning and inactivation of the noble metal-palladium catalyst in the hydrogenation process when the 2-alkylanthraquinone working fluid is used to prepare hydrogen peroxide, and having good industrial application prospect.

The present invention also provides a series of technical solutions in the group D, as follows:

1. A method of preparing a 2-alkylanthracene, wherein the method comprises the steps of:
    Separating 2-alkylanthracene from the reaction product of an anthracene alkylation reaction, said anthracene alkylation reaction is a reaction of anthracene with an alkylation reagent under an alkylation condition and in the presence of an alkylation reaction solvent and a catalyst;
    Wherein the reaction product of the anthracene alkylation reaction contains anthracene and a product of a series of alkylanthracenes containing 2-alkylanthracene;
    Preferably, the alkyl is one or more, preferably one of $C_4$-$C_7$ alkyl, for example $C_4$-$C_6$ alkyl, particularly preferably, the alkyl is selected from linear or branched butyl, linear or branched pentyl, linear or branched hexyl, and linear or branched heptyl, most preferably, the alkyl is one of linear or branched butyl, linear or branched pentyl, linear or branched hexyl, and linear or branched heptyl.

2. The method of technical solution D1, wherein the separation includes: the separation of anthracene by melting crystallization and the separation of 2-alkylanthracene by distillation.

3. The method according to any of the preceding technical solutions D1-D2, wherein the separation includes:
    (a) heating the reaction product of the anthracene alkylation reaction to a molten state, cooling and crystallizing, separating to obtain an anthracene crystal and a stream of the product of a series of alkylanthracenes containing 2-alkylanthracene, heating the anthracene crystal to sweat, and separating the sweating liquor and the anthracene crystal;
    (b) separating 2-alkylanthracene from the product of a series of alkylanthracenes containing 2-alkylanthracene by one-step distillation or multiple-step distillation.

4. The method according to the preceding technical solution D3, wherein
    In step (a),
    The melting temperature is 200-270° C., preferably 210-250° C.;
    The temperature for cooling and crystallizing is 180-210° C., the temperature reduction rate for cooling and crystallizing is 0.1-10° C./hour, the time for cooling and crystallizing is 1-5 hours; preferably, the temperature for cooling and crystallizing is 190-200° C., the temperature reduction rate for cooling and crystallizing is 0.5-5° C./hour, the time for cooling and crystallizing is 1.5-4 hours.

The temperature-rise rate for sweating the anthracene crystal is 0.1-8° C./hour, preferably 0.2-4° C./hour;

The temperature to which the temperature is increased and at which the sweating is terminated is lower than the melting temperature of the anthracene crystal, preferably the temperature to which the temperature is increased and at which the sweating is terminated is lower than or equal to 210° C., more preferably, the temperature is increased to a temperature 5-15° C. higher than the temperature for cooling and crystallizing, and the sweating is terminated when the temperature is below 210° C.; further preferably, the temperature at which the sweating is terminated is 190-210° C., most preferably 195-205° C.;

The sweating amount is 5-40%, preferably 10-30% by weight of the anthracene crystal.

5. The method according to any of the preceding technical solutions D3-D4, wherein In the step (a), in the cooling and crystallization, a step of adding anthracene as crystal seeds in an amount of 0.1-10 wt %, preferably 0.2-5 wt %, based on the mass of the molten mixture, is further included.

6. The method according to any of the preceding technical solutions D3-D5, wherein Recycling the sweating liquor back to the step of melting crystallization, and carrying out the melting crystallization together with the reaction product containing alkylanthracene.

7. The method according to the preceding technical solution D3, wherein

In step (b), if the product of a series of alkylanthracenes containing 2-alkylanthracene is a mixture of two substances, or a mixture of three or more substances, and the boiling point of 2-alkylanthracene is the lowest or the highest; then a one-step distillation separation of the 2-alkylanthracene is performed.

8. The method according to the preceding technical solution D3, wherein

In step (b), if the product of a series of alkylanthracenes containing 2-alkylanthracene is a mixture of three or more substances, and the boiling point of the 2-alkylanthracene is between the boiling points of a substance with the highest boiling point and a substance with the lowest boiling point in the mixture; then a multiple-step distillation is performed, wherein the multiple-step distillation comprises:

Mode 1:

A stream of the product of a series of alkylanthracenes containing 2-alkylanthracene is subjected to a first distillation separation to produce a distillate containing light component Cj1-anthracene and a bottom product containing heavy component Cj2-anthracene; the distillate containing light component Cj1-anthracene is subjected to a second distillation to produce a distillate containing light component Cj3-anthracene and a bottom product containing target product Ci-anthracene;

Wherein the light component Cj1-anthracene is a mixture of a plurality of alkylanthracenes, and for each alkylanthracene, the total carbon number j1 of alkyl side chain is $1<j1<i+1$; the heavy component Cj2-anthracene is one alkylanthracene or a mixture of a plurality of alkylanthracenes, and for each alkylanthracene, the total carbon number j2 of alkyl side chain is $i<j2<41$; the light component Cj3-anthracene is one alkylanthracene or a mixture of a plurality of alkylanthracenes, and for each alkylanthracene, the total carbon number j3 of alkyl side chain is $1<j3<i$;

or,

Mode 2:

A stream of the product of a series of alkylanthracenes containing 2-alkylanthracene is subjected to a third distillation to produce a distillate containing light component Cm1-anthracene and a bottom product containing heavy component Cm2-anthracene; the bottom product containing heavy component Cm2-anthracene is subjected to a fourth distillation to produce a distillate containing target product Ci-anthracene and a bottom product containing heavy component Cm3-anthracene;

Wherein the light component Cm1-anthracene is an alkylanthracene or a mixture of a plurality of alkylanthracenes, and for each alkylanthracene, the total carbon number m1 of alkyl side chain is $1<m1<i$;

Wherein the heavy component Cm2-anthracene is a mixture of a plurality of alkylanthracenes, and for each alkylanthracene, the total carbon number m2 of alkyl side chain is $i-1<m2<41$;

Wherein the heavy component Cm3-anthracene is one alkylanthracene or a mixture of a plurality of alkylanthracenes, and for each alkylanthracene, the total carbon number m3 of alkyl side chain is $i<m3<41$;

Wherein j1, j2, j3, m1, m2 and m3 are integers, i in the target product Ci-anthracene represents the total carbon number of alkyl side chain, and i=an integer of 4-7.

9. The method according to the preceding technical solution D8, wherein

The condition of the first vacuum distillation includes:

The top pressure of the distillation column is 0.01-20 KPa (absolute pressure), the temperature at the column bottom is 180-360° C., the theoretical plate number is 20-90, the top reflux ratio is 0.5-8;

More preferably, the top pressure of the distillation column is 0.1-10 KPa (absolute pressure), the temperature at the column bottom is 210-340° C., the theoretical plate number is 30-75, the top reflux ratio is 1-7;

further preferably, the top pressure of the distillation column is 0.5-2 KPa (absolute pressure), the temperature at the column bottom is 220-320° C., the theoretical plate number is 40-75, the top reflux ratio is 1-3;

yet further preferably, the top pressure of the distillation column is 0.5-2 KPa (absolute pressure), the temperature at the column bottom is 260-320° C., the theoretical plate number is 40-75, the top reflux ratio is 1-3;

the condition of the second vacuum distillation includes:

the top pressure of the distillation column is 0.01-20 KPa (absolute pressure), the temperature at the column bottom is 180-330° C., the theoretical plate number is 20-90, the top reflux ratio is 0.5-8;

more preferably, the top pressure of the distillation column is 0.1-10 KPa (absolute pressure), the temperature at the column bottom is 200-310° C., the theoretical plate number is 30-75, the top reflux ratio is 1-7;

further preferably, the top pressure of the distillation column is 0.5-2 KPa (absolute pressure), the temperature at the column bottom is 220-305° C., the theoretical plate number is 40-75, the top reflux ratio is 1-5;

yet further preferably, the top pressure of the distillation column is 0.5-2 KPa (absolute pressure), the temperature at the column bottom is 220-300° C., the theoretical plate number is 40-75, the top reflux ratio is 1-5;

the condition of the third vacuum distillation includes:
the top pressure of the distillation column is 0.01-20 KPa (absolute pressure), the temperature at the column bottom is 180-360° C., the theoretical plate number is 20-90, the top reflux ratio is 0.5-8;
more preferably, the top pressure of the distillation column is 0.1-10 KPa (absolute pressure), the temperature at the column bottom is 210-340° C., the theoretical plate number is 30-75, the top reflux ratio is 1-7;
further preferably, the top pressure of the distillation column is 0.5-2 KPa (absolute pressure), the temperature at the column bottom is 220-320° C., the theoretical plate number is 40-75, the top reflux ratio is 1-3;
yet further preferably, the top pressure of the distillation column is 0.5-2 KPa (absolute pressure), the temperature at the column bottom is 260-320° C., the theoretical plate number is 40-75, the top reflux ratio is 1-3;
the condition of the fourth vacuum distillation includes:
the top pressure of the distillation column is 0.01-20 KPa (absolute pressure), the temperature at the column bottom is 180-330° C., the theoretical plate number is 20-90, the top reflux ratio is 0.5-8;
more preferably, the top pressure of the distillation column is 0.1-10 KPa (absolute pressure), the temperature at the column bottom is 200-310° C., the theoretical plate number is 30-75, the top reflux ratio is 1-7;
further preferably, the top pressure of the distillation column is 0.5-2 KPa (absolute pressure), the temperature at the column bottom is 220-305° C., the theoretical plate number is 40-75, the top reflux ratio is 1-5;
yet further preferably, the top pressure of the distillation column is 0.5-2 KPa (absolute pressure), the temperature at the column bottom is 220-300° C., the theoretical plate number is 40-75, the top reflux ratio is 1-5.

10. The method according to any of the preceding technical solutions D1 to D9, wherein
The reaction product further contains an alkylation reaction solvent;
The method further comprises a step of separating the alkylation reaction solvent before the separation of anthracene by melting crystallization and the separation of 2-alkylanthracene by distillation;
The separation of alkylation reaction solvent comprises the reaction product of the anthracene alkylation reaction is subjected to distillation in a distillation column to produce a distillate containing alkylation reaction solvent, and a bottom product containing anthracene and the product of a series of alkylanthracenes containing 2-alkylanthracene;
The preferred condition for distillation includes: the temperature at the bottom of distillation column is 100-300° C., preferably 150-200° C., the top pressure of the distillation column is normal pressure.

11. The method according to any of the preceding technical solutions D1-D10, wherein
The alkylation reagent is one or more of alkene, alcohol, halohydrocarbon and ether substances containing 2-8 carbon atoms, preferably one or more of alkene, alcohol, halohydrocarbon and ether substances containing 4-7, for example 4-6 carbon atoms, more preferably mono-olefin containing 4-7, for example 4-6 carbon atoms;
The mole ratio of anthracene to alkylation reagent is 0.2:1-20:1, preferably 0.5:1-5:1.

12. The method according to any of the preceding technical solutions D1-D11, wherein
Contacting a feedstock liquor containing anthracene, catalyst and alkylation reaction solvent with an alkylation reagent to perform the alkylation reaction;
Preferably, the alkylation reaction condition includes: the reaction temperature is 100-250° C., preferably 120-200° C.; the reaction pressure is 0-1 MPa (gauge pressure), preferably 0.05-0.5 MPa (gauge pressure); the reaction time is 0.01-48 hours, preferably 0.5-24 hours.

13. The method according to any of the preceding technical solutions D1-D12, wherein
The alkylation reaction solvent is a combination of solvent A having a dielectric constant of 1-10 at 20° C. and solvent B having a dielectric constant of more than 10 to 50 or less at 20° C.;
Preferably, the solvent A is one or more of $C_6$ or more, preferably $C_6$-$C_{12}$ alkane, cycloalkane and aromatic hydrocarbon, wherein the aromatic hydrocarbon is substituted or unsubstituted, preferably one or more of mono- or poly-substituted benzenes, more preferably one or more of poly-substituted benzenes, the substituent is one or more of $C_1$-$C_4$ alkyl and halogen, the solvent B is N-alkyl substituted amide, wherein the number of alkyl substituent is 1-2, and each alkyl substituent is independently $C_1$-$C_4$ alkyl;
More preferably, the solvent A is one or more of polyalkyl substituted benzenes, the solvent B is one or more of N,N-dimethylformamide, N,N-dimethylacetamide and N,N-dimethylpropionamide;
Most preferably, the solvent A is one or more of 1,3,5-trimethylbenzene, 1,2,3,5-tetramethylbenzene, 1,2,3,4-tetramethylbenzene and 2,3,5,6-tetramethylbenzene, the solvent B is N,N-dimethylformamide;
The volume ratio of the solvent A to the solvent B is 0.01-100, preferably 0.1-10;
Based on the total weight of anthracene and alkylation reaction solvent, the content of anthracene is 5-60 wt %, preferably 8-50 wt %;
The catalyst is a solid acid catalyst, the solid acid catalyst contains an active molecular sieve and a binder, based on the total weight of the solid acid catalyst, the content of active molecular sieve is 30-95 wt %, the content of binder is 5-70 wt %, the active molecular sieve is one or more of X zeolite, Y zeolite, beta zeolite, ZSM-5 zeolite, SAPO zeolite and mesoporous zeolite, preferably Y zeolite; the binder is an inorganic binder, the inorganic binder is a thermotolerant inorganic oxide and/or silicate, preferably alumina;
Based on the total weight of the feedstock liquor containing anthracene, catalyst and alkylation reaction solvent, the content of catalyst is 0.01-50 wt %, preferably 0.5-30 wt %.

14. The method according to any of the preceding technical solutions D1-D12, wherein
The alkylation reaction solvent is a solvent having a dielectric constant of 1-10 at 20° C.;
Preferably, the alkylation reaction solvent is one or more of $C_6$ or more, preferably $C_6$-$C_{12}$ alkane, cycloalkane and aromatic hydrocarbon, wherein the aromatic hydrocarbon is substituted or unsubstituted, preferably one or more of mono- or poly-substituted benzenes, more preferably one or more of poly-substituted benzenes, the substituent is one or more of $C_1$-$C_4$ alkyl and halogen;
More preferably, the alkylation reaction solvent is one or more of polyalkyl substituted benzenes;

Most preferably, the alkylation reaction solvent is one or more of 1,3,5-trimethylbenzene, 1,2,3,5-tetramethylbenzene, 1,2,3,4-tetramethylbenzene and 2,3,5,6-tetramethylbenzene;

Based on the total weight of anthracene and alkylation reaction solvent, the content of anthracene is 5-60 wt %, preferably 8-50 wt %;

The catalyst is one or more of liquid acids, preferably methanesulfonic acid and/or paratoluenesulfonic acid;

Based on the total weight of the feedstock liquor containing anthracene, catalyst and alkylation reaction solvent, the content of catalyst is 0.01-50 wt %, preferably 0.5-30 wt %.

15. Use of the method according to any of the preceding technical solutions D1-D14 for the preparation of 2-alkylanthraquinone by catalytic oxidation of 2-alkylanthracene and for the preparation of hydrogen peroxide using 2-alkylanthraquinone, wherein the preparation of 2-alkylanthraquinone by catalytic oxidation comprises the steps of:

Contacting 2-alkylanthracene obtained by separation with an oxidizing agent under an oxidizing condition and in the presence of an oxidation reaction solvent and a catalyst to perform an oxidation reaction, preferably the contacting manner is to contact a feedstock liquor containing 2-alkylanthracene, a catalyst and an oxidation reaction solvent with an oxidizing agent to perform the oxidation reaction;

wherein

The oxidizing agent is hydrogen peroxide, preferably the hydrogen peroxide is used in the form of an aqueous hydrogen peroxide solution;

The catalyst is one or more of alkaline earth metal oxide, alkaline earth metal hydroxide, oxygen-containing compound of transition metal and oxygen-containing compound of lanthanide series metal;

Preferably, the catalyst is one or more of oxygen-containing compounds of group IIA, group IVB, group VB, group VIB, group VIIB, group VIII metals and lanthanide series metal;

More preferably, the catalyst is one or more of oxygen-containing compounds of Ca, Ba, Ti, Zr, V, Cr, Mo, W, Mn, Ru, Co, Ni, La and Ce;

Most preferably, the catalyst is one or more of calcium hydroxide, barium hydroxide, metatitanic acid, zirconium dioxide, zirconyl nitrate, sodium metavanadate, potassium chromate, chromium sesquioxide, sodium molybdate, ammonium molybdate, molybdenum trioxide, sodium tungstate, manganese sesquioxide, manganese dioxide, ruthenium dioxide, cobaltic oxide, nickel oxide, nickel sesquioxide, lanthanum nitrate, lanthanum sesquioxide, and cerium dioxide;

The condition of oxidation reaction includes: the reaction temperature is 10-200° C., preferably 20-120° C.; the reaction pressure is 0-1 MPa (gauge pressure), preferably 0-0.5 MPa (gauge pressure); the reaction time is 0.01-48 hours, preferably 0.5-24 hours;

The mole ratio of the oxidizing agent to 2-alkylanthracene is 0.01:1-100:1, preferably 1:1-50:1;

The mole ratio of the oxidizing agent to the catalyst is 0.01:1-100:1, preferably 0.1:1-30:1;

16. The use according to the preceding technical solution D15, wherein

The solvent for the oxidation reaction is a solvent with a dielectric constant of more than 2.8 at 20° C., Preferably, the oxidation reaction solvent is a solvent having a dielectric constant of greater than 2.8 to less than or equal to 50 at 20° C., More preferably, the oxidation reaction solvent is one or more of fatty alcohol with carbon number of 1-4, tetrahydrofuran, acetone, N-alkyl substituted amide and N-alkyl pyrrolidone; wherein the number of the alkyl substituent is 1-2, and each alkyl substituent is independently $C_1$-$C_4$ alkyl;

Most preferably, the oxidation reaction solvent is one or more of methanol, tert-butyl alcohol, acetone, N,N-dimethylformamide, N,N-dimethylacetamide, N,N-dimethylpropionamide, N-methylpyrrolidone and N-ethylpyrrolidone;

Based on the total weight of 2-alkylanthracene and the oxidation reaction solvent, the total content of 2-alkylanthracene is 0.1-80 wt %, preferably 5-50 wt %.

17. The use according to the preceding technical solution D15, wherein

The oxidation reaction solvent is:

(1) solvent A having a dielectric constant of 1-10 at 20° C., or (2) a combination of solvent A having a dielectric constant of 1-10 at 20° C. and solvent B having a dielectric constant of more than 10 to 50 or less at 20° C., preferably, the volume ratio of solvent A to solvent B is 0.01-100, preferably 0.05-10;

Preferably, the solvent A is one or more of $C_6$ or more, preferably $C_6$-$C_{12}$ alkane, cycloalkane and aromatic hydrocarbon, wherein the aromatic hydrocarbon is substituted or unsubstituted, preferably one or more of mono- or poly-substituted benzenes, more preferably one or more of poly-substituted benzenes, the substituent is one or more of $C_1$-$C_4$ alkyl and halogen, the solvent B is N-alkyl substituted amide, wherein the number of the alkyl substituent is 1-2, and each alkyl substituent is independently $C_1$-$C_4$ alkyl;

More preferably, the solvent A is one or more of polyalkyl substituted benzenes, the solvent B is one or more of N,N-dimethylformamide, N,N-dimethylacetamide and N,N-dimethylpropionamide;

Most preferably, the solvent A is one or more of 1,3,5-trimethylbenzene, 1,2,3,5-tetramethylbenzene, 1,2,3,4-tetramethylbenzene and 2,3,5,6-tetramethylbenzene, the solvent B is N,N-dimethylformamide;

Wherein, based on the total weight of 2-alkylanthracene and the oxidation reaction solvent, the total content of 2-alkylanthracene is 0.1-80 wt %, preferably 5-50 wt %.

18. Use of the method according to any of the preceding technical solutions D1-D14 for the preparation of 2-alkylanthraquinone by catalytic oxidation of 2-alkylanthracene and for the preparation of hydrogen peroxide using 2-alkylanthraquinone, wherein the preparation of 2-alkylanthraquinone by catalytic oxidation comprises the steps of:

Contacting 2-alkylanthracene obtained by separation with an oxidizing agent under an oxidizing condition and in the presence of an oxidation reaction solvent and a catalyst to perform an oxidation reaction, preferably the contacting manner is to contact a feedstock liquor containing 2-alkylanthracene, a catalyst and an oxidation reaction solvent with an oxidizing agent to perform the oxidation reaction;

wherein,

The oxidizing agent is tert-butyl hydroperoxide;

The catalyst contains a support and an active component on the support;

Preferably, the content of the active component is 0.01-40 wt %, preferably 0.1-30 wt %, based on the weight of the support in the catalyst and based on the element content;

Preferably, the active component is one or more of elements under the group VA and transition metals, more preferably, the active component is one or more of elements under the group VA and metals under the group VB, the group VIB and the group VIII, most preferably, the active component is one or more of P, V, Cr, Mo, Fe and Co;

further preferably, the active component is a combination of an element under the group VA and a transition metal, more preferably, the active component is a combination of an element under the group VA and at least one metal of the group VB, the group VIB and the group VIII, most preferably, the active component is a combination of P and at least one of V, Cr, Mo, Fe and Co; optionally but preferably, based on the element content, the mass ratio of the transition metal to the element under the group VA is 1-20:1;

The support is a thermotolerant inorganic oxide;

Preferably, the thermotolerant inorganic oxide is one or more of silicon dioxide, magnesium oxide and silica-alumina composite oxide, in the silica-alumina composite oxide, as oxide, the content of $SiO_2$ is 0.01-70 wt %, preferably 5-40 wt %, the content of $Al_2O_3$ is 30-99.9 wt %, preferably 60-95 wt %;

The oxidation reaction solvent is one or more of $C_6$ or more, preferably $C_6$-$C_{12}$ alkane, cycloalkane and aromatic hydrocarbon, wherein, the aromatic hydrocarbon is substituted or unsubstituted, preferably one or more of mono- or poly-substituted benzenes, the substituent is one or more of $C_1$-$C_4$ alkyl and halogen, Preferably, the oxidation reaction solvent is one or more of halogenated benzenes;

Most preferably, the oxidation reaction solvent is one or more of monochlorobenzene, dichlorobenzene, trichlorobenzene and tetrachlorobenzene;

The condition of oxidation reaction includes: the reaction temperature is 10-150° C., preferably 20-100° C.; the reaction pressure is 0-1 MPa (gauge pressure), preferably 0-0.5 MPa (gauge pressure); the reaction time is 0.01-48 hours, preferably 0.5-24 hours;

The content of catalyst is 0.01-50 wt %, preferably 0.5-30 wt %, based on the total weight of catalyst and oxidation reaction solvent;

The mole ratio of the oxidizing agent to 2-alkylanthracene is 0.01:1-100:1, preferably 1:1-50:1.

The total content of 2-alkylanthracene is 0.1-80 wt %, preferably 5-50 wt %, based on the total weight of 2-alkylanthracene and the oxidation reaction solvent.

19. The use according to the preceding technical solution D18, wherein the catalyst is obtained by the following preparation method: impregnating a support with a solution containing a soluble compound of active component, drying and calcining the impregnated support;

Preferably, the impregnation temperature is 0-100° C., more preferably, 20-80° C.;

Preferably, the impregnation time is 4-24 hours, more preferably, 6-12 hours;

Preferably, the drying temperature is 90-125° C.,

Preferably, the drying time is 1-12 hours;

Preferably, the calcining temperature is 300-700° C.,

Preferably, the calcining time is 2-6 hours;

Preferably, the support and the soluble compound of active component are used in such an amount that based on the weight of the support in the catalyst, the content of the active component as element is 0.01-40 wt %, preferably 0.1-30 wt %;

Preferably, the soluble compound of active component is soluble compound(s) of one or more of elements under the group VA and transition metals; more preferably, the soluble compound of active component is soluble compound(s) of one or more of elements under the group VA and metals under the group VB, the group VIB and the group VIII, most preferably, the soluble compound of active component is soluble compound(s) of one or more elements of P, V, Cr, Mo, Fe and Co;

Further preferably, the soluble compound of active component is a combination of a soluble compound of an element under the group VA and a soluble compound of transition metal, more preferably, the soluble compound of active component is a combination of a soluble compound of an element under the group VA and a soluble compound of at least one metal of the group VB, the group VIB and the group VIII; most preferably, the soluble compound of active component is a combination of a soluble compound of P and a soluble compound of at least one element of V, Cr, Mo, Fe and Co; optionally but preferably, the soluble compound of active component is used in such an amount that as element(s) in the catalyst, the mass ratio of the transition metal to the element under the group VA is 1-20:1;

Preferably, the support is a thermotolerant inorganic oxide;

Preferably, the thermotolerant inorganic oxide is one or more of silicon dioxide, magnesium oxide and silica-alumina composite oxide, in the silica-alumina composite oxide, as oxide, the content of $SiO_2$ is 0.01-70 wt %, preferably 5-40 wt %, the content of $Al_2O_3$ is 30-99.9 wt %, preferably 60-95 wt %.

20. The use according to any one of the preceding technical solutions D15-D19, wherein the preparation of hydrogen peroxide using 2-alkylanthraquinone comprises subjecting a 2-alkylanthraquinone working fluid to hydrogenation, oxidation and extraction, characterized in that, prior to the hydrogenation, the 2-alkylanthraquinone working fluid is subjected to a pretreatment, The pretreatment method comprises: contacting the 2-alkylanthraquinone working fluid with an adsorbent in alkali liquor to perform an adsorption desulfurization and impurity removal, separating the 2-alkylanthraquinone working fluid that has been subjected to the adsorption desulfurization and impurity removal, and washing, The adsorbent is an amorphous alloy, and the amorphous alloy contains nickel, Preferably, based on the total weight of amorphous alloy, the content of nickel is 35-95 wt %, preferably 50-90 wt %;

More preferably, the amorphous alloy further contains one or more metals of aluminum, iron, chromium, copper, zinc, molybdenum and cobalt;

Further preferably, the 2-alkylanthraquinone working fluid is a fresh-formulated 2-alkylanthraquinone working fluid.

21. The use according to the preceding technical solution D20, wherein

Based on the total weight of amorphous alloy, the content of nickel is 35-95 wt %, the total content of other metals is 5-65 wt %, more preferably, based on the total weight of amorphous alloy, the content of nickel is 50-90 wt %, the total content of other metals is 10-50 wt %;

22. The use according to the preceding technical solution D20, wherein

The amorphous alloy contains nickel and aluminum, and one or more metals of iron, chromium, copper, zinc, molybdenum and cobalt, preferably at least one of a combination of chromium and iron, a combination of chromium and copper, a combination of chromium and molybdenum, a combination of chromium and cobalt;

Based on the total weight of amorphous alloy, the content of nickel is 35-95 wt %, the content of aluminum is 0.5-40 wt %, the total content of one or more metals of iron, chromium, copper, zinc, molybdenum and cobalt is 0.1-50 wt %;

Preferably, based on the total weight of amorphous alloy, the content of nickel is 50-90 wt %, the content of aluminum is 1-30 wt %, the total content of one or more metals of iron, chromium, copper, zinc, molybdenum and cobalt is 1-40 wt %;

More preferably, based on the total weight of amorphous alloy, the content of nickel is 50-90 wt %, the content of aluminum is 1-15 wt %, the total content of one or more metals of iron, chromium, copper, zinc, molybdenum and cobalt is 5-40 wt %.

23. The use according to any of the preceding solutions D19-D21, wherein

In the X-ray diffraction pattern of the adsorbent, a diffuse peak appears at 45±1° in the 2θ angle range of 20-80°.

24. The use according to any of the preceding technical solutions D19-D21, wherein The condition for contacting the 2-alkylanthraquinone working fluid with the adsorbent in the alkali liquor comprises:

The temperature is 10-200° C., preferably 25-170° C.,

The pressure is 0-3 MPa (gauge pressure), preferably 0-2 MPa (gauge pressure);

Preferably, the number of contact is 1-5, more preferably 2-4, and the time for each contact is 0.01-24 hours, more preferably 0.5-8 hours;

Preferably, the contact is performed under stirring, and the rotation speed of the stirring is 500-2000 rpm, and more preferably 800-1200 rpm;

The used amount of the adsorbent is 0.01-40 wt %, preferably 1-10 wt %, based on the weight of the 2-alkylanthraquinone working fluid, The alkali in the alkali liquor is an inorganic base, the inorganic base is at least one of sodium hydroxide, potassium hydroxide, sodium carbonate and potassium carbonate, preferably sodium hydroxide, and the alkali liquor is preferably an aqueous alkali solution;

The volume ratio of the alkali liquor to the 2-alkylanthraquinone working fluid is 0.1-10, preferably 0.5-2.

25. The use according to any of the preceding technical solutions D19-D24, wherein The washing condition is such one that the pH value of the washed 2-alkylanthraquinone working fluid is neutral, and preferably, the washing comprises acid washing and water washing in sequence;

The acid used for acid washing is an inorganic acid, which is at least one of sulfuric acid, hydrochloric acid, nitric acid and phosphoric acid, preferably phosphoric acid, and the acid is used in the form of acid liquor, preferably an aqueous acid solution;

The condition for acid washing comprises: the temperature is 5-100° C., preferably 20-60° C., the pressure is 0-1 MPa (gauge pressure), preferably 0-0.5 MPa (gauge pressure);

The volume ratio of the acid liquor to the 2-alkylanthraquinone working fluid is 0.1-10, preferably 0.5-2;

Preferably, the number of acid washing is 1-5, preferably 2-4, and the time for each acid washing is 0.01-24 hours, preferably 0.5-8 hours;

Preferably, the acid washing is performed under stirring, and the rotation speed of the stirring is 500-2000 rpm, and more preferably 800-1200 rpm;

The condition for water washing comprises: the pressure is 0-1 MPa (gauge pressure), preferably 0-0.5 MPa (gauge pressure); the temperature is 5-100° C., preferably 20-60° C.;

The volume ratio of water to the 2-alkylanthraquinone working fluid is 0.1-10, preferably 0.5-2;

Preferably, the number of water washing is 1-5, preferably 2-4, and the time for each water washing is 0.01-24 hours, preferably 0.5-8 hours;

Preferably, the water washing is performed under stirring, and the rotation speed of the stirring is 500-2000 rpm, and more preferably 800-1200 rpm.

The present invention also provides a series of technical solutions in the group A, as follows:

1. A method for preparing 2-alkylanthraquinone by catalytic oxidation of 2-alkylanthracene obtained by alkylation of anthracene, which is characterized in that said preparation method comprises the following steps:

(1) contacting anthracene and an alkylation reagent under an alkylation condition and in the presence of an alkylation reaction solvent and a catalyst to perform the alkylation reaction to produce a reaction product containing alkylanthracenes, the alkylation reaction solvent is a combination of solvent A having a dielectric constant of 1-10 at 20° C. and solvent B having a dielectric constant of more than 10 to 50 or less at 20° C.;

(2) separating the reaction product containing alkylanthracene obtained from step (1), the separation method comprising: the separation of anthracene by melting crystallization and the separation of 2-alkylanthracene by distillation;

(3) contacting 2-alkylanthracene obtained from step (2) with an oxidizing agent under an oxidizing condition and in the presence of an oxidation reaction solvent and a catalyst to perform an oxidation reaction, the oxidizing agent is hydrogen peroxide, the catalyst is one or more of alkaline earth metal oxide, alkaline earth metal hydroxide, oxygen-containing compound of transition metal and oxygen-containing compound of lanthanide series metal.

2. The preparation method according to the technical solution A1, wherein, in step (1), The solvent A is one or more of $C_6$ or more, preferably $C_6$-$C_{12}$ alkane, cycloalkane and aromatic hydrocarbon; wherein, the aromatic hydrocarbon is substituted or unsubstituted, preferably one or more of mono- or poly-substituted benzenes, more preferably one or more of poly-substituted benzenes, the substituent is one or more of $C_1$-$C_4$ alkyl and halogen;

more preferably, The solvent A is one or more of polyalkyl substituted benzenes, most preferably, the solvent A is one or more of 1,3,5-trimethylbenzene, 1,2,3,5-tetramethylbenzene, 1,3,4,5-tetramethylbenzene, 1,3,5,6-tetramethylbenzene and 2,3,5,6-tetramethylbenzene;

The solvent B is N-alkyl substituted amide, wherein, the number of alkyl substituent is 1-2, each alkyl substituent is independently $C_1$-$C_4$ alkyl; more preferably, the solvent B is one or more of N,N-dimethylformamide, N,N-dimethylacetamide and N,N-dimethylpropionamide, most preferably, the solvent B is N,N-dimethylformamide.

3. The preparation method according to the technical solution A1 or A2, wherein, in step (1), the volume ratio of the solvent A to the solvent B is 0.01-100, preferably 0.1-10.

4. The preparation method according to any of the technical solutions A1-A3, wherein, in step (1), based on the total weight of anthracene and alkylation reaction solvent, the content of anthracene is 5-60 wt %, preferably 8-50 wt %.

5. The preparation method according to the technical solution A1, wherein, in step (1), the alkylation reagent is one or more of alkene, alcohol, halohydrocarbon and ether substances containing 2-8 carbon atoms, preferably one or more of alkene, alcohol, halohydrocarbon and ether substances containing 4-6 carbon atoms, more preferably monoolefin containing 4-6 carbon atoms.

6. The preparation method according to the technical solution A1 or A5, wherein, in step (1), the mole ratio of anthracene to alkylation reagent is 0.2:1-20:1, preferably 0.5:1-5:1.

7. The preparation method according to the technical solution A1, wherein, in step (1), the contacting manner is to contact a feedstock liquor containing anthracene, catalyst and alkylation reaction solvent with an alkylation reagent to perform the alkylation reaction.

8. The preparation method according to the technical solution A7, wherein, in step (1), the catalyst is a solid acid catalyst, the solid acid catalyst contains an active molecular sieve and a binder, based on the total weight of the solid acid catalyst, the content of active molecular sieve is 30-95 wt %, the content of binder is 5-70 wt %, the active molecular sieve is one or more of X zeolite, Y zeolite, beta zeolite, ZSM-5 zeolite, SAPO zeolite and mesoporous zeolite, preferably Y zeolite; the binder is an inorganic binder, the inorganic binder is a thermotolerant inorganic oxide and/or silicate, preferably alumina;

Based on the total weight of the feedstock liquor containing anthracene, catalyst and alkylation reaction solvent, the content of catalyst is 0.01-50 wt %, preferably 0.5-30 wt %.

9. The preparation method according to the technical solution A1, wherein, in step (1), the alkylation reaction condition includes: the reaction temperature is 100-250° C., preferably 120-200° C.; the reaction pressure is 0-1 MPa, preferably 0.05-0.5 MPa; the reaction time is 0.01-48 hours, preferably 0.5-24 hours.

10. The preparation method according to any of the technical solutions A1-A9, wherein, the reaction product containing alkylanthracene obtained from step (1) contains anthracene and a product of a series of alkylanthracenes containing 2-alkylanthracene;

The step (2) comprises:

(2-2) heating the reaction product containing the alkylanthracene obtained from step (1) to a molten state, cooling and crystallizing, separating to obtain an anthracene crystal and a stream of the product of a series of alkylanthracenes containing 2-alkylanthracene, heating the anthracene crystal to sweat, and separating the sweating liquor and the anthracene crystal;

(2-3) separating 2-alkylanthracene from the product of a series of alkylanthracenes containing 2-alkylanthracene by one-step distillation or multiple-step distillation.

11. The preparation method according to the technical solution A10, wherein In step (2-2), the melting temperature is 200-270° C., preferably 210-250° C.

12. The preparation method according to the technical solution A10 or A11, wherein, in step (2-2), the temperature for cooling and crystallizing is 180-210° C., the temperature reduction rate for cooling and crystallizing is 0.1-10° C./h, the time for cooling and crystallizing is 1-5 hours; preferably, the temperature for cooling and crystallizing is 190-200° C., the temperature reduction rate for cooling and crystallizing is 0.5-5° C./h, the time for cooling and crystallizing is 1.5-4 hours.

13. The preparation method according to the technical solution A12, wherein in step (2-2), in the cooling and crystallization, a step of adding anthracene as crystal seeds in an amount of 0.1-10 wt %, preferably 0.2-5 wt %, based on the mass of the molten mixture, is further included.

14. The preparation method according to the technical solution A10 or A11, wherein, in step (2-2), the temperature-rise rate for sweating the anthracene crystal is 0.1-8° C./h, preferably 0.2-4° C./h; the temperature to which the temperature is increased and at which the sweating is terminated is lower than the melting temperature of the anthracene crystal, preferably the temperature to which the temperature is increased and at which the sweating is terminated is lower than or equal to 210° C., more preferably, the temperature is increased to a temperature 5-15° C. higher than the cooling crystallization temperature, and the sweating is terminated when the temperature is below 210° C.; further preferably, the temperature at which the sweating is terminated is 190-210° C., most preferably 195-205° C.

15. The preparation method according to the technical solution A14, wherein the sweating amount is 5-40%, preferably 10-30% by weight of the anthracene crystal.

16. The preparation method according to the technical solution A14, wherein the method further comprises: recycling the sweating liquor back to the step of melting crystallization, and carrying out the melting crystallization together with the reaction product containing alkylanthracene.

17. The preparation method according to the technical solution A10, wherein in step (2-3), if the product of a series of alkylanthracenes containing 2-alkylanthracene is a mixture of two substances, or a mixture of three or more substances, and the boiling point of 2-alkylanthracene is the lowest or the highest; then a one-step distillation separation of the 2-alkylanthracene is performed.

18. The preparation method according to the technical solution A10, wherein in step (2-3), if the product of a series of alkylanthracenes containing 2-alkylanthracene is a mixture of three or more substances, and the boiling point of the 2-alkylanthracene is between the boiling points of a substance with the highest boiling point and a substance with the lowest boiling point in the mixture; then a multiple-step distillation is performed, and the multiple-step distillation comprises:

Mode 1:

A stream of the product of a series of alkylanthracenes containing 2-alkylanthracene is subjected to a first distillation separation to produce a distillate containing light component Cj1-anthracene and a bottom product containing heavy component Cj2-anthracene; the distillate containing light component Cj1-anthracene is subjected to a second distillation to produce a distillate containing light component Cj3-anthracene and a bottom product containing target product Ci-anthracene;

Wherein the light component Cj1-anthracene is an alkylanthracene product of which the total carbon number j1 of alkyl side chain is an integer $1 \leq j1 < i+1$, the heavy component Cj2-anthracene is an alkylanthracene product of which the total carbon number j2 of alkyl side chain is an integer $i < j2 < 41$, and the light component Cj3-anthracene is an alkylanthracene product of which the total carbon number j3 of alkyl side chain is an integer $1 \leq j3 \leq i$;

or,

Mode 2:

A stream of the product of a series of alkylanthracenes containing 2-alkylanthracene is subjected to a third distillation to produce a distillate containing light component Cm1-anthracene and a bottom product containing heavy component Cm2-anthracene; the bottom product containing heavy component Cm2-anthracene is subjected to a fourth distillation to produce a distillate containing target product Ci-anthracene and a bottom product containing heavy component Cm3-anthracene;

Wherein the light component Cm1-anthracene is an alkylanthracene product of which the total carbon number m1 of alkyl side chain is an integer $1 < m1 < i$, the heavy component Cm2-anthracene is an alkylanthracene product of which the total carbon number m2 of alkyl side chain is an integer $i-1 < m2 < 41$, and the Cm3-anthracene is an alkylanthracene product of which the total carbon number m3 of alkyl side chain is an integer $i < m3 < 41$;

wherein, in the target product Ci-anthracene, i represents the total carbon number of alkyl side chain, and i=an integer of 4-7.

19. The preparation method according to the technical solution A18, wherein in the multiple-step vacuum distillation step, in Mode 1, the condition of the first vacuum distillation includes: the top pressure of the distillation column is 0.01-20 KPa, the temperature at the column bottom is 180-360° C., the theoretical plate number is 20-90, the top reflux ratio is 0.5-8; more preferably, the top pressure of the column is 0.1-10 KPa, the temperature at the column bottom is 210-340° C., the theoretical plate number is 30-75, the top reflux ratio is 1-7; further preferably, the top pressure of the distillation column is 0.5-2 KPa, the temperature at the column bottom is 220-320° C., the theoretical plate number is 40-75, the top reflux ratio is 1-3.

20. The preparation method according to the technical solution A18 or A19, wherein, in the multiple-step vacuum distillation step, in Mode 1, the condition of the second vacuum distillation includes: the top pressure of the distillation column is 0.01-20 KPa, the temperature at the column bottom is 180-330° C., the theoretical plate number is 20-90, the top reflux ratio is 0.5-8; more preferably, the top pressure of the column is 0.1-10 KPa, the temperature at the column bottom is 200-310° C., the theoretical plate number is 30-75, the top reflux ratio is 1-7; further preferably, the top pressure of the distillation column is 0.5-2 KPa, the temperature at the column bottom is 220-300° C., the theoretical plate number is 40-75, the top reflux ratio is 1-5.

21. The preparation method according to the technical solution A18, wherein in the multiple-step vacuum distillation step, in Mode 2, the condition of the third vacuum distillation includes: the top pressure of the distillation column is 0.01-20 KPa, the temperature at the column bottom is 180-360° C., the theoretical plate number is 20-90, the top reflux ratio is 0.5-8; more preferably, the top pressure of the column is 0.1-10 KPa, the temperature at the column bottom is 210-340° C., the theoretical plate number is 30-75, the top reflux ratio is 1-7; further preferably, the top pressure of the distillation column is 0.5-2 KPa, the temperature at the column bottom is 220-320° C., the theoretical plate number is 40-75, the top reflux ratio is 1-3.

22. The preparation method according to the technical solution A18 or A21, wherein, in the multiple-step vacuum distillation step, in Mode 2, the condition of the fourth vacuum distillation includes: the top pressure of the distillation column is 0.01-20 KPa, the temperature at the column bottom is 180-330° C., the theoretical plate number is 20-90, the top reflux ratio is 0.5-8; more preferably, the top pressure of the column is 0.1-10 KPa, the temperature at the column bottom is 200-310° C., the theoretical plate number is 30-75, the top reflux ratio is 1-7; further preferably, the top pressure of the distillation column is 0.5-2 KPa, the temperature at the column bottom is 220-300° C., the theoretical plate number is 40-75, the top reflux ratio is 1-5.

23. The preparation method according to any of the technical solutions A10 to A22, wherein, the reaction product containing the alkylanthracene obtained from step (1) further contains an alkylation reaction solvent;

The step (2) further concludes a step (2-1) of separating the alkylation reaction solvent before the separation of anthracene by melting crystallization and the separation of 2-alkylanthracene by distillation;

The separation method comprises (2-1) the reaction product containing the alkylanthracene obtained from step (1) is subjected to distillation in a distillation column to produce a distillate containing the alkylation reaction solvent, and a bottom product containing anthracene and the product of a series of alkylanthracenes containing 2-alkylanthracene.

24. The preparation method according to the technical solution A23, wherein In step (2-1), the distillation condition comprises: the distillation temperature at the column bottom is 100-300° C., preferably 150-200° C., the top pressure of the distillation column is normal pressure.

25. The preparation method according to the technical solution A1, wherein, In step (3), the catalyst is one or more of oxygen-containing compounds of group IIA, group IVB, group VB, group VIB, group VIIB, group VIII metals and lanthanide series metal.

26. The preparation method according to the technical solution A25, wherein the catalyst is one or more of oxygen-containing compound(s) of Ca, Ba, Ti, Zr, V, Cr, Mo, W, Mn, Ru, Co, Ni, La and Ce.

27. The preparation method according to the technical solution A26, wherein the catalyst is one or more of calcium hydroxide, barium hydroxide, metatitanic acid, zirconium dioxide, zirconyl nitrate, sodium metavanadate, potassium chromate, chromium sesquioxide, sodium molybdate, ammonium molybdate, molybdenum trioxide, sodium tungstate, manganese sesquioxide, manganese dioxide, ruthenium dioxide, cobaltic oxide, nickel oxide, nickel sesquioxide, lanthanum nitrate, lanthanum sesquioxide, and cerium dioxide.

28. The preparation method according to the technical solution A1, wherein, the contacting manner is to contact a feedstock liquor containing 2-alkylanthracene, a catalyst and an oxidation reaction solvent with an oxidizing agent to perform the oxidation reaction.

29. The preparation method according to any of the technical solutions A1 and A25-A28, wherein, the mole ratio of the oxidizing agent to the catalyst is 0.01:1-100:1, preferably 0.1:1-30:1.

30. The preparation method according to any of the technical solutions A1 and A25-A28, wherein, the condition of oxidation reaction includes: the reaction temperature is 10-200° C., preferably 20-120° C.; the reaction pressure is 0-1 MPa, preferably 0-0.5 MPa; the reaction time is 0.01-48 hours, preferably 0.5-24 hours.

31. The preparation method according to any of the technical solutions A1 and A25-A28, wherein, the hydrogen peroxide is used in the form of an aqueous hydrogen peroxide solution; the mole ratio of the oxidizing agent to 2-alkylanthracene is 0.01:1-100:1, preferably 1:1-50:1.

32. The preparation method according to any of the technical solutions A1 and A25-A28, wherein, the oxidation reaction solvent is a solvent having a dielectric constant of greater than 2.8 at 20° C., preferably, the oxidation reaction solvent is a solvent having a dielectric constant of greater than 2.8 to less than or equal to 50 at 20° C.;
more preferably, the oxidation reaction solvent is one or more of fatty alcohol with carbon number of 1-4, tetrahydrofuran, acetone, N-alkyl substituted amide and N-alkyl pyrrolidone; wherein, the number of alkyl substituent is 1-2, each alkyl substituent is independently $C_1$-$C_4$ alkyl; most preferably, the oxidation reaction solvent is one or more of methanol, tert-butyl alcohol, acetone, N,N-dimethylformamide, N,N-dimethylacetamide, N,N-dimethylpropionamide, N-methylpyrrolidone and N-ethylpyrrolidone;
based on the total weight of 2-alkylanthracene and the oxidation reaction solvent, the total content of 2-alkylanthracene is 0.1-80 wt %, preferably 5-50 wt %.

33. The preparation method according to any of the technical solutions A1 and A25-A28, wherein, the oxidation reaction solvent is a combination of solvent A having a dielectric constant of 1-10 at 20° C. and solvent B having a dielectric constant of more than 10 to 50 or less at 20° C.;
the solvent A is one or more of $C_6$ or more, preferably $C_6$-$C_{12}$ alkane, cycloalkane and aromatic hydrocarbon;
wherein, the aromatic hydrocarbon is substituted or unsubstituted, preferably one or more of mono- or poly-substituted benzenes, more preferably one or more of poly-substituted benzenes, the substituent is one or more of $C_1$-$C_4$ alkyl and halogen; further preferably, the solvent A is one or more of polyalkyl substituted benzenes, most preferably, the solvent A is one or more of 1,3,5-trimethylbenzene, 1,2,3,5-tetramethylbenzene, 1,3,4,5-tetramethylbenzene, 1,3,5,6-tetramethylbenzene and 2,3,5,6-tetramethylbenzene;
the solvent B is N-alkyl substituted amide, wherein, the number of alkyl substituent is 1-2, each alkyl substituent is $C_1$-$C_4$ alkyl independently; more preferably, the solvent B is one or more of N,N-dimethylformamide, N,N-dimethylacetamide and N,N-dimethylpropionamide, most preferably, the solvent B is N,N-dimethylformamide; based on the total weight of 2-alkylanthracene and the oxidation reaction solvent, the total content of 2-alkylanthracene is 0.1-80 wt %, preferably 5-50 wt %.

34. The preparation method according to the technical solution A33, wherein the volume ratio of the solvent A to the solvent B is 0.01-100, preferably 0.05-10.

The present invention further provides a series of technical solutions in the group B, as follows:

1. A method for preparing 2-alkylanthraquinone by catalytic oxidation of 2-alkylanthracene obtained by separation from the reaction of anthracene, which is characterized in that said preparation method comprises the following steps:
   (1) preparing a reaction product containing alkylanthracene from anthracene;
   (2) separating the reaction product containing alkylanthracene obtained from step (1), the separation method comprising: the separation of anthracene by melting crystallization and the separation of 2-alkylanthracene by distillation;
   (3) contacting 2-alkylanthracene obtained in step (2) with an oxidizing agent under an oxidizing condition and in the presence of an oxidation reaction solvent and a catalyst to perform the oxidation reaction, the oxidizing agent is tert-butyl hydroperoxide, the catalyst contains a support and an active component on the support, the active component is one or more of elements under the group VA and transition metals.

2. The preparation method according to the technical solution B1, wherein, In step (1), the process of preparing the reaction product containing alkylanthracene from anthracene comprises contacting anthracene with an alkylating agent under an alkylation condition and in the presence of an alkylation reaction solvent and a catalyst to perform the alkylation reaction;
Preferably, the contacting manner is to contact a feedstock liquor containing anthracene, catalyst and alkylation reaction solvent with an alkylation reagent to perform the alkylation reaction.

3. The preparation method according to the technical solution B2, wherein, The alkylation reagent is one or more of alkene, alcohol, halohydrocarbon and ether substances containing 2-8 carbon atoms, preferably one or more of alkene, alcohol, halohydrocarbon and ether substances containing 4-6 carbon atoms, more preferably mono-olefin containing 4-6 carbon atoms.

4. The preparation method according to the technical solution B2 or B3, wherein, in step (1), the mole ratio of anthracene to alkylation reagent is 0.2:1-20:1, preferably 0.5:1-5:1.

5. The preparation method according to the technical solution B2, wherein, in step (1), the alkylation reaction solvent is a solvent having a dielectric constant of 1-10 at 20° C., the alkylation reaction solvent is one or more of $C_6$ or more, preferably $C_6$-$C_{12}$ alkane, cycloalkane and aromatic hydrocarbon; wherein, the aromatic hydrocarbon is substituted or unsubstituted, preferably one or more of mono- or poly-substituted benzenes; more preferably one or more of poly-substituted benzenes, the substituent is one or more of $C_1$-$C_4$ alkyl and halogen; further preferably, the alkylation reaction solvent is one or more of polyalkyl substituted benzenes; most preferably, the alkylation reaction solvent is one or more of 1,3,5-trimethylbenzene, 1,2,3,5-tetramethylbenzene, 1,3,4,5-tetramethylbenzene, 1,3,5,6-tetramethylbenzene and 2,3,5,6-tetramethylbenzene; Based on the total weight of anthracene and alkylation reaction solvent, the content of anthracene is 5-60 wt %, preferably 8-50 wt %.

6. The preparation method according to any of the technical solutions B2-B5, wherein, In step (1), the alkylation reaction condition includes: the reaction temperature is 100-250° C., preferably 120-200° C.; the reaction pressure is 0-1 MPa, preferably 0.05-0.5 MPa; the reaction time is 0.01-48 hours, preferably 0.5-24 hours.

7. The preparation method according to any of the technical solutions B2-B5, wherein, In step (1), the catalyst is one or more of liquid acids, preferably methanesulfonic acid and/or paratoluenesulfonic acid; based on the total weight of the feedstock liquor containing anthracene, catalyst and alkylation reaction solvent, the content of catalyst is 0.01-50 wt %, preferably 0.5-30 wt %.

8. The preparation method according to any of the technical solutions B1-B7, wherein, The reaction product containing the alkylanthracene obtained from step (1) contains anthracene and a product of a series of alkylanthracenes containing 2-alkylanthracene;

The step (2) comprises:
(2-2) heating the reaction product containing the alkylanthracene obtained from step (1) to a molten state, cooling and crystallizing, separating to obtain an anthracene crystal and a stream of the product of a series of alkylanthracenes containing 2-alkylanthracene, heating the anthracene crystal to sweat, and separating the sweating liquor and the anthracene crystal;
(2-3) separating 2-alkylanthracene from the product of a series of alkylanthracenes containing 2-alkylanthracene by one-step distillation or multiple-step distillation.

9. The preparation method according to the technical solution B8, wherein, in step (2-2), the melting temperature is 200-270° C., preferably 210-250° C.

10. The preparation method according to the technical solution B8 or B9, wherein, in step (2-2), the temperature for cooling and crystallizing is 180-210° C., the temperature reduction rate for cooling and crystallizing is 0.1-10° C./h, the time for cooling and crystallizing is 1-5 hours; preferably, the temperature for cooling and crystallizing is 190-200° C., the temperature reduction rate for cooling and crystallizing is 0.5-5° C./h, the time for cooling and crystallizing is 1.5-4 hours.

11. The preparation method according to the technical solution B10, wherein in step (2-2), In the cooling and crystallization, a step of adding anthracene as crystal seeds in an amount of 0.1-10 wt %, preferably 0.2-5 wt %, based on the mass of the molten mixture, is further included.

12. The preparation method according to the technical solution B8 or B9, wherein, in step (2-2), the temperature-rise rate for sweating the anthracene crystal is 0.1-8° C./h, preferably 0.2-4° C./h; the temperature to which the temperature is increased and at which the sweating is terminated is lower than the melting temperature of the anthracene crystal, preferably the temperature to which the temperature is increased and at which the sweating is terminated is lower than or equal to 210° C., more preferably, the temperature is increased to a temperature 5-15° C. higher than the cooling crystallization temperature, and the sweating is terminated when the temperature is below 210° C.; further preferably, the temperature at which the sweating is terminated is 190-210° C., most preferably 195-205° C.

13. The preparation method according to the technical solution B12, wherein The sweating amount is 5-40%, preferably 10-30% by weight of the anthracene crystal.

14. The preparation method according to the technical solution B12, wherein The method further comprises: recycling the sweating liquor back to the step of melting crystallization, and carrying out the melting crystallization together with the reaction product containing alkylanthracene.

15. The preparation method according to the technical solution B8, wherein, In step (2-3), if the product of a series of alkylanthracenes containing 2-alkylanthracene is a mixture of two substances, or a mixture of three or more substances, and the boiling point of 2-alkylanthracene is the lowest or the highest; then a one-step distillation separation of the 2-alkylanthracene is performed.

16. The preparation method according to the technical solution B8, wherein, In step (2-3), if the product of a series of alkylanthracenes containing 2-alkylanthracene is a mixture of three or more substances, and the boiling point of the 2-alkylanthracene is between the boiling points of a substance with the highest boiling point and a substance with the lowest boiling point in the mixture; then a multiple-step distillation is performed, and the multiple-step distillation comprises:

Mode 1:
A stream of the product of a series of alkylanthracenes containing 2-alkylanthracene is subjected to a first distillation separation to produce a distillate containing light component Cj1-anthracene and a bottom product containing heavy component Cj2-anthracene; the distillate containing light component Cj1-anthracene is subjected to a second distillation to produce a distillate containing light component Cj3-anthracene and a bottom product containing target product Ci-anthracene;
Wherein the light component Cj1-anthracene is an alkylanthracene product of which the total carbon number j1 of alkyl side chain is an integer $1 < j1 < i+1$, the heavy component Cj2-anthracene is an alkylanthracene product of which the total carbon number j2 of alkyl side chain is an integer $i < j2 < 41$, and the light component Cj3-anthracene is an alkylanthracene product of which the total carbon number j3 of alkyl side chain is an integer $1 < j3 < i$;

or,

Mode 2:
A stream of the product of a series of alkylanthracenes containing 2-alkylanthracene is subjected to a third distillation to produce a distillate containing light component Cm1-anthracene and a bottom product containing heavy component Cm2-anthracene; the bottom product containing heavy component Cm2-anthracene is subjected to a fourth distillation to produce a distillate containing target product Ci-anthracene and a bottom product containing heavy component Cm3-anthracene;
Wherein the light component Cm1-anthracene is an alkylanthracene product of which the total carbon number m1 of alkyl side chain is an integer $1 < m1 < i$, the heavy component Cm2-anthracene is an alkylanthracene product of which the total carbon number m2 of alkyl side chain is an integer $i-1 < m2 < 41$, and the Cm3-anthracene is an alkylanthracene product of which the total carbon number m3 of alkyl side chain is an integer $i < m3 < 41$;
Wherein, in the target product Ci-anthracene, i represents the total carbon number of alkyl side chain, and i=an integer of 4-7.

17. The preparation method according to the technical solution B16, wherein in the multiple-step vacuum distillation step, in Mode 1, the condition of the first vacuum distillation includes: the top pressure of the distillation column is 0.01-20 KPa, the temperature at the column bottom is 180-360° C., the theoretical plate number is 20-90, the top reflux ratio is 0.5-8; more preferably, the top pressure of the column is 0.1-10 KPa, the temperature at the column bottom is 210-340° C., the theoretical plate number is 30-75, the top reflux ratio is 1-7; further preferably, the top pressure of the distillation column is 0.5-2 KPa, the temperature at the column bottom is 260-320° C., the theoretical plate number is 40-75, the top reflux ratio is 1-3.

18. The preparation method according to the technical solution B16 or B17, wherein, In the multiple-step vacuum distillation step, in Mode 1, the condition of the second vacuum distillation includes: the top pressure of the distillation column is 0.01-20 KPa, the temperature at the column bottom is 180-330° C., the theoretical plate number is 20-90, the top reflux ratio is 0.5-8; more preferably, the top pressure of the column is 0.1-10 KPa, the temperature at the column bottom is 200-310° C., the theoretical plate number is 30-75, the top reflux ratio is 1-7; further preferably, the top pressure of the distillation column is 0.5-2 KPa, the temperature at the column bottom is 220-305° C., the theoretical plate number is 40-75, the top reflux ratio is 1-5.

19. The preparation method according to the technical solution B16, wherein in the multiple-step vacuum distillation step, in Mode 2, the condition of the third vacuum distillation includes: the top pressure of the distillation column is 0.01-20 KPa, the temperature at the column bottom is 180-360° C., the theoretical plate number is 20-90, the top reflux ratio is 0.5-8; more preferably, the top pressure of the column is 0.1-10 KPa, the temperature at the column bottom is 210-340° C., the theoretical plate number is 30-75, the top reflux ratio is 1-7; further preferably, the top pressure of the distillation column is 0.5-2 KPa, the temperature at the column bottom is 260-320° C., the theoretical plate number is 40-75, the top reflux ratio is 1-3.

20. The preparation method according to the technical solution B16 or B19, wherein, in the multiple-step vacuum distillation step, in Mode 2, the condition of the fourth vacuum distillation includes: the top pressure of the distillation column is 0.01-20 KPa, the temperature at the column bottom is 180-330° C., the theoretical plate number is 20-90, the top reflux ratio is 0.5-8; more preferably, the top pressure of the column is 0.1-10 KPa, the temperature at the column bottom is 200-310° C., the theoretical plate number is 30-75, the top reflux ratio is 1-7; further preferably, the top pressure of the distillation column is 0.5-2 KPa, the temperature at the column bottom is 220-305° C., the theoretical plate number is 40-75, the top reflux ratio is 1-5.

21. The preparation method according to any of the technical solutions B8 to B20, wherein the reaction product containing the alkylanthracene obtained from step (1) further contains a reaction solvent;

The step (2) further concludes a step (2-1) of separating the reaction solvent before the separation of anthracene by melting crystallization and the separation of 2-alkylanthracene by distillation;

The separation method comprises (2-1) the reaction product containing the alkylanthracene obtained from step (1) is subjected to distillation in a distillation column to produce a distillate containing the reaction solvent, and a bottom product containing anthracene and the product of a series of alkylanthracenes containing 2-alkylanthracene.

22. The preparation method according to the technical solution B21, wherein in step (2-1), the distillation condition comprises: the distillation temperature at the column bottom is 100-300° C., preferably 150-200° C., the top pressure of the distillation column is normal pressure.

23. The preparation method according to the technical solution B1, wherein, In step (3), the active component is one or more of elements under the group VA and metals under the group VB, the group VIB and the group VIII, preferably a combination of an element under the group VA and at least one metal of the group VB, the group VIB and the group VIII.

24. The preparation method according to the technical solution B23, wherein The active component is one or more of P, V, Cr, Mo, Fe and Co, preferably a combination of P and at least one of V, Cr, Mo, Fe and Co.

25. The preparation method according to the technical solution B1, wherein, The support is a thermotolerant inorganic oxide, the thermotolerant inorganic oxide is one or more of silicon dioxide, magnesium oxide and silica-alumina composite oxide, in the silica-alumina composite oxide, as oxide, the content of $SiO_2$ is 0.01-70 wt %, preferably 5-40 wt %, the content of $Al_2O_3$ is 30-99.9 wt %, preferably 60-95 wt %.

26. The preparation method according to any of the technical solutions B1 and B23 to B25, wherein, based on the weight of the support in the catalyst and based on the element content, the content of the active component is 0.01-40 wt %, preferably 0.1-30 wt %.

27. The preparation method according to the technical solution B26, wherein the active component in the catalyst is a combination of an element under the group VA and a transition metal, based on the element content, the mass ratio of the transition metal to the element under the group VA is 1-20:1.

28. The preparation method according to any one of technical solutions B1 and B23-B27, wherein the preparation method of the catalyst comprises: impregnating a support with a solution containing the soluble compound of active component, drying and calcining the impregnated support, the soluble compound of the active component is soluble compound(s) of one or more of elements under the group VA and transition metals.

29. The preparation method according to the technical solution B28, wherein The soluble compound of active component is soluble compound(s) of one or more of elements under the group VA and metals under the group VB, the group VIB and the group VIII, preferably a combination of a soluble compound of an element under the group VA and a soluble compound of at least one metal of the group VB, the group VIB and the group VIII.

30. The preparation method according to the technical solution B29, wherein The soluble compound of active component is soluble compound(s) of one or more elements of P, V, Cr, Mo, Fe and Co, preferably a combination of P and a soluble compound of at least one element of V, Cr, Mo, Fe and Co.

31. The preparation method according to the technical solution B28, wherein the support and the soluble compound of active component are used in such an amount that based on the weight of the support in the catalyst, the content of the active component as element is 0.01-40 wt %, preferably 0.1-30 wt %.

32. The preparation method according to the technical solution B31, wherein the soluble compound of active component is a combination of a soluble compound of an element under the group VA and a soluble compound of transition metal, the soluble compound of active component is used in such an amount that as element(s) in the catalyst, the mass ratio of the transition metal to the element under the group VA is 1-20:1.

33. The preparation method according to the technical solution B28, wherein The impregnation condition includes: the impregnation temperature is 0-100° C., preferably 20-80° C., the impregnation time is 4-24 hours, preferably 6-12 hours; the temperature for drying the impregnated support is 90-125° C., the drying time is 1-12 hours; the temperature for calcining the impregnated support is 300-700° C., the calcining time is 2-6 hours.

34. The preparation method according to the technical solution B1, wherein, The contacting manner is to contact a feedstock liquor containing 2-alkylanthracene, a catalyst and an oxidation reaction solvent with an oxidizing agent to perform the oxidation reaction.

35. The preparation method according to the technical solution B34, wherein Based on the total weight of catalyst and oxidation reaction solvent, the content of catalyst is 0.01-50 wt %, preferably 0.5-30 wt %.

36. The preparation method according to any of technical solutions B1 and B23-B35, wherein, the condition of oxidation reaction includes: the reaction temperature is 10-150° C., preferably 20-100° C.; the reaction pressure is 0-1 MPa, preferably 0-0.5 MPa; the reaction time is 0.01-48 hours, preferably 0.5-24 hours.

37. The preparation method according to any of technical solutions B1 and B23-B35, wherein, the mole ratio of the oxidizing agent to 2-alkylanthracene is 0.01:1-100:1, preferably 1:1-50:1.

38. The preparation method according to any of technical solutions B1 and B23-B35, wherein, the oxidation reaction solvent is one or more of $C_6$ or more, preferably $C_6$-$C_{12}$ alkane, cycloalkane and aromatic hydrocarbon; wherein, the aromatic hydrocarbon is substituted or unsubstituted, preferably one or more of mono- or poly-substituted benzenes, the substituent is one or more of $C_1$-$C_4$ alkyl and halogen; further preferably, the oxidation reaction solvent is one or more of halogenated benzenes; most preferably, the oxidation reaction solvent is one or more of monochlorobenzene, dichlorobenzene, trichlorobenzene and tetrachlorobenzene;

Based on the total weight of 2-alkylanthracene and the oxidation reaction solvent, the total content of 2-alkylanthracene is 0.1-80 wt %, preferably 5-50 wt %.

The present invention further provides a series of technical solutions in the group C, as follows:

1. A method for pretreating a 2-alkylanthraquinone working fluid, which is characterized in that the method comprises: contacting the 2-alkylanthraquinone working fluid with an adsorbent in alkali liquor to perform an adsorption desulfurization and impurity removal; separating the 2-alkylanthraquinone working fluid that has been subjected to the adsorption desulfurization and impurity removal; and washing, the adsorbent is an amorphous alloy, and the amorphous alloy contains nickel.

2. The pretreatment method according to technical solution C1, wherein, based on the total weight of amorphous alloy, the content of nickel is 35-95 wt %, preferably 50-90 wt %.

3. The pretreatment method according to technical solution C1 or C2, wherein, the amorphous alloy further contains one or more metals of aluminum, iron, chromium, copper, zinc, molybdenum and cobalt.

4. The pretreatment method according to any of technical solutions C1-C3, wherein, based on the total weight of amorphous alloy, the content of nickel is 35-95 wt %, the total content of other metals is 5-65 wt %, Preferably, based on the total weight of amorphous alloy, the content of nickel is 50-90 wt %, the total content of other metals is 10-50 wt %.

5. The pretreatment method according to any of technical solutions C1-C3, wherein, the amorphous alloy contains nickel and aluminum, and one or more metals of iron, chromium, copper, zinc, molybdenum and cobalt, preferably at least one of a combination of chromium and iron, a combination of chromium and copper, a combination of chromium and molybdenum, a combination of chromium and cobalt;

Based on the total weight of amorphous alloy, the content of nickel is 35-95 wt %, the content of aluminum is 0.5-40 wt %, the total content of one or more metals of iron, chromium, copper, zinc, molybdenum and cobalt is 0.1-50 wt %;

Preferably, based on the total weight of amorphous alloy, the content of nickel is 50-90 wt %, the content of aluminum is 1-30 wt %, the total content of one or more metals of iron, chromium, copper, zinc, molybdenum and cobalt is 1-40 wt %;

More preferably, based on the total weight of amorphous alloy, the content of nickel is 50-90 wt %, the content of aluminum is 1-15 wt %, the total content of one or more metals of iron, chromium, copper, zinc, molybdenum and cobalt is 5-40 wt %.

6. The pretreatment method according to any of technical solutions C1-C5, wherein in the X-ray diffraction pattern of the adsorbent, a diffuse peak appears at 45±1° in the 2θ angle range of 20-80°.

7. The pretreatment method according to any of technical solutions C1-C6, wherein the condition for contacting the 2-alkylanthraquinone working fluid with the adsorbent in alkali liquor includes: the temperature is 10-200° C., preferably 25-170° C., the pressure is 0-3 MPa, preferably 0-2 MPa;

Preferably, the number of contact is 1-5, more preferably 2-4, the time for each contact is 0.01-24 hours, more preferably 0.5-8 hours;

Preferably, the contact is performed under stirring, the rotation speed of the stirring is 500-2000 rpm, more preferably 800-1200 rpm.

8. The pretreatment method according to any of technical solutions C1-C7, wherein based on the weight of the 2-alkylanthraquinone working fluid, the used amount of the adsorbent is 0.01-40 wt %, preferably 1-10 wt %.

9. The pretreatment method according to any of technical solutions C1-C7, wherein the alkali in the alkali liquor is an inorganic base, the inorganic base is at least one of sodium hydroxide, potassium hydroxide, sodium carbonate and potassium carbonate, preferably sodium hydroxide, the alkali liquor is preferably an aqueous alkali solution;

The volume ratio of the alkali liquor to the 2-alkylanthraquinone working fluid is 0.1-10, preferably 0.5-2.

10. The pretreatment method according to technical solution C1, wherein the washing condition is such one that the pH value of the washed 2-alkylanthraquinone working fluid is neutral, preferably, the washing comprises acid washing and water washing in sequence.

11. The pretreatment method according to technical solution C10, wherein the acid used for acid washing is an inorganic acid, the inorganic acid is at least one of sulfuric acid, hydrochloric acid, nitric acid and phosphoric acid, preferably phosphoric acid, the acid is used in the form of acid liquor, preferably an aqueous acid solution;

The condition for acid washing comprises: the temperature is 5-100° C., preferably 20-60° C., the pressure is 0-1 MPa, preferably 0-0.5 MPa;

The volume ratio of the acid liquor to the 2-alkylanthraquinone working fluid is 0.1-10, preferably 0.5-2;

The number of acid washing is 1-5, preferably 2-4, the time for each acid washing is 0.01-24 hours, preferably 0.5-8 hours;

Preferably, the acid washing is performed under stirring, the rotation speed of the stirring is 500-2000 rpm, more preferably 800-1200 rpm.

12. The pretreatment method according to technical solution C10, wherein the condition for water washing comprises: the pressure is 0-1 MPa, preferably 0-0.5 MPa, the temperature is 5-100° C., preferably 20-60° C.;

The volume ratio of water to the 2-alkylanthraquinone working fluid is 0.1-10, preferably 0.5-2;

The number of water washing is 1-5, preferably 2-4, the time for each water washing is 0.01-24 hours, preferably 0.5-8 hours;

Preferably, the water washing is performed under stirring, the rotation speed of the stirring is 500-2000 rpm, more preferably 800-1200 rpm.

13. A method for producing hydrogen peroxide, which comprises the steps of hydrogenating, oxidizing and extracting a 2-alkylanthraquinone working fluid, and is characterized in that the method also comprises a step of pretreating the 2-alkylanthraquinone working fluid before hydrogenation, wherein the pretreatment method is the method according to any one of technical solutions C1-C12.

It should be noted that each of the above four groups of technical solutions A-D can be arbitrarily combined with one or more other technical solutions as long as the combination can be implemented.

BRIEF DESCRIPTION OF THE DRAWINGS

The drawings are used to provide a further understanding of the present invention, and constitute a part of the specification, together with the following specific embodiments to explain the present invention, but do not constitute a limitation to the present invention.

DETAILED DESCRIPTION OF THE INVENTION

Figure 1:
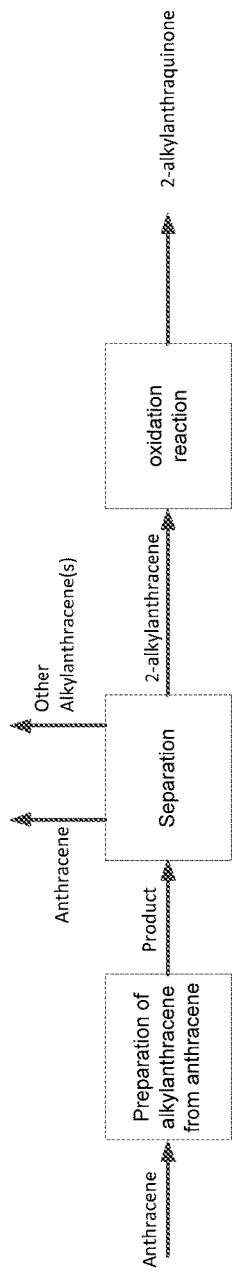
FIG. 1 is a flow diagram of the method for the preparation of 2-alkylanthraquinone by catalytic oxidation of 2-alkylanthracene obtained by separation from the reaction of anthracene according to one embodiment provided by the present invention.

The endpoints of the ranges and any values disclosed herein are not limited to the precise range or value, and these ranges or values should be understood to include values close to these ranges or values. For the numerical range, any two endpoint values of the ranges, or any one endpoint value of the ranges and any one individual point value, or any two individual point values can be combined with each other to form one or more new numerical ranges, and these numerical ranges should be regarded as being specifically disclosed herein.

In the present invention, 2-alkylanthraquinone means 2-alkyl-9,10-anthraquinone, hereinafter referred to as 2-alkylanthraquinone.

Herein, the pressures specified in the section describing the vacuum distillation are expressed in absolute pressure in KPa, and the pressures specified in the other sections are expressed in gauge pressure in MPa, in the absence of statements to the contrary.

According to one aspect of the present invention, the method for preparing 2-alkylanthraquinone by catalytic oxidation of 2-alkylanthracene obtained by alkylation of anthracene comprises the following steps:
  (1) contacting anthracene and an alkylation reagent under an alkylation condition and in the presence of an alkylation reaction solvent and a catalyst to perform the alkylation reaction to produce a reaction product containing alkylanthracenes, the alkylation reaction solvent is a combination of solvent A having a dielectric constant of 1-10 at 20° C. and solvent B having a dielectric constant of more than 10 to 50 or less at 20° C.;
  (2) separating the reaction product containing alkylanthracene obtained from step (1), the separation method comprising: the separation of anthracene by melting crystallization and the separation of 2-alkylanthracene by distillation;
  (3) contacting 2-alkylanthracene obtained from step (2) with an oxidizing agent under an oxidizing condition and in the presence of an oxidation reaction solvent and a catalyst to perform an oxidation reaction, the oxidizing agent is hydrogen peroxide, the catalyst is one or more of alkaline earth metal oxide, alkaline earth metal hydroxide, oxygen-containing compound of transition metal and oxygen-containing compound of lanthanide series metal.

According to another aspect of the present invention, the method for preparing 2-alkylanthraquinone by catalytic oxidation of 2-alkylanthracene obtained by separation from the reaction of anthracene comprises the following steps:
  (1) preparing a reaction product containing alkylanthracenes from anthracene;
  (2) separating the reaction product containing alkylanthracenes obtained from step (1), the separation method comprising: the separation of anthracene by melting crystallization and the separation of 2-alkylanthracene by distillation;
  (3) contacting 2-alkylanthracene obtained in step (2) with an oxidizing agent under an oxidizing condition and in the presence of an oxidation reaction solvent and a catalyst to perform the oxidation reaction, the oxidizing agent is tert-butyl hydroperoxide, the catalyst contains a support and an active component on the support, the active component is one or more of elements under the group VA and transition metals.

(1) Alkylation Reaction

According to the present invention, the feedstock anthracene can be reacted to produce a reaction product containing alkylanthracene. The method of producing the reaction product containing alkylanthracene from anthracene can be any single reaction or a combination of multiple reactions to introduce an alkyl group into an anthracene ring to produce alkylanthracene. The substances containing a structure of anthracene ring in the reaction product obtained from step (1) comprise the residual anthracene, 2-alkylanthracene and a product of a series of alkylanthracenes. It is well known to those skilled in the art that, due to the difference in reaction methods, if the feedstock anthracene cannot be completely converted, the reaction product may contain the residual anthracene. If the alkylanthracene is not a single substance, the alkylanthracene may also be a mixture. Therefore, the reaction product containing alkylanthracene prepared from the feedstock anthracene usually contains anthracene, 2-alkylanthracene and the product of a series of alkylanthracenes.

According to the present invention, as shown in FIG. 1, the method for producing the reaction product containing alkylanthracene from anthracene in step (1) includes: contacting anthracene with an alkylating agent under an alkylation condition and in the presence of an alkylation reaction solvent and a catalyst to perform the alkylation reaction.

According to the present invention, the mode of contacting anthracene with an alkylation reagent and a catalyst can be any of various modes capable of producing alkylanthracene by the alkylation of anthracene. Preferably, in order to achieve an sufficient reaction, the contacting manner is to contact a feedstock liquor containing anthracene, catalyst and alkylation reaction solvent with an alkylation reagent to perform the alkylation reaction.

According to the present invention, in step (1), under an alkylation condition and in the presence of an alkylation reaction solvent and a catalyst, the manner of contacting anthracene with an alkylating agent is not particularly limited. Preferably, in order to ensure that the alkylation reaction is better performed, anthracene and the catalyst and the alkylation reaction solvent are firstly formulated into a feedstock liquor of anthracene-catalyst-alkylation reaction solvent, and then the alkylation reagent is added to perform the alkylation reaction.

Preferably, the temperature at which the feedstock liquor of anthracene-catalyst-alkylation reaction solvent is formulated is 100-250° C., more preferably 120-200° C.

According to the present invention, the alkylation reaction solvent is an inert organic solvent capable of dissolving anthracene.

In the alkylation reaction in step (1), solvent A having a dielectric constant of 1-10 at 20° C. can be used alone.

In the alkylation reaction in step (1), a solvent combination of solvent A having a dielectric constant of 1-10 at 20° C. and solvent B having a dielectric constant of more than 10 to 50 or less at 20° C. can also be used as the alkylation reaction solvent, so that the property of the solvent can be controlled in a targeted manner, the dissolution of the feedstock anthracene can be enhanced in virtue of solvation and therefore the alkylation reaction can be promoted and the anthracene conversion can be improved. According to the present invention, the alkylation reaction solvent in step (1) can achieve the object of the present invention as long as it is a combination of solvent A and solvent B, but in order to better achieve the object of the present invention of enhancing the alkylation reaction by controlling the properties of the solvent, the volume ratio of solvent A to solvent B is 0.01-100, more preferably 0.1-10.

More specifically, the alkylation reaction solvent A can be one or more of $C_6$ or more, preferably $C_6$-$C_{12}$ alkane, cycloalkane and aromatic hydrocarbon; wherein the aromatic hydrocarbon is substituted or unsubstituted, preferably one or more of mono- or poly-substituted benzenes, more preferably one or more of poly-substituted benzenes, the substituent is preferably one or more of $C_1$-$C_4$ alkyl and halogen. Further preferably, the solvent A is one or more of polyalkyl substituted benzenes, most preferably, the solvent A is one or more of 1,3,5-trimethylbenzene, 1,2,3,5-tetramethylbenzene, 1,2,3,4-tetramethylbenzene and 2,3,5,6-tetramethylbenzene.

The alkylation reaction solvent B is N-alkyl substituted amide, wherein the number of alkyl substituent is 1-2, each alkyl substituent is independently $C_1$-$C_4$ alkyl; more preferably, the solvent B is one or more of N,N-dimethylformamide, N,N-dimethylacetamide and N,N-dimethylpropionamide, most preferably, the solvent B is N,N-dimethylformamide.

In the present invention, the N-alkyl substituted amide means

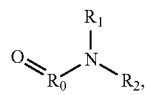

wherein $R_0$ is $C_{1-4}$ alkylene, $R_1$ and $R_2$ are each independently selected from hydrogen and $C_{1-4}$ alkyl, preferably at least one of $R_1$ and $R_2$ is not hydrogen.

The amount of the alkylation reaction solvent is only required to ensure that anthracene can be sufficiently dissolved so as to achieve the effect of providing a good reaction medium. Therefore, the amount of the alkylation reaction solvent used in step (1) is not particularly limited. Preferably, based on the total weight of anthracene and alkylation reaction solvent, the content of anthracene is 5-60 wt %, preferably 8-50 wt %.

Unless otherwise indicated, the condition and method of the anthracene alkylation reaction may be selected in a conventional manner in the art.

According to the present invention, the alkylation reagent can be any alkylation reagent known to those skilled in the art that can introduce an alkyl group into an anthracene ring to produce an alkylanthracene, for example, the alkylation reagent can be one or more of alkenes, alcohols, halohydrocarbons, and ethers having 2 to 8 carbon atoms, preferably one or more of alkenes, alcohols, halohydrocarbons, and ethers having 4 to 6 carbon atoms, and more preferably mono-olefins having 4 to 6 carbon atoms.

According to the present invention, the alkylation reagent is used in an amount to achieve the introduction of the alkyl group into the anthracene ring to produce the alkylanthracene, preferably the mole ratio of anthracene to alkylation reagent is 0.2:1-20:1 more preferably 0.5:1-5:1.

According to the present invention, in step (1), the alkylation reaction condition generally includes: the reaction temperature can be 100-250° C., preferably 120-200° C.; the reaction time can be 0.01-48 hours, preferably 0.5-24 hours; the reaction pressure can be 0-1 MPa, preferably 0.05-0.5 MPa.

According to the present invention, in step (1), in order to make the alkylation reaction easier to proceed, the alkylation reaction is performed in the presence of a catalyst.

In particular, the catalyst can be any form and kind of acid catalyst capable of catalyzing the alkylation reaction of anthracene, for example, the catalyst is a liquid acid or a solid acid catalyst.

For example, the catalyst is one or more of liquid acids, preferably methanesulfonic acid and/or paratoluenesulfonic acid.

The solid acid includes zeolite and zeolite-like catalysts, clays, metal oxides and metal mixed oxides, supported acids, sulfated oxides, layered transition metal oxides, metal salts, heteropolyacids and resin catalysts. The solid acid is preferably selected from one or more of zeolite catalysts, supported acids, heteropolyacids and resin catalysts. For example, for zeolite-like catalysts, the solid acid catalyst contains an active molecular sieve and a binder. The content of the active molecular sieve and the content of the binder in the solid acid catalyst are not particularly limited, so long as the content of the binder is enough to make the active molecular sieve into shape with a certain strength, and the content of the active molecular sieve is enough to realize the catalysis. Generally, based on the total weight of the solid acid catalyst, the content of the active molecular sieve may be 1-99 wt %, and the content of binder can be 1-99 wt %. From the viewpoint of balancing the strength and the catalytic activity of the catalyst, the content of the active molecular sieve is 30-95 wt % and the content of the binder is 5-70 wt % based on the total weight of the solid acid catalyst. The kinds of the active molecular sieve and the binder are not particularly limited, and may be conventionally selected in the art. Generally, the active molecular sieve may be selected from one or more of X zeolite, Y zeolite, beta zeolite, ZSM-5 zeolite, SAPO zeolite and a mesoporous molecular sieve, preferably Y zeolite. The binder may be an inorganic binder or an organic binder, preferably an inorganic binder. The inorganic binder may be a refractory inorganic oxide and/or silicate, for example the binder may be one or more of alumina, silica, titania, magnesia, zirconia, thoria, beryllia and clay, more preferably alumina. In the present invention, the shape of the solid acid catalyst is not particularly limited, and may be conventionally selected in the art. For example, it may be spherical, strip-shaped, annular, clover-shaped, and the like. Spherical particles are preferred for convenience of packing, and the particle diameter of the spherical particles may be in the range of 10-1000 μm, more preferably 20-300 μm.

The used amount of the catalyst can also refer to the conventional amount in the art, and based on the total weight of the feedstock liquor containing anthracene, the alkylation reaction solvent, and the catalyst, the content of the catalyst may be 0.01-50 wt %, preferably 0.5-30 wt %.

According to the present invention, in the step (1), the process for producing alkylanthracene from feedstock anthracene requires the use of a catalyst, and the catalyst after the reaction may be separated after the step (1) and before the step (2) by a separation method which is conventional in the art, depending on the nature of the catalyst.

(2) Separation of Anthracene and 2-Alkylanthracene

As can be seen from the physical property analysis, the boiling point of anthracene is 340° C., and the alkylanthracene product and the anthracene homologue have a difference in boiling points therebetween, and the product separation can be achieved by the vacuum distillation technique. But the technical difficulty is that the melting point of anthracene is as high as 215° C., the separation of anthracene with high solidifying point by adopting the vacuum distillation technology alone has a large operation difficulty, once the heat preservation problems appear in pipelines, the blockage phenomenon is easy to occur, and the continuous and stable operation of the process is seriously influenced. In addition, anthracene is very easily sublimed, and sublimation temperature is difficult to control, and the chance for the blockage of pipelines will remarkably increase. Therefore, it is impractical to use solely vacuum distillation techniques to achieve separation of the anthracene-alkylanthracene product.

Therefore, the inventors of the present invention propose to separate anthracene and an alkylanthracene product by a melting crystallization-distillation separation method. Alkylanthracene damages the high regularity of anthracene ring structure due to the side chain substituent group, so that the melting point of the alkylanthracene product is obviously reduced, for example, the melting point of the low carbon number-alkylanthracene product (1<the carbon number of alkyl side chain of alkylanthracene j1<8) is in the range of 130-190° C., the melting point of the high carbon number-alkylanthracene product (7<the carbon number of alkyl side chain of alkylanthracene j2<18) is in the range of 150-190° C., the melting points are obviously lower than the melting point 215° C. of anthracene, and a large melting point difference exists between alkylanthracene and anthracene. Therefore, the inventors of the present invention propose that firstly, the melting crystallization technology is adopted, anthracene which has the highest melting point and is most difficult to realize the separation operation is separated and removed in a crystallization mode, and then, one-step or multi-step vacuum distillation technology is adopted to realize a further separation of the alkylanthracene mixture with higher boiling points according to the difference of boiling points.

Based on this, according to the present invention, the reaction product containing the alkylanthracene obtained from step (1) contains anthracene and the product of a series of alkylanthracenes containing 2-alkylanthracene; the step (2) comprises:

(2-2) heating the reaction product containing the alkylanthracene obtained from step (1) to a molten state, cooling and crystallizing, separating to obtain an anthracene crystal and a stream of the product of a series of alkylanthracenes containing 2-alkylanthracene, heating the anthracene crystal to sweat, and separating the sweating liquor and the anthracene crystal;

(2-3) separating 2-alkylanthracene from the product of a series of alkylanthracenes containing 2-alkylanthracene by one-step distillation or multiple-step distillation.

Figure 4:
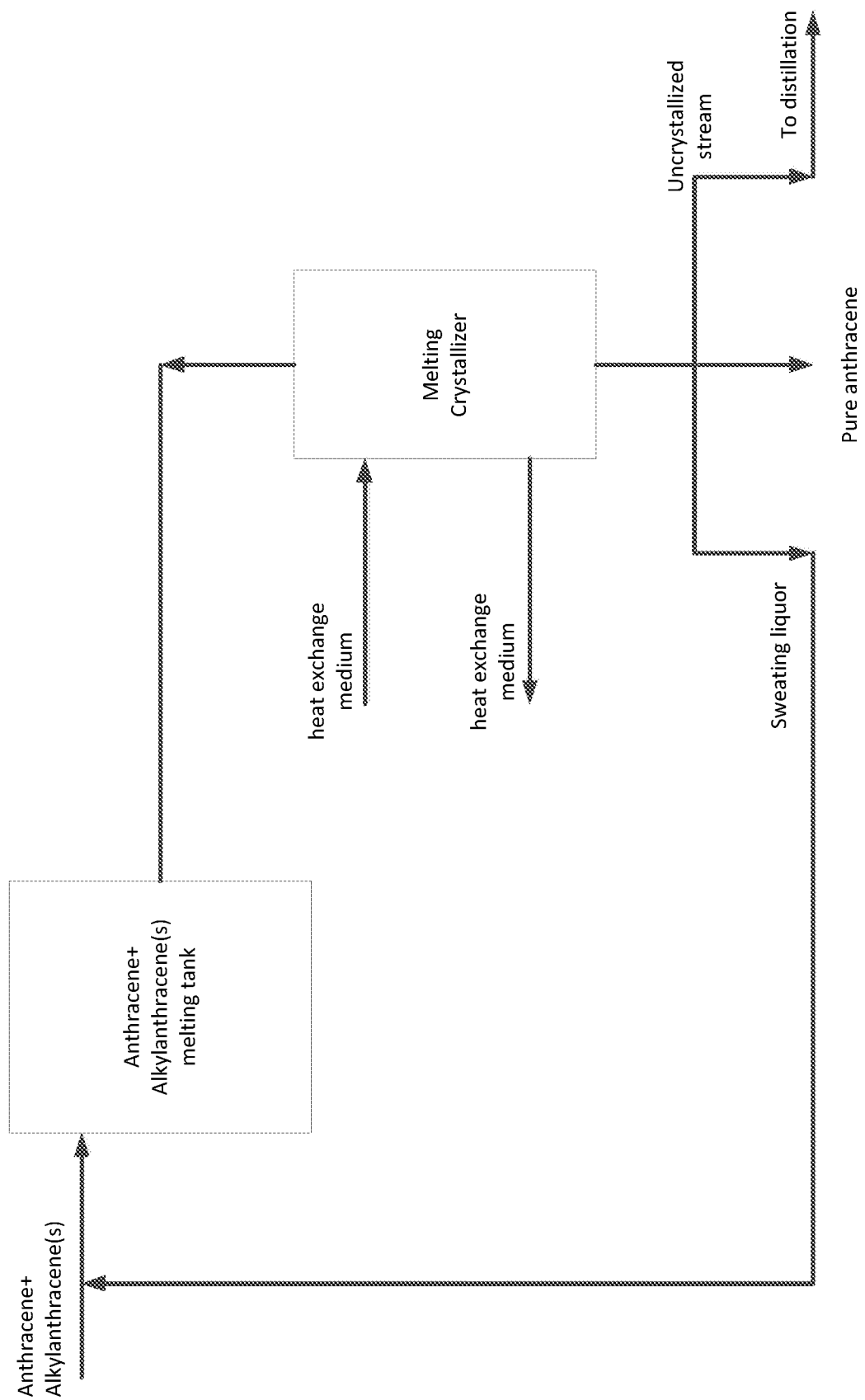
FIG. 4 is a flow diagram for the step of melting crystallization in the technology including the separation of the anthracene alkylation product, the melting crystallization, and the vacuum distillation provided by the present invention.

According to one embodiment of the present invention, as shown in FIG. 4, the melting crystallization step can be performed in a melting crystallization system in which the separation by crystallization of anthracene from the reaction product mixture can be accomplished. The melting crystallization system includes an intermediate melting tank and a melting crystallizer. The molten product containing anthracene and the product of a series of alkylanthracenes that is heated and melted in the distillation column is sent to the intermediate melting tank and then introduced into the melting crystallizer. The apparatus used for implementing the melting crystallization process is a melting crystallizer, the crystallization process can be a lamellar crystallization or a suspension crystallization, and the operation mode can be a batch operation or a continuous operation, but the present invention is not limited thereto. However, the lamellar crystallization in the mode of batch operation is more preferable. The temperature increase and decrease in the melting crystallizer is achieved by introducing a heat exchange medium into the melting crystallizer. After the heated and molten materials enter the melting crystallizer, the temperature is reduced through a cooling medium, so that anthracene with a higher melting point is crystallized and separated out, and further the separation of anthracene and the product of a series of alkylanthracenes is realized.

According to the present invention, in step (2-2) of the melting crystallization, in order to better realize the separation by crystallization of anthracene, the melting temperature is controlled to be 200-270° C., preferably 210-250° C.

According to the present invention, the melting crystallization process essentially comprises three steps of cooling and crystallization, sweating, and preferably heating and remelting of the anthracene crystals.

According to the present invention, the temperature for cooling and crystallization may be 180-210° C., preferably 190-200° C. In order to better realize the separation by crystallization of anthracene, the temperature reduction rate for cooling and crystallization can be 0.1-10° C./h, preferably 0.5-5° C./h, and the time for cooling and crystallization, namely the crystal growth time, can be controlled to be 1-5 hours, preferably 1.5-4 hours.

According to the present invention, in order to increase the crystallization rate, in the cooling and crystallization process, it is also preferable to include a step of adding anthracene as crystal seeds, which may be added in an amount depending on the specific cooling and crystallization process, and it is further preferable to add anthracene as crystal seeds in an amount of 0.1-10 wt %, more preferably 0.2-5 wt %, based on the mass of the molten mixture.

According to the present invention, in order to further improve the purity of the anthracene crystal, it is necessary to further perform an operation of sweating the anthracene crystal. After the crystal layer is formed, the temperature of the crystal layer is slowly approached to the equilibrium temperature by controlling the temperature-increasing rate of the crystal layer. Due to the uneven distribution of impurities in the crystal layer, the local crystals with more impurities have lower melting points and will be firstly melted and separated from the crystal in a sweating mode. By controlling the sweating rate and the sweating degree of the process, the purity and separation accuracy of the crystal can be significantly improved, and then the complete separation of anthracene and alkylanthracene products can be achieved, which reduces the pressure on the subsequent separation and purification of alkylanthracene products.

According to the present invention, in the melting crystallization step, the temperature-rise rate for sweating the anthracene crystal is controlled to 0.1-8° C./hour, preferably 0.2-4° C./hour from the viewpoint of further improving the purity and separation accuracy of the crystal. The temperature to which the temperature is increased and at which the sweating is terminated cannot melt the crystallized anthracene crystals. Therefore, the temperature to which the temperature is increased and at which the sweating is terminated must be lower than the melting temperature of the anthracene crystals. Preferably, the temperature to which the temperature is increased and at which the sweating is terminated is lower than or equal to 210° C., more preferably, the temperature is increased to a temperature 5-15° C. higher than the cooling crystallization temperature, and the sweating is terminated when the temperature is below 210° C. Following the above-mentioned principle for the temperature at which the sweating is terminated, the temperature at which the sweating is terminated can be 190-210° C., more preferably 195-205° C. In order to further increase the purity of the anthracene crystal, the amount of sweating may also be controlled, preferably, the amount of sweating is 5-40%, more preferably 10-30% by weight of the crystal.

According to the present invention, in order to further improve the separation accuracy, the collected sweating liquor is recycled, namely the sweating liquor is recycled to the melting crystallization step: the sweating liquor and the reaction product containing alkylanthracene, namely, the mixture containing anthracene and the product of a series of alkylanthracenes are heated to be molten, and then cooled and crystallized.

According to the present invention, after the completion of the sweating, the temperature of the separated anthracene crystal can further be increased to 215° C. or higher, and the anthracene crystal is collected and reused after being completely melted into liquid.

After melting and crystallization according to the method of the present invention, the collected uncrystallized stream is a stream of the product of a series of alkylanthracenes containing 2-alkylanthracene, which is mainly composed of the product of a series of alkylanthracenes (i.e., substantially free of anthracen).

According to the present invention, the boiling point of the product of a series of alkylanthracenes containing 2-alkylanthracene is higher than that of anthracene (340° C.), therefore the distillation technology is needed in order to further achieve the purpose of separating the product of a series of alkylanthracenes. Therefore, 2-alkylanthracene can be separated from the product of a series of alkylanthracenes containing 2-alkylanthracene by one-step distillation or multiple-step distillation.

According to the present invention, in step (2-3), if the product of a series of alkylanthracenes containing 2-alkylanthracene is a mixture of two substances, or a mixture of three or more substances, and the boiling point of 2-alkylanthracene is the lowest or the highest; then a one-step distillation separation of the 2-alkylanthracene is performed. In step (2-3), if the product of a series of alkylanthracenes containing 2-alkylanthracene is a mixture of three or more substances, and the boiling point of the 2-alkylanthracene is between the boiling points of a substance with the highest boiling point and a substance with the lowest boiling point in the mixture; then a multiple-step distillation is performed.

Figure 2:
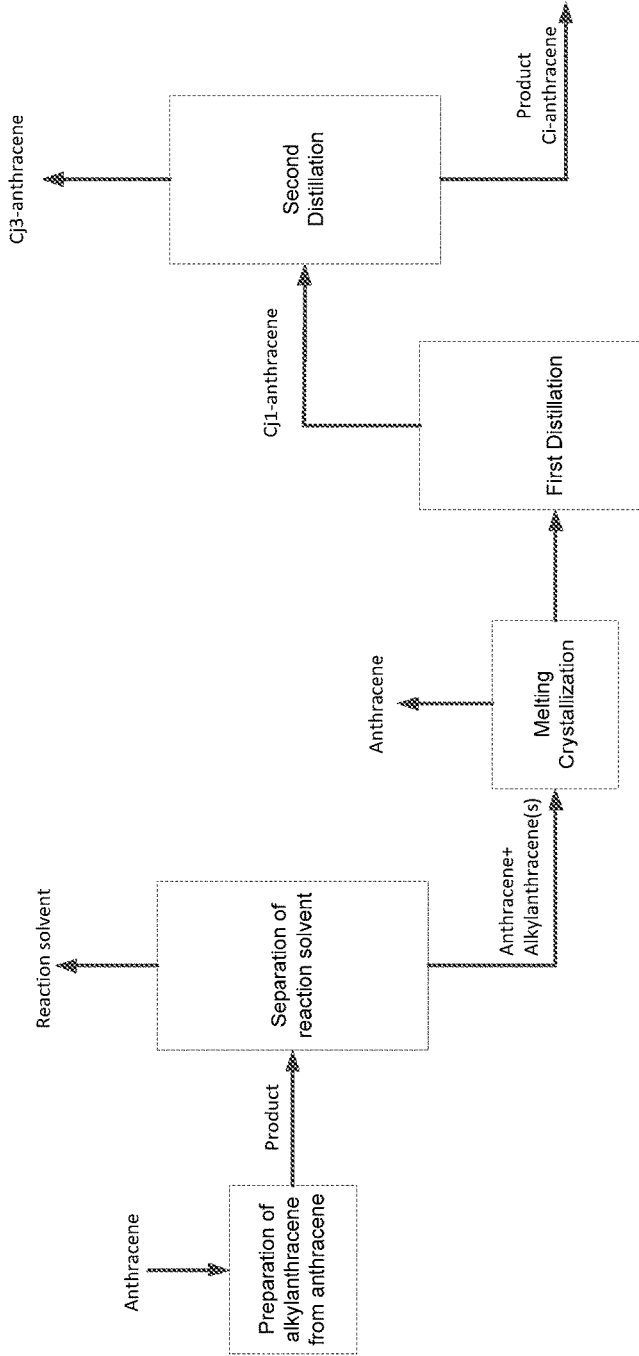
FIG. 2 shows a coupling technology including the separation of the anthracene alkylation product, the melting crystallization, and the multiple-step vacuum distillation according to an embodiment provided by the present invention.

According to an embodiment of the present invention, in step (2-3), the multiple-step distillation method comprises:

Mode 1: as shown in FIG. 2, a stream of the product of a series of alkylanthracenes containing 2-alkylanthracene is subjected to a first distillation separation to produce a distillate containing light component Cj1-anthracene and a bottom product containing heavy component Cj2-anthracene; the distillate containing light component Cj1-anthracene is subjected to a second distillation to produce a distillate containing light component Cj3-anthracene and a bottom product containing target product Ci-anthracene;

Wherein the light component Cj1-anthracene is a mixture of a plurality of alkylanthracenes, and for each alkylanthracene, the total carbon number j1 of alkyl side chain is $1 \leq j1 \leq i+1$; the heavy component Cj2-anthracene is one alkylanthracene or a mixture of a plurality of alkylanthracenes, and for each alkylanthracene, the total carbon number j2 of alkyl side chain is $i < j2 < 41$; the light component Cj3-anthracene is one alkylanthracene or a mixture of a plurality of alkylanthracenes, and for each alkylanthracene, the total carbon number j3 of alkyl side chain is $1 \leq j3 < i$;

Wherein in the target product Ci-anthracene, i represents the total carbon number of alkyl side chain, i=an integer of 4-7, the substitution position is at 2 position, namely 2-alkylanthracene, and the total carbon number of alkyl side chain is 4-7; j1, j2 and j3 are all integers.

The condition of the first distillation includes: the top pressure of the distillation column is 0.01-20 KPa, the temperature at the column bottom is 180-360° C., the theoretical plate number is 20-90, the top reflux ratio is 0.5-8. More preferably, the top pressure of the column is 0.1-10 KPa, the temperature at the column bottom is 210-340° C., the theoretical plate number is 30-75, the top reflux ratio is 1-7. Further preferably, the top pressure of the distillation column is 0.5-2 KPa, the temperature at the column bottom is 220-320, e.g. 260-320° C., the theoretical plate number is 40-75, the top reflux ratio is 1-3. Under this operating condition, the bottom product is mainly Cj2-anthracene product (the total carbon number j2 of alkyl side chain is an integer of i<j2<41), and the column top distillate is Cj1-anthracene product (the total carbon number j1 of alkyl side chain is an integer of 1<j1<i+1).

The condition of the second distillation includes: the top pressure of the distillation column is 0.01-20 KPa, the temperature at the column bottom is 180-330° C., the theoretical plate number is 20-90, the top reflux ratio is 0.5-8. More preferably, the top pressure of the column is 0.1-10 KPa, the temperature at the column bottom is 200-310° C., the theoretical plate number is 30-75, the top reflux ratio is 1-7. Further preferably, the top pressure of the distillation column is 0.5-2 KPa, the temperature at the column bottom is 220-305° C., e.g., 220-300° C., the theoretical plate number is 40-75, the top reflux ratio is 1-5. Under this operating condition, the bottom product is the target product Ci-anthracene (2-alkylanthracene, the total carbon number of alkyl side chain is 4-7), and the column top distillate is the Cj3-anthracene product (the total carbon number j3 of alkyl side chain is an integer 1<j3<i).

Figure 3:
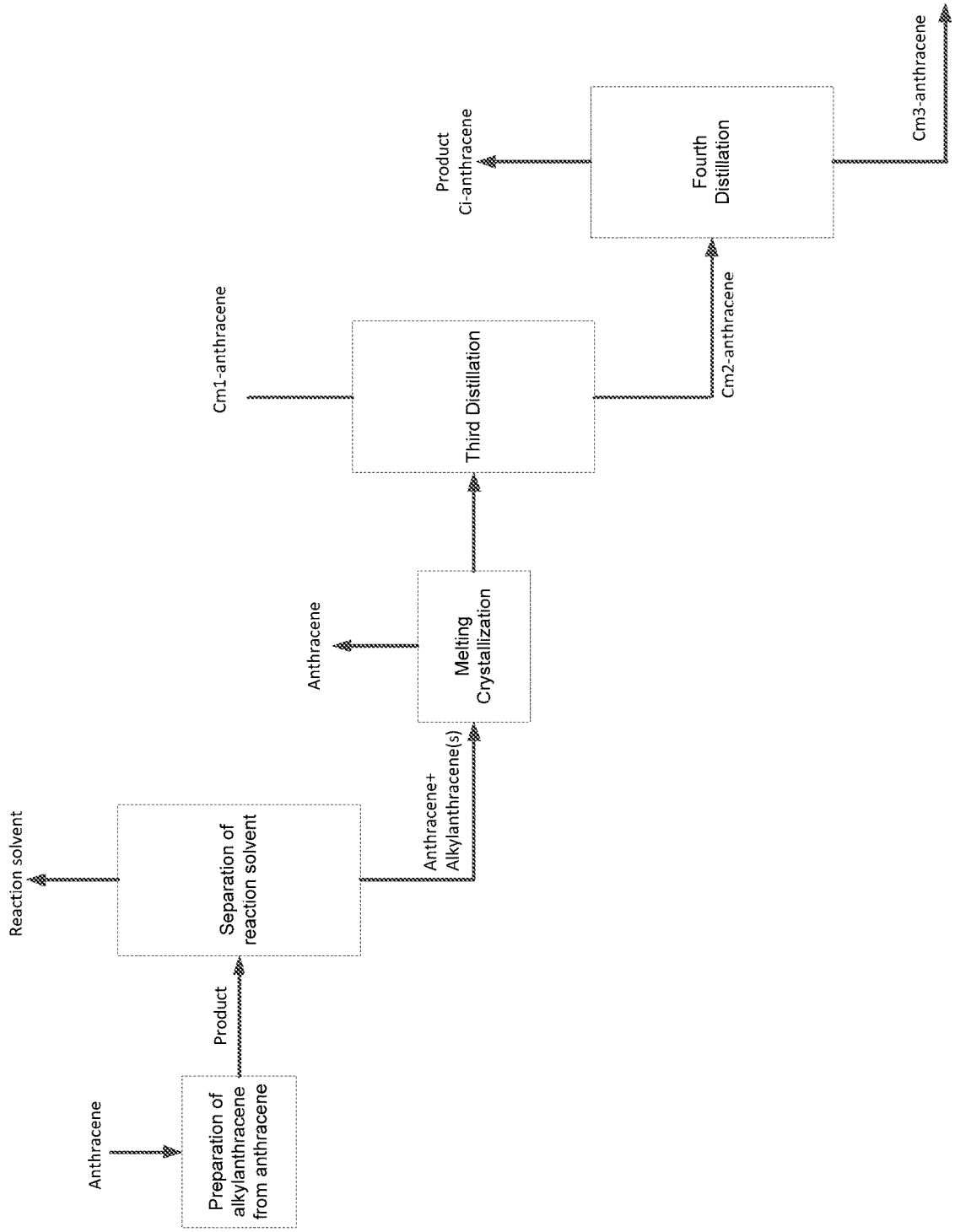
FIG. 3 shows a coupling technology including the separation of the anthracene alkylation product, the melting crystallization, and the multiple-step vacuum distillation according to an embodiment provided by the present invention.

For example, as shown in FIG. 2, the alkylanthracene mixture is a continuous homolog mixture of C2-anthracene to C20-anthracene, while C5-anthracene is the target product to be separated. Through the first distillation, light components including C2-anthracene to C5-anthracene are obtained at the column top, and heavy components including C6-anthracene to C20-anthracene are obtained at the column bottom. The mixture of C2-anthracene to C5-anthracene is subjected to a second distillation, light components obtained at the column top comprise a mixture of C2-anthracene to C4-anthracene, and the target product C5-anthracene is obtained at the column bottom.

or,

Mode 2: as shown in FIG. 3, a stream of the product of a series of alkylanthracenes containing 2-alkylanthracene is subjected to a third distillation to produce a distillate containing light component Cm1-anthracene and a bottom product containing heavy component Cm2-anthracene; the bottom product containing heavy component Cm2-anthracene is subjected to a fourth distillation to produce a distillate containing target product Ci-anthracene and a bottom product containing heavy component Cm3-anthracene;

Wherein the light component Cm1-anthracene is an alkylanthracene or a mixture of a plurality of alkylanthracenes, and for each alkylanthracene, the total carbon number m1 of alkyl side chain is 1<m1<i; wherein the heavy component Cm2-anthracene is a mixture of a plurality of alkylanthracenes, and for each alkylanthracene, the total carbon number m2 of alkyl side chain is i−1<m2<41;

Wherein the heavy component Cm3-anthracene is one alkylanthracene or a mixture of a plurality of alkylanthracenes, and for each alkylanthracene, the total carbon number m3 of alkyl side chain is i<m3<41;

Wherein in the target product Ci-anthracene, i represents the total carbon number of alkyl side chain, i=an integer of 4-7, the substitution position is at 2 position, namely 2-alkylanthracene, and the total carbon number of alkyl side chain is 4-7; m1, m2 and m3 are all integers.

The condition of the third distillation includes: the top pressure of the distillation column is 0.01-20 KPa, the temperature at the column bottom is 180-360° C., the theoretical plate number is 20-90, the top reflux ratio is 0.5-8. More preferably, the top pressure of the column is 0.1-10 KPa, the temperature at the column bottom is 210-340° C., the theoretical plate number is 30-75, the top reflux ratio is 1-7. Further preferably, the top pressure of the distillation column is 0.5-2 KPa, the temperature at the column bottom is 220-320° C., e.g., 260-320° C., the theoretical plate number is 40-75, the top reflux ratio is 1-3. Under this operating condition, the bottom product is mainly Cm2-anthracene product (the total carbon number m2 of alkyl side chain is an integer of i−1<m2<41), and the column top distillate is Cm1-anthracene product (the total carbon number m1 of alkyl side chain is an integer of 1<m1<i).

The condition of the fourth distillation includes: the top pressure of the distillation column is 0.01-20 KPa, the temperature at the column bottom is 180-330° C., the theoretical plate number is 20-90, the top reflux ratio is 0.5-8. More preferably, the top pressure of the column is 0.1-10 KPa, the temperature at the column bottom is 200-310° C., the theoretical plate number is 30-75, the top reflux ratio is 1-7. Further preferably, the top pressure of the distillation column is 0.5-2 KPa, the temperature at the column bottom is 220-305° C., e.g., 220-300° C., the theoretical plate number is 40-75, the top reflux ratio is 1-5. Under this operating condition, the column top distillate is the target product Ci-anthracene (2-alkylanthracene, the total carbon number of alkyl side chain is 4-7), and the bottom product is the Cm3-anthracene product (the total carbon number m3 of alkyl side chain is an integer i<m3<41).

For example, as shown in FIG. 3, the alkylanthracene mixture is a continuous homolog mixture of C2-anthracene to C30-anthracene, while C5-anthracene is the target product to be separated. Through the third distillation, light components including C2-anthracene to C4-anthracene are obtained at the column top, and heavy components including C5-anthracene to C20-anthracene are obtained at the column bottom. The mixture of C5-anthracene to C20-anthracene is subjected to a fourth distillation, the target product C5-anthracene is obtained at the column top, heavy components obtained at the column bottom comprise a mixture of C6-anthracene to C20-anthracene.

According to the present invention, the specific operating conditions of each vacuum distillation in the multiple-step vacuum distillation may be appropriately selected within the operating temperature and pressure ranges according to the different distillation ranges of the column top distillate and the bottom product in each vacuum distillation process.

According to the present invention, various vacuum distillation apparatuses known in the art may be employed in the multiple-step vacuum distillation, for example, a sieve-tray column or a packed column, more preferably a packed column.

According to the present invention, depending on the process and the operating condition of the reaction in step (1), other substances having a boiling point lower than that of anthracene, such as reaction solvents and other by-products (e.g., the residual alkylating agent after the alkylation reaction), which are referred to as light components, may be brought in or generated. Therefore, the reaction product containing the alkylanthracene obtained from step (1) further contains a reaction solvent. A step (2-1) of separating the reaction solvent before the separation of anthracene by melting crystallization and the separation of 2-alkylanthracene by distillation, is further concluded. The method for separating the solvent can adopt a separation method conventional in the art. Preferably, the reaction solvent in the mixed liquor containing the alkylanthracene product is separated by atmospheric distillation from the viewpoint of further improving the separation efficiency and simplifying the operation. According to an embodiment of the present invention, the separation method comprises (2-1)

the reaction product containing the alkylanthracene obtained from step (1) is subjected to distillation in a distillation column to produce a distillate containing the reaction solvent, and a bottom product containing anthracene and the product of a series of alkylanthracenes containing 2-alkylanthracene. In addition, the separated reaction solvent may be recycled or collected for disposal according to the requirements of the reaction. In addition, other by-products can also be separated before the anthracene-alkylanthracene separation, and can be removed by conventional separation methods, such as distillation.

Preferably, in step (2-1), the distillation condition comprises: the temperature at the bottom of distillation column is 100-300° C., preferably 150-200° C., the top pressure of the distillation column is normal pressure.

(3) Catalytic Oxidation to Produce Alkylanthraquinone

According to the present invention, the intermediate product 2-alkylanthracene obtained by separation can be reacted to produce 2-alkylanthraquinone. The method for preparing 2-alkylanthraquinone from 2-alkylanthracene obtained from step (2) can be any single reaction or a combination reaction of multiple steps to obtain 2-alkylanthraquinone from 2-alkylanthracene.

According to the present invention, in step (3), the method for preparing 2-alkylanthraquinone from 2-alkylanthracene obtained from step (2) is to prepare 2-alkylanthraquinone by oxidation reaction of 2-alkylanthracene. Specifically, in step (3), the method for preparing 2-alkylanthraquinone from 2-alkylanthracene obtained in step (2) comprises contacting 2-alkylanthracene obtained in step (2) with an oxidizing agent under an oxidizing condition and in the presence of an oxidation reaction solvent and a catalyst to perform the oxidation reaction, the oxidizing agent is hydrogen peroxide, the catalyst is one or more of alkaline earth metal oxide, alkaline earth metal hydroxide, oxygen-containing compound of transition metal and oxygen-containing compound of lanthanide series metal; or the oxidizing agent is tert-butyl hydroperoxide, the catalyst contains a support and an active component on the support, the active component is one or more of elements under the group VA and transition metals.

(3.1) Hydrogen Peroxide as Oxidizing Agent

According to the present invention, in step (3), the oxidant (hydrogen peroxide) and the catalyst (one or more of alkaline earth metal oxide, alkaline earth metal hydroxide, oxygen-containing compound of transition metal and oxygen-containing compound of lanthanide series metal) are used in combination, which can effectively realize the conversion of 2-alkylanthracene. Moreover, the 2-alkylanthracene catalytic oxidation system is simple and efficient, the difficulty in the catalyst separation and recovery is low, and there is no corrosiveness, which reduces the equipment investment and the post-treatment cost of the oxidation waste liquor.

Preferably, in step (3), the catalyst is one or more of oxygen-containing compound(s) of group IIA, group IVB, group VB, group VIB, group VIIB, group VIII metals and lanthanide series metal. For example, the group IIA-based can be oxygen-containing compound(s) of Be, Mg, Ca, Sr, and Ba, the group IVB-based can be oxygen-containing compound(s) of Ti and Zr, the group VB-based can be oxygen-containing compound(s) of V, Nb and Ta, the group VIB-based can be oxygen-containing compound(s) of Cr, Mo and W, the group VIIB-based can be oxygen-containing compound(s) of Mn and Re, the group VIII-based can be oxygen-containing compound(s) of Fe, Co, Ni, Ru, Rh, Pd, Os, Ir and Pt, the lanthanide series-based can be oxygen-containing compound(s) of La, Ce, Pr, Nd, Pm, Sm, Eu, Gd, Tb, Dy, Ho, Er, Tm, Yb and Lu. More preferably, the catalyst is one or more of oxygen-containing compound(s) of Ca, Ba, Ti, Zr, V, Cr, Mo, W, Mn, Ru, Co, Ni, La and Ce. Most preferably, the catalyst is selected from one or more of calcium hydroxide, barium hydroxide, titanium (IV) oxycompound, including metatitanic acid, zirconium (IV) oxycompound, including zirconium dioxide and zirconyl nitrate, vanadium (V) oxycompound, including sodium metavanadate, chromium (VI) oxycompound, including potassium chromate and chromium sesquioxide, molybdenum (VI) oxycompound, including sodium molybdate, ammonium molybdate and molybdenum trioxide, tungsten (VI) oxycompound, including sodium tungstate, manganese (III) and manganese (IV) oxycompound, including manganese sesquioxide and manganese dioxide, ruthenium (VI) oxycompound, including ruthenium dioxide, cobalt (III) oxycompound, including cobaltic oxide, nickel (II) and nickel (III) oxycompound, including nickel oxide and nickel sesquioxide, lanthanum (III) oxycompound, including lanthanum nitrate and lanthanum sesquioxide, cerium (IV) oxycompound, including cerium dioxide.

According to the present invention, in step (3), for convenience of operation, hydrogen peroxide as the oxidizing agent is preferably used in the form of an aqueous hydrogen peroxide solution, the concentration of which is not particularly limited and may be selected by reference to the conventional ones in the art.

According to the present invention, the amounts of the oxidant and the catalyst used in step (3) can be selected from a wide range, and preferably, in order to better achieve the object of the present invention, the mole ratio of the oxidant to the catalyst is 0.01:1-100:1, and more preferably 0.1:1-30:1.

According to the present invention, the manner of contacting 2-alkylanthracene with an oxidizing agent and a catalyst can be any manner that can realize the oxidation of 2-alkylanthracene to obtain 2-alkylanthraquinone.

Preferably, in order to achieve an sufficient reaction, the contacting manner is to contact a feedstock liquor containing 2-alkylanthracene, a catalyst and an oxidation reaction solvent with an oxidizing agent to perform the oxidation reaction.

According to the present invention, in step (3), the condition and the method of the oxidation reaction may be selected in a conventional manner in the art, except for the combination of the above-mentioned hydrogen peroxide oxidizing agent and the specific catalyst.

According to the present invention, in step (3), the oxidizing agent is used in such an amount to achieve the oxidization of 2-alkylanthracene to produce 2-alkylanthraquinone, preferably the mole ratio of the oxidizing agent to 2-alkylanthracene is 0.01:1-100:1, more preferably 1:1-50:1.

According to the present invention, in step (3), the oxidation reaction condition generally includes: the reaction temperature can be 10-200° C., preferably 20-200° C.; the reaction time can be 0.01-48 hours, preferably 0.5-24 hours; the reaction pressure can be 0-1 MPa, preferably 0-0.5 MPa.

According to the present invention, in step (3), the oxidation reaction solvent is an inert organic solvent capable of dissolving 2-alkylanthracene.

According to an embodiment of the present invention, the oxidation reaction solvent is a solvent having a dielectric constant of greater than 2.8 at 20° C., preferably, the oxidation reaction solvent is a solvent having a dielectric constant of greater than 2.8 to less than or equal to 50 at 20° C.; more preferably, the oxidation reaction solvent is one or more of fatty alcohol with carbon number of 1-4, tetrahydrofuran, acetone, N-alkyl substituted amide and N-alkyl pyrrolidone. Wherein, the fatty alcohol with carbon number of 1-4 can be a monohydric alcohol or a polyhydric alcohol. For the N-alkyl substituted amide, the number of alkyl substituent is 1-2, each alkyl substituent is independently $C_1$-$C_4$ alkyl. Most preferably, the oxidation reaction solvent is one or more of methanol, tert-butyl alcohol, acetone, N,N-dimethylformamide, N,N-dimethylacetamide, N,N-dimethylpropionamide, N-methylpyrrolidone and N-ethylpyrrolidone. The amount of the oxidation reaction solvent is only required to ensure that the 2-alkylanthracene can be sufficiently dissolved so as to achieve the effect of providing a good reaction medium. Preferably, based on the total weight of 2-alkylanthracene and the oxidation reaction solvent, the content of 2-alkylanthracene is 0.1-80 wt %, preferably 5-50 wt %.

According to another embodiment of the present invention, the oxidation reaction solvent is solvent A having a dielectric constant of 1-10 at 20° C.

According to another embodiment of the present invention, the oxidation reaction solvent is a combination of solvent A having a dielectric constant of 1-10 at 20° C. and solvent B having a dielectric constant of more than 10 to 50 or less at 20° C. The inventors of the present invention found that in the oxidation reaction of step (3), a combination solvent of solvent A having a dielectric constant of 1-10 at 20° C. and solvent B having a dielectric constant of more than 10 to 50 or less at 20° C. is used as the oxidation reaction solvent, which can control the properties of the solvent in a targeted manner, strengthen the dissolution of 2-alkylanthracene in virtue of solvation, promote the oxidation reaction, and improve the conversion of 2-alkylanthracene.

According to the present invention, preferably, the solvent A is one or more of $C_6$ or more, more preferably $C_6$-$C_{12}$ alkane, cycloalkane and aromatic hydrocarbon; wherein, the aromatic hydrocarbon is substituted or unsubstituted, preferably one or more of mono- or poly-substituted benzenes, more preferably one or more of poly-substituted benzenes, the substituent is preferably one or more of $C_1$-$C_4$ alkyl and halogen. Further preferably, the solvent A is one or more of polyalkyl substituted benzenes, most preferably, the solvent A is one or more of 1,3,5-trimethylbenzene, 1,2,3,5-tetramethylbenzene, 1,2,3,4-tetramethylbenzene and 2,3,5,6-tetramethylbenzene.

According to the present invention, preferably, the solvent B is N-alkyl substituted amide, wherein, the number of alkyl substituent is 1-2, each alkyl substituent is independently $C_1$-$C_4$ alkyl; more preferably, the solvent B is one or more of N,N-dimethylformamide, N,N-dimethylacetamide and N,N-dimethylpropionamide, most preferably, the solvent B is N,N-dimethylformamide.

In the present invention, the N-alkyl substituted amide means

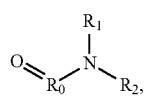

wherein $R_0$ is $C_{1-4}$ alkylene, $R_1$ and $R_2$ are each independently selected from hydrogen and $C_{1-4}$ alkyl, preferably at least one of $R_1$ and $R_2$ is not hydrogen.

According to the present invention, in step (3), in order to better achieve the aim of the invention of enhancing the oxidation reaction by regulating the properties of the solvent, the volume ratio of the solvent A to the solvent B is 0.01-100, and more preferably 0.05-10.

(3.2) Tert-Butyl Hydroperoxide as Oxidizing Agent

According to the present invention, in step (3), the oxidizing agent tert-butyl hydroperoxide and the supported catalyst are used in combination, so that the feedstock conversion can be improved and the selectivity is good, the difficulty in separating and recovering the catalyst is low, the technological conditions are mild, the corrosion of materials does not exist, and the equipment investment can be reduced.

Preferably, in step (3), the active component in the catalyst is one or more of elements under the group VA and metals under the group VB, the group VIB and the group VIII, preferably a combination of an element under the group VA and at least one metal of the group VB, the group VIB and the group VIII. Specifically, the element under the group VA can be selected from N, P, As, Sb and Bi, the group VB metal can be selected from V, Nb, and Ta, the group VIB metal can be selected from Cr, Mo, and W, the group VIII metal can be selected from Fe, Co, Ni, Ru, Rh, Pd, Os, Ir, and Pt. Further preferably, the active component is one or more of P, V, Cr, Mo, Fe and Co, most preferably a combination of P and at least one of V, Cr, Mo, Fe and Co. The support in the catalyst may be selected from one or more of thermotolerant inorganic oxides and molecular sieves, preferably thermotolerant inorganic oxide. The thermotolerant inorganic oxide can be one or more of silicon dioxide, magnesium oxide and silica-alumina composite oxide, wherein in the silica-alumina composite oxide, as oxide, the content of $SiO_2$ can be 0.01-70 wt %, preferably 5-40 wt %, the content of $Al_2O_3$ can be 30-99.9 wt %, preferably 60-95 wt %.

The contents of the support and the active component in the catalyst are not particularly limited, and the content of the support and the content of the active component in the catalyst are subject to the catalytic effect. Further preferably, based on the weight of the support in the catalyst and based on the element content, the content of the active component is 0.01-40 wt %, more preferably 0.1-30 wt %. Further preferably, in order to further improve the catalytic performance of the catalyst, the active component in the catalyst is a combination of an element under the group VA and a transition metal, based on the element content, the mass ratio of the transition metal to the element under the group VA is 1-20:1.

According to the present invention, the catalyst may be prepared by an impregnation method which is conventional in the art, and may be prepared by, for example, a dry impregnation method (i.e., an isometric impregnation method) or by, for example, an incipient wetness impregnation method. The specific process includes: impregnating a support with a solution containing a soluble compound of active component, drying and calcining the impregnated support, the soluble compound of active component is soluble compound(s) of one or more of elements under the group VA and transition metals.

Among them, when there are multiple elements in the active component, the method of impregnating the support with the solution containing the soluble compound of the active component can be performed in the following two ways: (1) the solutions of soluble compounds of multiple active components are made into a mixed solution and then the support is impregnated; (2) the support can also be impregnated in sequence with each solution of soluble compounds of various active components (the order of impregnating the support with solutions of soluble compounds of various elements can be arbitrarily selected).

According to the present invention, the condition for impregnating the support with a solution containing the soluble compound of active component generally comprises the temperature and the time. The impregnation temperature may be 0-100° C., preferably 20-80° C., and the impregnation time may be appropriately selected according to the dispersion degree of the soluble compound of active component. Preferably, the impregnation time is 4-24 hours, more preferably 6-12 hours. Furthermore, the amount of the solvent in the solution containing the soluble compound of active component is such that on one hand the compound of the active ingredient can be sufficiently soluble in the solvent and on the other hand the sufficient dispersion of the support should be ensured, preferably the amount of the solvent in the solution containing the soluble compound of active component is 0.05-10 mL, preferably 0.1-5 mL, based on 1 g of the support. According to the present invention, the solvent in the solution may be selected from one or more of water, methanol, ethanol, isopropanol, butanol and pentanol.

According to the present invention, the amounts of the support and the soluble compound of the active component can be selected in a wide range. Preferably, the support and the soluble compound of the active component are used in such amounts that based on the weight of the support in the catalyst, the content of the active component as element(s) is 0.01-40 wt %, more preferably 0.1-30 wt %. According to the present invention, the soluble compound of active component is soluble compound(s) of one or more of elements under the group VA and metals under the group VB, the group VIB and the group VIII. Further preferably, the soluble compound of active component is soluble compound(s) of one or more elements of P, V, Cr, Mo, Fe and Co. In order to further improve the catalytic performance of the catalyst, the soluble compound of active component is preferably a combination of a soluble compound of an element under the group VA and a soluble compound of at least one metal of the group VB, the group VIB and the group VIII. Most preferably, it is a combination of P and a soluble compound of at least one element of V, Cr, Mo, Fe and Co.

According to the present invention, the soluble compound is generally a water-soluble compound, and specifically, for example, in the soluble compounds of P, V, Cr, Mo, Fe and Co, the soluble compound of the metal can be one or more of nitrate, chloride, ammonium salt and the like of the metal, and the soluble compound of the non-metal can be ammonium phosphate, ammonium metavanadate, ammonium chromate, ammonium molybdate, iron nitrate and cobalt nitrate; preferably one or more selected from the group consisting of ammonium phosphate, ammonium metavanadate, ammonium chromate, ammonium molybdate, iron nitrate and cobalt nitrate.

According to the present invention, the condition for drying the support after impregnating the support with the solution containing the soluble compound of active component may be any conventional drying condition, for example, the drying temperature may be 90-125° C. and the drying time may be 1-12 hours.

According to the present invention, the condition for calcining the dried support, which is obtained by impregnating the support with the solution containing the soluble compound of active component and drying the impregnated support, generally includes the calcining temperature and the calcining time, wherein the calcining temperature may be 300-700° C., and the calcining time may be selected depending on the calcining temperature and may generally be 2-6 hours. The calcining is generally performed in an air atmosphere, which includes both flowing atmospheres and stationary atmospheres.

According to the present invention, in step (3), the used amounts of the oxidizing agent and the catalyst can be selected in wide ranges, preferably based on the total weight of catalyst and oxidation reaction solvent, the content of catalyst is 0.01-50 wt %, preferably 0.5-30 wt %.

According to the present invention, the manner of contacting 2-alkylanthracene with an oxidizing agent and a catalyst can be any manner that can realize the oxidation of 2-alkylanthracene to obtain 2-alkylanthraquinone. Preferably, in order to achieve an sufficient reaction, the contacting manner is to contact a feedstock liquor containing 2-alkylanthracene, a catalyst and an oxidation reaction solvent with an oxidizing agent to perform the oxidation reaction.

According to the present invention, in step (3), the condition and the method of the oxidation reaction may be selected in a conventional manner in the art, except for the combination of the above-mentioned tert-butyl hydroperoxide oxidizing agent and the specific catalyst.

According to the present invention, in step (3), the oxidizing agent is used in such an amount to achieve the oxidization of 2-alkylanthracene to produce 2-alkylanthraquinone, preferably the mole ratio of the oxidizing agent to 2-alkylanthracene is 0.01:1-100:1, more preferably 1:1-50:1.

According to the present invention, in step (3), the oxidation reaction condition generally includes: the reaction temperature can be 10-150° C., preferably 20-100° C.; the reaction time can be 0.01-48 hours, preferably 0.5-24 hours; the reaction pressure can be 0-1 MPa, preferably 0-0.5 MPa.

According to the present invention, in step (3), the oxidation reaction solvent is an inert organic solvent capable of dissolving 2-alkylanthracene. The oxidation reaction solvent can be a polar organic solvent or a nonpolar organic solvent. The oxidation reaction solvent can be N-alkyl substituted amide, wherein the number of alkyl substituent is 1-2, each alkyl substituent is $C_1$-$C_4$ alkyl independently, for example, one or more of N,N-dimethylformamide, N,N-dimethylacetamide and N,N-dimethylpropionamide. In the present invention, the N-alkyl substituted amide means

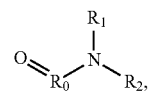

wherein $R_0$ is $C_{1-4}$ alkylene, $R_1$ and $R_2$ are each independently selected from hydrogen and $C_{1-4}$ alkyl, preferably at least one of $R_1$ and $R_2$ is not hydrogen. Preferably, the oxidation reaction solvent is a nonpolar organic solvent, the oxidation reaction solvent is one or more of $C_6$ or more, preferably $C_6$-$C_{12}$ alkane, cycloalkane and aromatic hydrocarbon; wherein, the aromatic hydrocarbon is substituted or unsubstituted, preferably one or more of mono- or polysubstituted benzenes. Wherein, the substituent is one or more of $C_1$-$C_4$ alkyl and halogen. Among others, when the substituent is $C_1$-$C_4$ alkyl, the oxidation reaction solvent can be one or more of 1,3,5-trimethylbenzene, 1,2,3,5-tetramethylbenzene, 1,2,3,4-tetramethylbenzene and 2,3,5,6-tetramethylbenzene. Further preferably, the oxidation reaction solvent is one or more of halogenated benzenes; most preferably, the oxidation reaction solvent is one or more of monochlorobenzene, dichlorobenzene, trichlorobenzene and tetrachlorobenzene. Among them, monochlorobenzene, dichlorobenzene, trichlorobenzene and tetrachlorobenzene include various stereoisomers thereof.

Regardless of the oxidizing agent, according to the present invention, in step (3), the amount of the oxidation reaction solvent is only required to ensure that the 2-alkylanthracene can be sufficiently dissolved so as to achieve the effect of providing a good reaction medium. Preferably, based on the total weight of 2-alkylanthracene and the oxidation reaction solvent, the content of 2-alkylanthracene is 0.1-80 wt %, preferably 5-50 wt %.

Regardless of the oxidizing agent, according to the present invention, in the step (3), the process for producing 2-alkylanthraquinone from 2-alkylanthracene requires the use of a catalyst, and the catalyst after the reaction may be separated with a separation method which is conventional in the art, depending on the nature of the catalyst. 2-alkylanthraquinone in the product is a target product, and if other substances including residual 2-alkylanthracene, solvent and the generated by-products exist, these other substances can be removed or purified respectively by a conventional separation method or a combined separation method according to the difference of the properties of the substances.

(4) Pretreatment of 2-Alkylanthraquinone Working Fluid and Production of Hydrogen Peroxide According to the present invention, the method for pretreating the 2-alkylanthraquinone working fluid comprises: contacting the 2-alkylanthraquinone working fluid with an adsorbent in alkali liquor to perform an adsorption desulfurization and impurity removal; separating the 2-alkylanthraquinone working fluid that has been subjected to the adsorption desulfurization and impurity removal; and washing, the adsorbent is an amorphous alloy, and the amorphous alloy contains nickel.

According to the present invention, each component in the amorphous alloy exists in an amorphous form. It can be verified by an XRD method. When the XRD pattern shows broadened diffraction peaks, it can be confirmed that the alloy has an amorphous form. Specifically, the amorphous alloy adsorbent used in the present invention takes nickel as the main active component, and in an X-ray diffraction pattern of the amorphous material, a diffuse peak appears at 45±1° in the 2θ angle range of 20-80°.

According to the present invention, the adsorbent is an amorphous alloy, and the amorphous alloy contains nickel, which is used as the main active component of the amorphous alloy, based on the total weight of amorphous alloy, the content of nickel can be 35-95 wt %, preferably 50-90 wt %.

Preferably, the amorphous alloy further contains one or more metals of aluminum, iron, chromium, copper, zinc, molybdenum and cobalt. Based on the total weight of amorphous alloy, the content of nickel is 35-95 wt %, the total content of other metals is 5-65 wt %, more preferably, based on the total weight of amorphous alloy, the content of nickel is 50-90 wt %, the total content of other metals is 10-50 wt %. Here, it is necessary to be noted that, if the other metal is one of aluminum, iron, chromium, copper, zinc, molybdenum and cobalt, the total content of other metals refers to the content of said one metal, and if the other metals are two or more of aluminum, iron, chromium, copper, zinc, molybdenum and cobalt, the total content of other metals refers to the total content of said two or more metals.

According to a specific embodiment of the present invention, from the perspective of further improving the effect of the adsorption desulfurization, the amorphous alloy contains nickel and aluminum, and one or more metals of iron, chromium, copper, zinc, molybdenum and cobalt, preferably at least one of a combination of chromium and iron, a combination of chromium and copper, a combination of chromium and molybdenum, a combination of chromium and cobalt; based on the total weight of amorphous alloy, the content of nickel is 35-95 wt %, the content of aluminum is 0.5-40 wt %, the total content of one or more metals of iron, chromium, copper, zinc, molybdenum and cobalt is 0.1-50 wt %, preferably, based on the total weight of amorphous alloy, the content of nickel is 50-90 wt %, the content of aluminum is 1-30 wt %, the total content of one or more metals of iron, chromium, copper, zinc, molybdenum and cobalt is 1-40 wt %, more preferably, based on the total weight of amorphous alloy, the content of nickel is 50-90 wt %, the content of aluminum is 1-15 wt %, the total content of one or more metals of iron, chromium, copper, zinc, molybdenum and cobalt is 5-40 wt %. Herein, the total weight of the amorphous alloy is 100 wt %.

According to the present invention, the preparation method of the amorphous alloy may be performed with reference to a conventional method in the art, except that the composition of the amorphous alloy is selected according to the present invention. Preferably, the preparation method of the amorphous alloy comprises the following steps: a mixture containing nickel and one or more other metals of aluminum, iron, chromium, copper, zinc, molybdenum and cobalt in the above-mentioned content ranges, preferably a mixture of nickel, aluminum and one or more other metals of iron, chromium, copper, zinc, molybdenum and cobalt in the above-mentioned content ranges is alloyed in vacuum at a temperature higher than their melting points, the alloy is rapidly quenched by vacuum quenching under a rapidly quenching condition that comprises the copper roll rotation speed is 600-1000 rpm (in an embodiment, preferably 800 rpm), and the spraying pressure is 0.05-0.1 MPa, a scale-shaped strip is formed, and the obtained alloy is ground to a particle diameter of 60-80 μm to produce a master alloy. The master alloy is subjected to a constant-temperature heat treatment in a reducing atmosphere, such as a hydrogen atmosphere, and the condition of the heat treatment comprises: the temperature is 500-800° C. (in an embodiment, preferably 600° C.), the constant-temperature treatment time is 2-5 hours (in an embodiment, preferably 3 hours). The heat-treated master alloy is subjected to an alkali treatment in an aqueous solution of an inorganic base, wherein the alkali-treatment temperature is 80-120° C. (in an embodiment, preferably 100° C.), the constant-temperature treatment time is 30 minutes to 2 hours (in an embodiment, preferably 1 hour), the inorganic base is typically sodium hydroxide, and the concentration of the aqueous sodium hydroxide solution is typically 20-30 wt %, and then washed to neutrality, i.e., pH=7, with distilled water, and then water is removed. Among others, the water-washing temperature is preferably equivalent to the temperature of the alkali treatment, and may be, for example, 80-100° C. (in an embodiment, preferably 80° C.). The method of removing water may refer to a conventional treatment method in the alloy art, for example, a washed master alloy is placed in benzene, an azeotropic distillation is performed at normal pressure, and then it may be stored in benzene for later use.

According to the present invention, the condition for contacting the 2-alkylanthraquinone working fluid with the adsorbent in alkali liquor usually includes: temperature, pressure and time. Wherein, the temperature range can be 10-200° C., preferably 25-170° C., the pressure and the time can be appropriately adjusted according to the contacting temperature, for example, the pressure range can be 0-3

MPa, preferably 0-2 MPa. The number of contacting the 2-alkylanthraquinone working fluid with an adsorbent in an alkali liquor is not particularly limited; and from the viewpoint of ensuring sufficient dissolution and precipitation of impurities in the 2-alkylanthraquinone working fluid and sufficient adsorption of sulfides, the number of contacting the 2-alkylanthraquinone working fluid with the adsorbent in the alkali liquor is 1-5, more preferably 2-4, and the time for each contact is 0.01-24 hours, preferably 0.5-8 hours. After each contacting for the alkali washing and desulfurization process, only the waste alkali liquor needs to be discharged, the adsorbent still continues to be used, and the waste alkali liquor and the adsorbent are discharged after the alkali washing and adsorption desulfurization is fully completed. Among others, the contact mode is preferably as follows: in the alkali liquor, the 2-alkylanthraquinone working fluid and the adsorbent are fully mixed, preferably, the contact is also performed under stirring, and the rotation speed of the stirring can be 500-2000 rpm, preferably 800-1200 rpm. According to the present invention, the alkali in the alkali liquor is usually an inorganic base which may be selected from at least one of sodium hydroxide, potassium hydroxide, sodium carbonate and potassium carbonate, preferably sodium hydroxide. The alkali liquor is usually an aqueous alkali solution, the concentration of the alkali liquor is not particularly limited and can be appropriately selected by those skilled in the art according to the solubility of different inorganic bases at different temperatures, as long as impurities can be sufficiently removed. According to an embodiment of the present invention, the concentration of the aqueous sodium hydroxide solution may be 0.1-70 wt %, preferably 1-50 wt %. Furthermore, the used amount of the alkali liquor is not particularly limited as long as it is guaranteed that impurities in 2-alkylanthraquinone working fluid are sufficiently dissolved and precipitated, and preferably the volume ratio of the alkali liquor to the 2-alkylanthraquinone working fluid is 0.1-10, more preferably 0.5-2.

According to the present invention, although the adsorption desulfurization of the working fluid can be achieved by bringing the 2-alkylanthraquinone working fluid into contact with the adsorbent in the alkali liquor, however, in order to be able to better achieve the object of the present invention, from the viewpoint of further improving the effect of the adsorption desulfurization, based on the weight of the 2-alkylanthraquinone working fluid, the used amount of the adsorbent is 0.01-40 wt %, preferably 1-10 wt %.

The present invention completes two processes of washing impurities (for example, impurities such as nonsubstituted anthraquinone and anthraquinone dimer) with the alkali liquor and adsorption desulfurization by contacting the 2-alkylanthraquinone working fluid with the adsorbent in the alkali liquor, and the coupling-treatment method of alkali washing and desulfurization greatly saves the cost and simplifies the process. In addition, the nickel-based amorphous alloy adopted by the present invention is stored in the alkali liquor, which can guarantee that the performance of the alloy can be more stable, and therefore the desulfurization and impurity removal effects of the 2-alkylanthraquinone working fluid can be further improved.

According to the present invention, in order to further remove impurities in the 2-alkylanthraquinone working fluid and make the pH value of the 2-alkylanthraquinone working fluid to be neutral, the method also comprises separating the 2-alkylanthraquinone working fluid that has been subjected to the adsorption desulfurization and impurity removal by alkali washing, and washing. Preferably, the washing comprises acid washing and water washing in sequence. After the adsorption desulfurization and impurity removal by alkali washing is completed, the separation of the 2-alkylanthraquinone working fluid that has been subjected to the adsorption desulfurization and impurity removal can be performed with those routine separation methods in the art, for example, the method for separating the alkali liquor and the the 2-alkylanthraquinone working fluid can be a method of centrifugation or a method of being allowed to stand and separated into layers, wherein the lower layer is the alkali liquor containing impurities, and the upper layer is the 2-alkylanthraquinone working fluid, and then the alkali liquor phase in the lower layer is removed. The method for separating the 2-alkylanthraquinone working fluid and the adsorbent may be a conventional solid-liquid separation method, such as filtration.

According to the present invention, the acid used in the acid washing and the acid washing condition are such that the alkali remained in the 2-alkylanthraquinone working fluid that has been subjected to the adsorption desulfurization and impurity removal by alkali washing is neutralized.

According to the present invention, the method of acid washing may refer to the conventional methods in the art. For example, the acid used for acid washing is usually an inorganic acid, the inorganic acid can be at least one of sulfuric acid, hydrochloric acid, nitric acid and phosphoric acid, preferably phosphoric acid. The acid is used in the form of acid liquor, and is usually an aqueous acid solution, and the concentration of the acid liquor is not particularly limited as long as it can sufficiently neutralize the alkali/alkali liquor remained in the 2-alkylanthraquinone working fluid. According to an embodiment of the present invention, the concentration of the aqueous phosphoric acid solution may be 0.1-83 wt %, preferably 0.5-20 wt %.

According to the present invention, the condition for acid washing can also refer to the conventional conditions in the art. For example, the condition for acid washing comprises: temperature and pressure. From the viewpoint of ensuring the sufficient neutralization of the alkali/alkali liquor remained in the 2-alkylanthraquinone working fluid, the acid washing temperature is 5-100° C., preferably 20-60° C. and the acid washing pressure can be adjusted appropriately according to the acid washing temperature, and is usually 0-1 MPa, preferably 0-0.5 MPa.

According to the present invention, the amount of acid liquor, the number of acid washing, and the time for each acid washing are not particularly limited, as long as it is guaranteed that the residual alkali/alkali liquor in the 2-alkylanthraquinone working fluid is sufficiently neutralized. Preferably, the volume ratio of the acid liquor to the 2-alkylanthraquinone working fluid is 0.1-10, more preferably 0.5-2. The number of acid washing is 1-5, preferably 2-4, and the time for each acid washing is generally 0.01-24 hours, preferably 0.5-8 hours.

According to the present invention, preferably, the acid washing is also performed under stirring. The rotation speed of the stirring can be 500-2000 rpm, preferably 800-1200 rpm.

According to the present invention, the method and the condition of water washing can be also refer to the conventional methods and conditions in the art, as long as it is guaranteed that the pH value of the 2-alkylanthraquinone working fluid is neutral.

According to the present invention, the condition for water washing generally includes temperature and pressure. From the viewpoint of sufficiently removing the residual acid liquor in the 2-alkylanthraquinone working fluid in order to ensure the pH value of the working fluid to be neutral, the water washing temperature is 5-100° C., preferably 20-60° C. and the water washing pressure can be adjusted appropriately according to the water washing temperature, and is usually 0-1 MPa, preferably 0-0.5 MPa. More preferably, it is identical to the condition for acid washing.

According to the present invention, the water amount of water washing, the number of water washing, and the time for each water washing are not particularly limited, as long as it is guaranteed that the residual acid/acid liquor in the 2-alkylanthraquinone working fluid is sufficiently diluted and removed. Preferably, the volume ratio of water to the 2-alkylanthraquinone working fluid is 0.1-10, more preferably 0.5-2. The number of water washing can be 1-5, preferably 2-4, the time for each water washing is generally 0.01-24 hours, preferably 0.5-8 hours.

According to the present invention, the water washing is preferably performed with stirring. The stirring speed can be 500-2000 rpm, preferably 800-1200 rpm.

In addition, the acid washing method and the water washing method can be realized by fully mixing acid liquor and water respectively with the 2-alkylanthraquinone working fluid, then being centrifuged or allowed to stand and separated into layers, wherein the lower layer is the acid liquor/water containing impurities, the upper layer is the 2-alkylanthraquinone working fluid, and then the washing liquid phase in the lower layer is removed to obtain a phase of the washed 2-alkylanthraquinone working fluid.

The 2-alkylanthraquinone working fluid in the pretreatment method provided by the present invention is not particularly limited, and its sulfur content (by weight of the elemental sulfur) can be 1-6 mg/kg and the sulfide therein mainly comprises an inorganic sulfide, e.g., sulfates, an organic sulfide, e.g. thiophenes, and the like.

The composition and the formulating method of the 2-alkylanthraquinone working fluid are not particularly limited by the present invention, and can refer to the conventional composition and the formulating method in the art. For example, the the 2-alkylanthraquinone working fluid is usually prepared by mixing 2-alkylanthraquinone with a mixed solvent composed of a nonpolar solvent and a polar solvent, wherein the content of 2-alkylanthraquinone in the mixed solvent is 100-300 g/L, the ratio of the nonpolar solvent to the polar solvent in the mixed solvent is generally 1-3:1, the nonpolar solvent can be selected from one or more of high boiling point mixed alkylbenzenes with a boiling range of 160-240° C., alkylbenzene with 9-10 carbon atoms and a mixture thereof, and the polar solvent can be selected from one or more of trioctyl phosphate, methylcyclohexyl acetate, tetrabutyl urea and diisobutyl methanol. Among others, the alkyl substituent of the 2-alkylanthraquinone is located at the 2-position of the anthraquinone ring, the carbon number of the alkyl substituent is not particularly limited, and may be, for example, $C_1$-$C_8$ alkyl, such as $C_1$-$C_6$ alkyl, or $C_1$-$C_5$ alkyl, and specific examples thereof may include, but are not limited to methyl, ethyl, n-propyl, isopropyl, n-butyl, sec-butyl, isobutyl, tert-butyl, n-pentyl and its isomers, n-hexyl and its isomers, n-heptyl and its isomers, n-octyl and its isomers, and the like.

The method for pretreating a 2-alkylanthraquinone working fluid according to the present invention will be described in detail with reference to FIG. 5.

Figure 5:
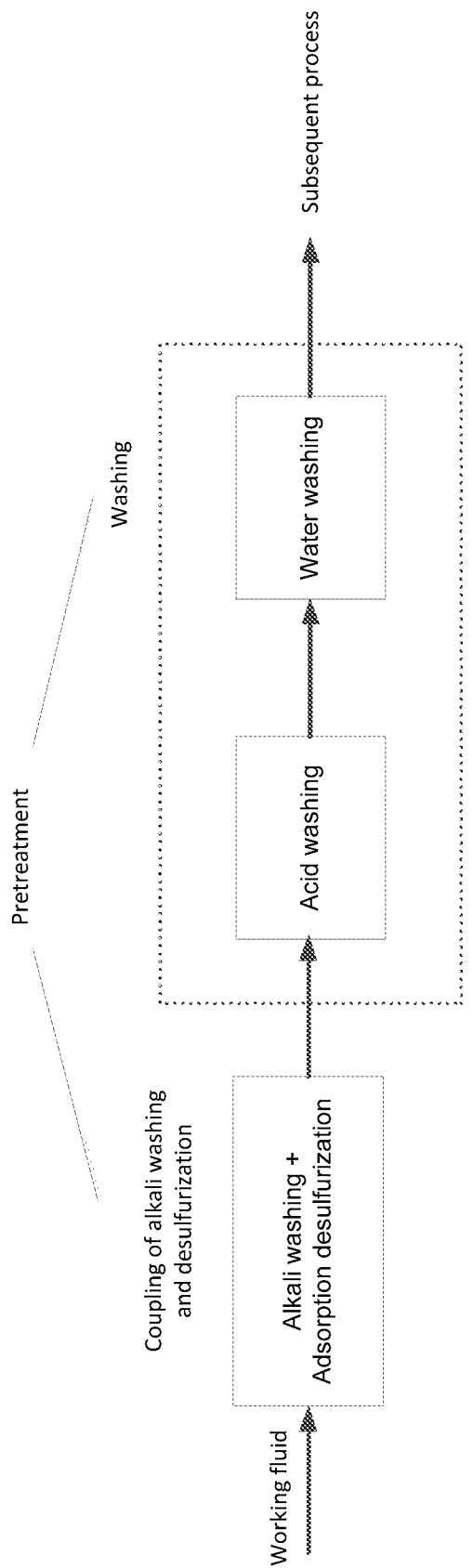
FIG. 5 is a process flow diagram of the pretreatment method of 2-alkylanthraquinone working fluid provided by the present invention.

The pretreatment process of the 2-alkylanthraquinone working fluid is performed as indicated in the technological process shown in FIG. 5. The pretreatment process of the 2-alkylanthraquinone working fluid specifically comprises the following steps: the 2-alkylanthraquinone working fluid is contacted with the alkali liquor and the adsorbent simultaneously to complete two processes of the alkali liquor washing and the adsorption desulfurization. According to the coupling treatment process of the alkali washing and the adsorption desulfurization, only the waste alkali liquor is discharged after each round of alkali washing and desulfurization. The mixed liquor is allowed to stand and separated into layers, the waste alkali liquor in the lower layer is discharged, and the adsorbent is still used. When the alkali washing and the desulfurization are completed according to the required number, the mixed liquor is allowed to stand and separated into layers. The waste alkali liquor in the lower layer is discharged, and then a solid-liquid separation, for example, filtering, is performed. After the adsorbent is discharged, the separated working fluid is sent to the acid washing process. The washing is performed according to the acid washing process of the present invention. After each acid washing process is completed, the mixed liquor is allowed to stand and separated into layers. The waste acid liquor in the lower layer is discharged. When the acid washing process is completed according to the required number, the mixed liquor is allowed to stand and separated into layers. The waste acid liquor in the lower layer is discharged, and the separated working fluid is sent to the water washing process. The washing is performed according to the water washing process of the present invention. After each water washing process is completed, the mixed liquor is allowed to stand and separated into layers. The water-washing waste liquor in the lower layer is discharged. When the water washing process is completed according to the required number and after the indexes of impurities and sulfur in the working fluid meet the requirements, the pretreatment process of the working fluid is finished, and the separated working fluid is sent to the subsequent process.

The present invention also provides a method for producing hydrogen peroxide, which comprises the steps of hydrogenating, oxidizing and extracting a 2-alkylanthraquinone working fluid, and is characterized in that the method also comprises a step of pretreating a fresh-formulated 2-alkylanthraquinone working fluid, said pretreating is the method for pretreating a 2-alkylanthraquinone working fluid provided by the present invention.

According to the invention, the method for producing hydrogen peroxide generally comprises the following steps:
(1) a hydrogenation step, contacting 2-alkylanthraquinone working fluid with hydrogen gas under a hydrogenation reaction condition in the presence of a catalyst to a hydrogenation liquor containing 2-alkylanthraquinone and hydrogenated 2-alkylanthraquinone;
(2) an oxidation step, contacting the hydrogenation liquor with oxygen gas or an oxygen-containing gas under an oxidation reaction condition to obtain an oxidation liquor containing hydrogen peroxide and 2-alkylanthraquinone;
(3) an extraction step, extracting hydrogen peroxide from the oxidization liquor to obtain an extract containing hydrogen peroxide and a raffinate.

In addition, a regeneration refining of the working fluid with a white clay bed or other processes before/after the hydrogenation can be included.

Before the hydrogenation of the fresh-formulated 2-alkylanthraquinone working fluid, a pretreatment of the 2-alkylanthraquinone working fluid with the method of the present invention is further included. Preferably, after the pretreatment of 2-alkylanthraquinone working fluid and before the hydrogenation, dehydration can be performed according to the conventional methods to ensure that the water content of the 2-alkylanthraquinone working fluid is less than 3000 mg/kg.

The method for producing hydrogen peroxide of the present invention is to perform a pretreatment with the pretreatment method of the present invention to achieve impurity removal and desulfurization before hydrogenating the fresh-formulated 2-alkylanthraquinone working fluid, thereby ensuring good activity and stability of the catalyst, so as to achieve the purpose of the present invention. Therefore, the specific operating conditions of the hydrogenation step, the oxidation step and the extraction step are not particularly limited, and these steps can be performed under the conventional conditions for the production of hydrogen peroxide by the anthraquinone method. Therefore, no more details will be given herein.

The present invention will be described in detail below through examples.

The composition data of materials were obtained by chromatographic analysis method.

The chromatographic analysis method: Agilent company 7890A; chromatographic column: DB-1 (50 m×0.25 mm×0.25 m). Sample inlet temperature: 330° C., sample size: 0.2 µL, the split ratio: 20:1, the carrier gas: nitrogen, the flow rate in constant flow mode: 0.7 mL/min, and the temperature programming: keeping the temperature at 110° C. for 10 min, then raising the temperature to 320° C. at the rate of 5° C./min, and keeping the temperature for 18 min. FID detector: temperature: 350° C., hydrogen flow rate: 35 mL/min, air flow: 350 mL/min, purge gas: nitrogen, and flow: 25 mL/min.

(I) In the alkylation reaction of step (1), the anthracene conversion was defined as $X_1$ (mol %), and the product selectivity calculated on a molar basis was defined as S (mol %). The mass fraction of each substance was expressed with its chromatographic peak area percentage, and combined with the molar mass to calculate the fraction W on a molar basis of each substance, (mol %).

AN represented anthracene, $C_{i\text{-}AN}$ represented 2-alkylanthracene, and $C_{j\text{-}AN}$ represented other alkylanthracenes. Anthracene conversion was calculated according to Equation 1 below:

$$X_1 = \frac{W_{Ci-AN} + \Sigma W_{Cj-AN}}{W_{AN} + W_{Ci-AN} + \Sigma W_{Cj-AN}} \quad (1)$$

2-alkylanthracene selectivity was calculated according to Equation 2 below:

$$S_{Ci-AN} = \frac{W_{Ci-AN}}{W_{Ci-AN} + \Sigma W_{Cj-AN}} \quad (2)$$

(II) in the separation of step (2), the purity B of a certain substance was the mass fraction of the substance, the purity of the separated anthracene was $B_1$, the purity of the separated 2-alkylanthracene was $B_2$, and the purity was obtained by calculation based on chromatographic analysis data. A mixture of anthracene and alkylanthracene to be separated was subjected to chromatographic analysis. An external standard analysis curve was prepared by using high-purity 2-alkylanthracene and mesitylene, and the content of 2-alkylanthracene in the mixture of anthracene and 2-alkylanthracene was quantitatively calculated and marked as $W_0$, g. The amount of 2-alkylanthracene actually obtained by separation according to the method proposed by the invention was denoted as $W_1$, g. The yield Y for the separation was calculated according to Equation 3 below.

$$Y = \frac{W_1}{W_0} \quad (3)$$

(III) in the oxidation reaction of step (3), the $C_{i\text{-}AN}$ conversion was defined as $X_2$, and the product selectivity S was calculated on a molar basis, (mol %). The mass fraction of each substance was expressed with its chromatographic peak area percentage, and combined with the molar mass to calculate the fraction W on a molar basis of each substance, (mol %).

$C_{i\text{-}AN}$ represented 2-alkylanthracene, $C_{i\text{-}AO}$ represented 2-alkylanthraquinone, and $C_{i\text{-}X}$ represented other by-products.

2-alkylanthracene conversion was calculated according to Equation 4 below:

$$X_2 = \frac{W_{Ci-AO} + \Sigma W_{Ci-X}}{W_{Ci-AN} + W_{Ci-AO} + \Sigma W_{Ci-X}} \quad (4)$$

2-alkylanthraquinone selectivity was calculated according to Equation 5 below:

$$S_{Ci-AO} = \frac{W_{Ci-AO}}{W_{Ci-AO} + \Sigma W_{Ci-X}} \quad (5)$$

The following Examples A1-A17 were provided to illustrate the preparation of 2-alkylanthraquinone provided by the present invention.

Example A1

(I) Alkylation Reaction.

2-pentylanthracene (i.e., 2-tert-pentylanthracene, the same applied hereinafter) was prepared by alkylation of anthracene and isopentene (i.e., 2-isopentene or 2-methyl-2-butene, the same applied hereinafter), wherein mesitylene and N,N-dimethylformamide were used as a combined solvent, the catalyst was a spherical catalyst containing an active Y zeolite, alumina was used as binder, based on the total weight of the catalyst, the content of the active Y zeolite was 82 wt %, the content of the binder was 18 wt %, and the average particle diameter of catalyst particles was 100 µm. 460 g of anthracene, 640 mL of mesitylene, 160 mL of N,N-dimethylformamide, and 205 g of the catalyst were charged into a 2 L stirring tank at room temperature. After sealing, the temperature was raised to 165° C. at the rotation speed of 1000 rpm, and the pressure was 0.3 MPa. 151 g of isopentene was added to the tank by means of a plunger pump at a feeding rate of 6.6 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

(II) Separation.

The alkylation reaction product was sent to an atmospheric distillation system, the temperature was raised to 165° C. under normal pressure, and light components such as the residual isopentene, mesitylene, N,N-dimethylformamide that had lower boiling points than anthracene could be successively separated. The remaining was a solid mixture of anthracene-alkylanthracene, the mixture was heated to 220° C., and maintained in a molten state and sent to a batch melting crystallization system; the melting crystallizer was a tubular crystallizer, and a cooling medium was introduced to start the cooling and crystallization. The temperature reduction rate was 0.5° C./h, the temperature for cooling and crystallizing was 200° C., the amount of anthracene added as crystal seed was 0.5 wt % of the mass of the molten mixture, and the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1 KPa, the temperature at the column bottom was 259° C., the theoretical plate number was 65, the top reflux ratio was 1.5. The column top distillate was subjected to a second vacuum distillation, wherein the column top pressure was 1 KPa, the temperature at the column bottom was 248° C., the theoretical plate number was 70, the top reflux ratio was 3. 2-pentylanthracene was collected as the bottom product.

(III) Oxidation Reaction.

2-pentylanthracene was subjected to a liquid phase oxidation to prepare 2-pentylanthraquinone. Into an 8 L glass tank were added 3000 mL of methanol, 150 g of 2-pentylanthracene, and 156 g of potassium chromate. The reaction was performed under normal pressure at 65° C., 1368 g of hydrogen peroxide solution (the content of hydrogen peroxide was 30 wt %) was added into the tank by a peristaltic pump, and the feeding rate was 2 g/min. After the feeding was completed, the reaction was continued for 2 hours while maintaining the conditions unchanged. After the reaction was completed, the stream in the tank was transferred into a 20 L glass stirring tank, 2000 mL of mesitylene and 3000 mL of deionized water were added for extraction and washing. After standing, the mesitylene phase containing 2-pentylanthraquinone was separated out as the upper layer, and distilled to obtain the final product 2-pentylanthraquinone. The aqueous phase in the lower layer was distilled, and after water was removed, the catalyst could be recovered.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Comparative Example A1

2-Alkylanthraquinone was prepared according to the method of Example A1, except that in step (I), mesitylene alone was used as the reaction solvent; in step (II), after removing by distillation light components with boiling points less than that of anthracene, anthracene was directly separated by vacuum distillation instead of melting crystallization. The distillation column for separating anthracene was a vacuum distillation system for the separation of anthracene, wherein the column top pressure was 8 KPa, the distillation temperature was 275° C., the theoretical plate number was 20, the top reflux ratio was 0.7. The column bottom distillates were sent to the first vacuum distillation and the second vacuum distillation under the same conditions as in Example A1.

In step (III), 3000 ml of methanol, 150 g of 2-pentylanthracene, and 307 g of 36 wt % hydrochloric acid were sent to a 5 L glass tank. The reaction was performed under normal pressure at 65° C., 342 g of hydrogen peroxide solution (the content of hydrogen peroxide was 30 wt %) was added into the tank by a peristaltic pump, and the feeding rate was 2 g/min. After the feeding was completed, the reaction was continued for 2 hours while maintaining the conditions unchanged. After the reaction was completed, the stream in the tank was transferred into a 20 L glass stirring tank, 2000 mL of mesitylene and 3000 mL of deionized water were added for extraction and washing. After standing, the mesitylene phase containing 2-pentylanthraquinone was separated out as the upper layer, and distilled to obtain the final product 2-pentylanthraquinone.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A2

2-Alkylanthraquinone was prepared according to the method of Example A1, except that in step (II), the temperature reduction rate was 5.0° C./h, the crystallizing temperature was 190° C., the amount of anthracene added as crystal seed comprised 4 wt % of the mass of the molten mixture, the time for crystal growth was controlled to 4 hours. After the crystallization was completed, the uncrystallized stream was discharged and sent to a vacuum distillation system. The crystal in the crystallizer was slowly heated and sweated, wherein the heating rate was 4° C./h, the sweating finishing temperature was 195° C., the sweating amount was 10 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1 KPa, the temperature at the column bottom was 259° C., the theoretical plate number was 65, the top reflux ratio was 1.5. The column top distillate was subjected to a second vacuum distillation, wherein the column top pressure was 1 KPa, the temperature at the column bottom was 248° C., the theoretical plate number was 70, the top reflux ratio was 3. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A3

2-Alkylanthraquinone was prepared according to the method of Example A1, except that in step (II), the uncrystallized alkylanthracene mixture was fed to a vacuum distillation system to perform a third vacuum distillation, wherein the top pressure was 1 KPa, the temperature at the column bottom was 252° C., the theoretical plate number was 65, the top reflux ratio was 1.5. The bottom distillate was subjected to a fourth vacuum distillation, wherein the top pressure was 1 KPa, the temperature at the column bottom was 264° C., the theoretical plate number was 70, and the top reflux ratio was 3. 2-pentylanthracene was collected as the top product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A4

2-Alkylanthraquinone was prepared according to the method of Example A1, except that in step (II), the temperature reduction rate was 2° C./h, the crystallizing temperature was 192° C., the amount of anthracene added as crystal seed comprised 2 wt % of the mass of the molten mixture, the time for crystal growth was controlled to 3 hours. After the crystallization was completed, the uncrystallized stream was discharged and sent to a vacuum distillation system. The crystal in the crystallizer was slowly heated and sweated, wherein the heating rate was 2.0° C./h, the sweating finishing temperature was 197° C., the sweating amount was 15 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1 KPa, the temperature at the column bottom was 259° C., the theoretical plate number was 40, the top reflux ratio was 1.5. The column top distillate was subjected to a second vacuum distillation, wherein the column top pressure was 1 KPa, the temperature at the column bottom was 248° C., the theoretical plate number was 40, the top reflux ratio was 3. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A5

2-alkylanthraquinone was prepared according to the method of Example A1, except that in step (II), the temperature reduction rate was 1° C./h, the crystallizing temperature was 197° C., the amount of anthracene added as crystal seed comprised 1 wt % of the mass of the molten mixture, the time for crystal growth was controlled to 1.5 hours. After the crystallization was completed, the uncrystallized stream was discharged and sent to a vacuum distillation system. The crystal in the crystallizer was slowly heated and sweated, wherein the heating rate was 0.6° C./h, the sweating finishing temperature was 202° C., the sweating amount was 20 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 0.8 KPa, the temperature at the column bottom was 239° C., the theoretical plate number was 75, the top reflux ratio was 2. The column top distillate was subjected to a second vacuum distillation, wherein the column top pressure was 1.2 KPa, the temperature at the column bottom was 274° C., the theoretical plate number was 75, the top reflux ratio was 4. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A6

2-alkylanthraquinone was prepared according to the method of Example A1, except that in step (II), the temperature reduction rate was 1.5° C./h, the crystallizing temperature was 195° C., the amount of anthracene added as crystal seed comprised 1.5 wt % of the mass of the molten mixture, the time for crystal growth was controlled to 2.5 hours. After the crystallization was completed, the uncrystallized stream was discharged and sent to a vacuum distillation system. The crystal in the crystallizer was slowly heated and sweated, wherein the heating rate was 1° C./h, the sweating finishing temperature was 199° C., the sweating amount was 30 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1.2 KPa, the temperature at the column bottom was 279° C., the theoretical plate number was 65, the top reflux ratio was 1. The column top distillate was subjected to a second vacuum distillation, wherein the column top pressure was 0.8 KPa, the temperature at the column bottom was 236° C., the theoretical plate number was 70, the top reflux ratio was 1. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A7

When 2-butylanthraquinone was the target product, the other materials and the reaction conditions were the same as in Example A1, except that in step (I), 2-methyl-2-butene was changed to isobutylene in an amount of 121 g, and the alkylation reaction was performed in the same manner as in Example A1. In step (II), the temperature reduction rate was 0.5° C./h, the temperature for cooling and crystallizing was 200° C., the amount of anthracene added as crystal seed was 0.5 wt % of the mass of the molten mixture, the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together.

The uncrystallized alkylanthracene mixture was sent to the vacuum distillation system to proceed a first vacuum distillation, wherein the column top pressure was 1 KPa, the temperature at the column bottom was 250° C., the theoretical plate number was 65, the top reflux ratio was 1.5. The column top distillate was subjected to a second vacuum distillation, wherein the column top pressure was 1 KPa, the temperature at the column bottom was 238° C., the theoretical plate number was 70, the top reflux ratio was 3. 2-butylanthracene was collected as the bottom product. In step (III), the oxidation reaction solvent was a mixture of 300 mL of 1,3,5-trimethylbenzene and 2700 mL of N,N-dimethylformamide. The catalyst was zirconium dioxide in an amount of 79 g. The hydrogen peroxide solution was in an amount of 1453 g, and the reaction temperature was 95° C.

Anthracene conversion $X_1$ and 2-butylanthracene selectivity $S_{Ci-AN}$ in step (I); the purity $B_1$ of anthracene obtained by separation in step (II), the purity $B_2$ of intermediate product 2-butylanthracene, the total yield Y for the 2-butylanthracene separation; 2-butylanthracene conversion $X_2$ and 2-butylanthraquinone selectivity $S_{Ci-AO}$ in step (III) were shown in Table A.

Example A8

When 2-hexylanthracene was the target product, the other materials and the reaction conditions were the same as in Example A1, except that in step (I), 2-methyl-2-butene was changed to 2-methyl-2-pentene in an amount of 181 g, and the alkylation reaction was performed in the same manner as in Example A1. In step (II), the temperature reduction rate was 0.5° C./h, the temperature for cooling and crystallizing was 200° C., the amount of anthracene added as crystal seed was 0.5 wt % of the mass of the molten mixture, the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together.

The uncrystallized alkylanthracene mixture was sent to the vacuum distillation system to proceed a first vacuum distillation, wherein the column top pressure was 1 KPa, the temperature at the column bottom was 273° C., the theoretical plate number was 65, the top reflux ratio was 1.5. The column top distillate was subjected to a second vacuum distillation, wherein the column top pressure was 1 KPa, the temperature at the column bottom was 261° C., the theoretical plate number was 70, the top reflux ratio was 3. 2-hexylanthracene was collected as the bottom product. In step (III), the oxidation reaction solvent was a mixture of 300 mL of 1,3,5-trimethylbenzene and 2700 mL of N,N-dimethylformamide. The catalyst was metatitanic acid in an amount of 224 g. The hydrogen peroxide solution was in an amount of 1298 g, and the reaction temperature was 95° C.

Anthracene conversion $X_1$ and 2-hexylanthracene selectivity $S_{Ci-AN}$ in step (I); the purity $B_1$ of anthracene obtained by separation in step (II), the purity $B_2$ of intermediate product 2-hexylanthracene, the total yield Y for the 2-hexylanthracene separation; 2-hexylanthracene conversion $X_2$ and 2-hexylanthraquinone selectivity $S_{Ci-AO}$ in step (III) were shown in Table A.

Example A9

Step (I) was the same as in Example A1, except that the combined solvent was changed to 640 mL of 2,3,5,6-tetramethylbenzene and 160 mL of N,N-dimethylformamide.

Step (II) was the same as in Example A1.

Step (III) was the same as in Example A1, except that the used amount of 2-pentylanthracene was 266 g, and the oxidation reaction solvent was a mixture of 2700 mL of 1,3,5-trimethylbenzene and 300 mL of N,N-dimethylformamide. The catalyst was lanthanum nitrate hexahydrate in an amount of 116 g. The hydrogen peroxide solution was in an amount of 607.5 g, and the reaction temperature was 120° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A10

Step (I) was the same as in Example A1, except that the combined solvent was changed to 640 mL of 1,3,5-trimethylbenzene and 160 mL of N,N-dimethylacetamide.

Step (II) was the same as in Example A1.

Step (III) was the same as in Example A1, except that the used amount of 2-pentylanthracene was 600 g, and the oxidation reaction solvent was a mixture of 1500 mL of 1,3,5-trimethylbenzene and 1500 mL of N,N-dimethylformamide. The catalyst was lanthanum nitrate hexahydrate in an amount of 262 g. The hydrogen peroxide solution was in an amount of 1370 g, and the reaction temperature was 120° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A11

Step (I) was the same as in Example A1, except that the combined solvent was changed to 720 mL of 1,3,5-trimethylbenzene and 80 mL of N,N-dimethylformamide.

Step (II) was the same as in Example A1.

Step (III) was the same as in Example A1, except that the oxidation reaction solvent was a mixture of 300 mL of 2,3,5,6-tetramethylbenzene and 2700 mL of N,N-dimethylacetamide. The catalyst was zirconium dioxide in an amount of 74 g. The hydrogen peroxide solution was in an amount of 1368 g, and the reaction temperature was 95° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A12

Step (I) was the same as in Example A1, except that the combined solvent was changed to 80 mL of mesitylene and 720 mL of N,N-dimethylacetamide.

Step (II) was the same as in Example A1.

Step (III) was the same as in Example A1, except that the oxidation reaction solvent was 3000 mL of 1,3,5-mesitylene. The catalyst was sodium molybdate in an amount of 124 g. The hydrogen peroxide solution was in an amount of 1368 g, and the reaction temperature was 95° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A13

(I) Alkylation Reaction.

2-pentylanthracene was prepared by alkylation of anthracene and isopentene, wherein mesitylene and N,N-dimethylformamide were used as a combined solvent, the catalyst was a spherical catalyst containing an active Y zeolite, alumina was used as binder, based on the total weight of the catalyst, the content of the active Y zeolite was 82 wt %, the content of the binder was 18 wt %, and the average particle diameter of catalyst particles was 100 μm. 76 g of anthracene, 640 mL of mesitylene, 160 mL of N,N-dimethylformamide, and 333.6 g of the catalyst were charged into a 2 L stirring tank at room temperature. After sealing, the temperature was raised to 110° C. at the rotation speed of 1000 rpm, and the pressure was 0.15 MPa. 60 g of isopentene was added to the tank by means of a plunger pump at a feeding rate of 3 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

Step (II) and step (III) were the same as in Example A1.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A14

(I) Alkylation Reaction.

2-pentylanthracene was prepared by alkylation of anthracene and isopentene, wherein mesitylene and N,N-dimethylformamide were used as a combined solvent, the catalyst was a spherical catalyst containing an active Y zeolite, alumina was used as binder, based on the total weight of the catalyst, the content of the active Y zeolite was 82 wt %, the content of the binder was 18 wt %, and the average particle diameter of catalyst particles was 100 μm. 229 g of anthracene, 640 mL of mesitylene, 160 mL of N,N-dimethylformamide, and 4.68 g of the catalyst were charged into a 2 L stirring tank at room temperature. After sealing, the temperature was raised to 130° C. at the rotation speed of 1000 rpm, and the pressure was 0.15 MPa. 18 g of isopentene was added to the tank by means of a plunger pump at a feeding rate of 2 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

Step (II) and step (III) were the same as in Example A1.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A15

Both of step (I) and step (II) were the same as in Example A1. The exception was that, in step (III), the used amount of 2-pentylanthracene was 150 g, and the oxidation reaction solvent was 3000 mL of N,N-dimethylformamide. The catalyst was zirconium dioxide in an amount of 74 g. The hydrogen peroxide solution was in an amount of 1368 g, and the reaction temperature was 95° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A16

Both of step (I) and step (II) were the same as in Example A1. The exception was that, in step (III), the used amount of 2-pentylanthracene was 150 g, and the oxidation reaction solvent was 3000 mL of N,N-dimethylformamide. The catalyst was sodium molybdate in an amount of 124 g. The hydrogen peroxide solution was in an amount of 1368 g, and the reaction temperature was 95° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

Example A17

Both of step (I) and step (II) were the same as in Example A1. The exception was that, in step (III), the used amount of 2-pentylanthracene was 150 g, and the oxidation reaction solvent was 3000 mL of N,N-dimethylformamide. The catalyst was ferric oxide in an amount of 97 g. The hydrogen peroxide solution was in an amount of 1368 g, and the reaction temperature was 95° C.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table A.

TABLE A

| Step | Index % | Comparative Example A1 | Example A1 | Example A2 | Example A3 | Example A4 | Example A5 |
|---|---|---|---|---|---|---|---|
| I | $X_1$ | 65.67 | 57.11 | 65.67 | 65.67 | 65.67 | 65.67 |
|   | $S_{Ci-AN}$ | 93.21 | 86.01 | 93.21 | 93.21 | 93.21 | 93.21 |
| II | $B_1$ | 99.21 | 94.02 | 98.11 | 99.21 | 98.42 | 99.14 |
|    | $B_2$ | 99.24 | 97.86 | 99.21 | 99.33 | 97.44 | 99.47 |
|    | Y | 93.42 | 83.22 | 91.48 | 93.58 | 89.42 | 93.52 |
| III | $X_2$ | 54.24 | 97.53 | 54.24 | 54.24 | 54.24 | 54.24 |
|     | $S_{Ci-AO}$ | 95.66 | 98.14 | 95.66 | 95.66 | 95.66 | 95.66 |

| Step | Index % | Example A6 | Example A7 | Example A8 | Example A9 | Example A10 | Example A11 |
|---|---|---|---|---|---|---|---|
| I | $X_1$ | 65.67 | 68.21 | 62.10 | 64.98 | 62.12 | 60.12 |
|   | $S_{Ci-AN}$ | 93.21 | 91.34 | 94.30 | 93.79 | 91.01 | 88.12 |
| II | $B_1$ | 99.05 | 99.18 | 99.37 | 99.19 | 99.27 | 99.27 |
|    | $B_2$ | 98.01 | 99.32 | 99.45 | 99.27 | 99.32 | 99.01 |
|    | Y | 89.88 | 93.22 | 93.03 | 93.51 | 93.52 | 92.12 |
| III | $X_2$ | 54.24 | 66.05 | 60.45 | 28.12 | 35.89 | 66.32 |
|     | $S_{Ci-AO}$ | 95.66 | 94.02 | 96.34 | 90.23 | 91.22 | 94.12 |

| Step | Index % | Example A12 | Example A13 | Example A14 | Example A15 | Example A16 | Example A17 |
|---|---|---|---|---|---|---|---|
| I | $X_1$ | 22.36 | 81.44 | 15.89 | 65.67 | 65.67 | 65.67 |
|   | $S_{Ci-AN}$ | 85.01 | 91.19 | 94.12 | 93.21 | 93.21 | 93.21 |
| II | $B_1$ | 99.19 | 99.11 | 99.31 | 99.21 | 99.21 | 99.21 |
|    | $B_2$ | 99.35 | 99.31 | 99.22 | 99.24 | 99.24 | 99.24 |
|    | Y | 93.10 | 93.01 | 93.38 | 93.42 | 93.42 | 93.42 |
| III | $X_2$ | 20.39 | 54.24 | 54.24 | 65.01 | 63.79 | 4.12 |
|     | $S_{Ci-AO}$ | 88.01 | 95.66 | 95.66 | 93.82 | 92.04 | 67.12 |

It can be seen from the results in Table A that in the method provided by the present invention for preparing 2-alkylanthraquinone by catalytic oxidation of 2-alkylanthracene obtained by the alkylation of anthracene, using the combined solvent as the reaction medium in the alkylation reaction can intensify the alkylation reaction, improve the conversion of anthracene, and facilitate the production of target product. With the melting crystallization-distillation coupling separation technology, the purity of the crystal anthracene obtained by separation, the purity of the intermediate product 2-pentylanthracene (2-butylanthracene, 2-hexylanthracene) and the total yield of the separation process of the 2-pentylanthracene (2-butylanthracene, 2-hexylanthracene) were obviously improved compared with the prior art, and the total yield of the finally obtained 2-alkylanthraquinone was also improved.

Compared with the prior art, despite the slightly lower efficiency, the 2-alkylanthracene oxidation technology provided by the present invention had the advantages of simple system, no corrosivity, no generation of chlorine-containing wastewater, easy recovery of the catalyst, and simple and clean process. The developed combined solvent system could enhance the conversion of the 2-alkylanthracene and improve the selectivity of the 2-alkylanthraquinone by adjusting the properties of the solvent. Therefore, the method provided by the invention opened up a new direction for the green preparation of the 2-alkylanthraquinone.

The following Examples B1-B17 were provided to illustrate the preparation of 2-alkylanthraquinone provided by the present invention.

Example B1

(I) Alkylation Reaction.

2-pentylanthracene (i.e., 2-tert-pentylanthracene, the same applied hereinafter) was prepared by alkylation of anthracene and isopentene (i.e., 2-isopentene or 2-methyl-2-butene, the same applied hereinafter), wherein mesitylene was used as solvent, and methanesulfonic acid was used as catalyst. 460 g of anthracene, 800 mL of mesitylene, and 42 g of methanesulfonic acid were charged into a 2 L stirring tank at room temperature. After sealing, the temperature was raised to 165° C. at the rotation speed of 1000 rpm, and the pressure was 0.3 MPa. 151 g of isopentene was added to the tank by means of a plunger pump at a feeding rate of 6.6 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

(II) Separation.

The alkylation reaction product was sent to an atmospheric distillation system, the temperature was raised to 165° C. under normal pressure, and light components such as the residual isopentene, and mesitylene that had lower boiling points than anthracene could be successively separated. The remaining was a solid mixture of anthracene-alkylanthracene, the mixture was heated to 220° C., and maintained in a molten state and sent to a batch melting crystallization system; the melting crystallizer was a tubular crystallizer, and a cooling medium was introduced to start the cooling and crystallization. The temperature reduction rate was 0.5° C./h, the temperature for cooling and crystallizing was 200° C., the amount of anthracene added as crystal seed was 0.5 wt % of the mass of the molten mixture, and the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together.

The uncrystallized alkylanthracene mixture was sent to the vacuum distillation system to proceed a first vacuum distillation, wherein the column top pressure was 1 KPa, the temperature at the column bottom was 300° C., the theoretical plate number was 65, the top reflux ratio was 1.5. The column top distillate was subjected to a second vacuum distillation, wherein the column top pressure was 1 KPa, the temperature at the column bottom was 240° C., the theoretical plate number was 70, the top reflux ratio was 3. 2-pentylanthracene was collected as the bottom product.

(III) Oxidation Reaction.

The preparation of the supported solid catalyst comprised the following steps: 7.6 g of ammonium phosphate, 54 g of ammonium chromate and 80 mL of water at 80° C. were uniformly mixed, 133 g of the support $SiO_2$—$Al_2O_3$ composite (the average particle diameter of microspheres was 100 m, wherein the content of $Al_2O_3$ was 92 wt %) was dispersed in the mixture and impregnated for 6 hours, the impregnated support was placed in a drying oven at 110° C. to be dried for 12 hours to obtain powder, the powder was heated to 500° C. at the heating rate of 5° C./min in a muffle furnace and calcined for 5 hours to obtain the supported solid catalyst. The total amount of the supported elements was 15 wt % in terms of the element based on the weight of the support. The content of the supported P was 1.2 wt %, the content of the supported metal Cr was 13.8 wt %, and the catalyst was expressed as P (1.2 wt %)-Cr (13.8 wt %)/$SiO_2$—$Al_2O_3$ (92 wt %). The above steps were repeated for several times until enough catalysts were prepared.

2-pentylanthracene was subjected to a liquid phase oxidation to prepare 2-pentylanthraquinone. 3000 mL of chlorobenzene, 150 g of 2-pentylanthracene, and 587 g of the above-mentioned supported solid catalyst were charged into an 8 L glass tank. The reaction was performed under normal pressure at 80° C., 1089 g of tert-butyl hydroperoxide was added into the tank by a peristaltic pump, and the feeding rate was 5 g/min. When the feeding was finished, the reaction was continued while the reaction condition was kept unchanged, and the total time for the reaction was 20 hours. After the reaction was finished, the catalyst was removed through sedimentation or filtration, and the reaction liquor was distilled to obtain the final product 2-pentylanthraquinone.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Comparative Example B1

2-Alkylanthraquinone was prepared according to the method of Example B1, except that in step (II), after removing by distillation light components with boiling points less than that of anthracene, anthracene was directly separated by vacuum distillation instead of melting crystallization. The distillation column for separating anthracene was a vacuum distillation system for the separation of anthracene, wherein the column top pressure was 8 KPa, the distillation temperature was 275° C., the theoretical plate number was 20, the top reflux ratio was 0.7. The column bottom distillates were sent to the first vacuum distillation and the second vacuum distillation under the same conditions as in Example B1.

In step (III), 3000 ml of methanol, 150 g of 2-pentylanthracene, and 307 g of 36 wt % hydrochloric acid were sent to a 5 L glass tank. The reaction was performed under normal pressure at 65° C., 342 g of hydrogen peroxide solution (the content of hydrogen peroxide was 30 wt %) was added into the tank by a peristaltic pump, and the feeding rate was 2 g/min. After the feeding was completed, the reaction was continued for 2 hours while maintaining the conditions unchanged. After the reaction was completed, the stream in the tank was transferred into a 20 L glass stirring tank, 2000 mL of mesitylene and 3000 mL of deionized water were added for extraction and washing. After standing, the mesitylene phase containing 2-pentylanthraquinone was separated out as the upper layer, and distilled to obtain the final product 2-pentylanthraquinone.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B2

2-Alkylanthraquinone was prepared according to the method of Example B1, except that in step (II), the temperature reduction rate was 5.0° C./h, the crystallizing temperature was 190° C., the amount of anthracene added as crystal seed comprised 4 wt % of the mass of the molten mixture, the time for crystal growth was controlled to 4 hours. After the crystallization was completed, the uncrystallized stream was discharged and sent to a vacuum distillation system. The crystal in the crystallizer was slowly heated and sweated, wherein the heating rate was 4° C./h, the sweating finishing temperature was 195° C., the sweating amount was 10 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1 KPa, the temperature at the column bottom was 300° C., the theoretical plate number was 65, the top reflux ratio was 1.5. The column top distillate was subjected to a second vacuum distillation, wherein the column top pressure was 1 KPa, the temperature at the column bottom was 240° C., the theoretical plate number was 70, the top reflux ratio was 3. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B3

2-Alkylanthraquinone was prepared according to the method of Example B1, except that in step (II), the uncrystallized alkylanthracene mixture was fed to a vacuum distillation system to perform a third vacuum distillation, wherein the column top pressure was 1 KPa, the temperature at the column bottom was 290° C., the theoretical plate number was 65, the top reflux ratio was 1.5. The bottom distillate was subjected to a fourth vacuum distillation, wherein the top pressure was 1 KPa, the temperature at the column bottom was 305° C., the theoretical plate number was 70, the top reflux ratio was 3. 2-pentylanthracene was collected as the top product. Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B4

2-Alkylanthraquinone was prepared according to the method of Example B1, except that in step (II), the temperature reduction rate was 2° C./h, the crystallizing temperature was 192° C., the amount of anthracene added as crystal seed comprised 2 wt % of the mass of the molten mixture, the time for crystal growth was controlled to 3 hours. After the crystallization was completed, the uncrystallized stream was discharged and sent to a vacuum distillation system. The crystal in the crystallizer was slowly heated and sweated, wherein the heating rate was 2.0° C./h, the sweating finishing temperature was 197° C., the sweating amount was 15 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1 KPa, the temperature at the column bottom was 300° C., the theoretical plate number was 40, the top reflux ratio was 1.5. The column top distillate was subjected to a second vacuum distillation, wherein the column top pressure was 1 KPa, the temperature at the column bottom was 240° C., the theoretical plate number was 40, the top reflux ratio was 3. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B5

2-Alkylanthraquinone was prepared according to the method of Example B1, except that in step (II), the temperature reduction rate was 1° C./h, the crystallizing temperature was 197° C., the amount of anthracene added as crystal seed comprised 1 wt % of the mass of the molten mixture, the time for crystal growth was controlled to 1.5 hours. After the crystallization was completed, the uncrystallized stream was discharged and sent to a vacuum distillation system. The crystal in the crystallizer was slowly heated and sweated, wherein the heating rate was 0.6° C./h, the sweating finishing temperature was 202° C., the sweating amount was 20 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 0.8 KPa, the temperature at the column bottom was 280° C., the theoretical plate number was 75, the top reflux ratio was 2. The column top distillate was subjected to a second vacuum distillation, wherein the column top pressure was 1.2 KPa, the temperature at the column bottom was 266° C., the theoretical plate number was 75, the top reflux ratio was 4. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B6

2-Alkylanthraquinone was prepared according to the method of Example B1, except that in step (II), the temperature reduction rate was 1.5° C./h, the crystallizing temperature was 195° C., the amount of anthracene added as crystal seed comprised 1.5 wt % of the mass of the molten mixture, the time for crystal growth was controlled to 2.5 hours. After the crystallization was completed, the uncrystallized stream was discharged and sent to a vacuum distillation system. The crystal in the crystallizer was slowly heated and sweated, wherein the heating rate was 1° C./h, the sweating finishing temperature was 199° C., the sweating amount was 30 wt % based on the crystal mass, and the sweating liquor was recycled and contacted with the stream entering the melting crystallizer and took part in the crystallization together. The uncrystallized alkylanthracene mixture was sent to the vacuum distillation system to proceed a first vacuum distillation, wherein the column top pressure was 1.2 KPa, the temperature at the column bottom was 320° C., the theoretical plate number was 65, the top reflux ratio was 1. The column top distillate was subjected to a second vacuum distillation, wherein the column top pressure was 0.8 KPa, the temperature at the column bottom was 228° C., the theoretical plate number was 70, the top reflux ratio was 1. 2-pentylanthracene was collected as the bottom product.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B7

When 2-butylanthraquinone was the target product, the other materials and the reaction conditions were the same as in Example B1, except that in step (I), 2-methyl-2-butene was changed to isobutylene in an amount of 121 g, and the alkylation reaction was performed in the same manner as in Example B1. In step (II), the temperature reduction rate was 0.5° C./h, the temperature for cooling and crystallizing was 200° C., the amount of anthracene added as crystal seed was 0.5 wt % of the mass of the molten mixture, the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together.

The uncrystallized alkylanthracene mixture was sent to the vacuum distillation system to proceed a first vacuum distillation, wherein the column top pressure was 1 KPa, the temperature at the column bottom was 291° C., the theoretical plate number was 65, the top reflux ratio was 1.5. The column top distillate was subjected to a second vacuum distillation, wherein the column top pressure was 1 KPa, the temperature at the column bottom was 221° C., the theoretical plate number was 70, the top reflux ratio was 3.

2-butylanthracene was collected as the bottom product. In step (III), the amount of the catalyst was changed to 832.5 g.

Anthracene conversion $X_1$ and 2-butylanthracene selectivity $S_{Ci\text{-}AN}$ in step (I); the purity $B_1$ of anthracene obtained by separation in step (II), the purity $B_2$ of intermediate product 2-butylanthracene, the total yield Y for the 2-butylanthracene separation; 2-butylanthracene conversion $X_2$ and 2-butylanthraquinone selectivity $S_{Ci\text{-}AO}$ in step (III) were shown in Table B.

Example B8

When 2-hexylanthracene was the target product, the other materials and the reaction conditions were the same as in Example B1, except that in step (I), 2-methyl-2-butene was changed to 2-methyl-2-pentene in an amount of 181 g, and the alkylation reaction was performed in the same manner as in Example B1. In step (II), the temperature reduction rate was 0.5° C./h, the temperature for cooling and crystallizing was 200° C., the amount of anthracene added as crystal seed was 0.5 wt % of the mass of the molten mixture, the time for crystal growth was controlled to 2 hours. After the crystallization was completed, the uncrystallized stream was discharged and sent to a vacuum distillation system. The crystal in the crystallizer was slowly heated and sweated, wherein the heating rate was 0.2° C./h, the sweating finishing temperature was 205° C., the sweating amount was 25 wt % based on the crystal mass, and the sweating liquor was recycled and contacted with the stream entering the melting crystallizer and took part in the crystallization together.

The uncrystallized alkylanthracene mixture was sent to the vacuum distillation system to proceed a first vacuum distillation, wherein the column top pressure was 1 KPa, the temperature at the column bottom was 310° C., the theoretical plate number was 65, the top reflux ratio was 1.5. The column top distillate was subjected to a second vacuum distillation, wherein the column top pressure was 1 KPa, the temperature at the column bottom was 251° C., the theoretical plate number was 70, the top reflux ratio was 3. 2-hexylanthracene was collected as the bottom product. In step (III), the amount of the catalyst was changed to 175.3 g.

Anthracene conversion $X_1$ and 2-hexylanthracene selectivity $S_{Ci\text{-}AN}$ in step (I); the purity $B_1$ of anthracene obtained by separation in step (II), the purity $B_2$ of intermediate product 2-hexylanthracene, the total yield Y for the 2-hexylanthracene separation; 2-hexylanthracene conversion $X_2$ and 2-hexylanthraquinone selectivity $S_{Ci\text{-}AO}$ in step (III) were shown in Table B.

Example B9

(I) Alkylation Reaction.

Anthracene and isopentene were subjected to the alkylation to prepare 2-pentylanthracene, wherein mesitylene was used as a solvent, and methanesulfonic acid was used as a catalyst. 76 g of anthracene, 800 mL of mesitylene, and 12 g of methanesulfonic acid were charged into a 2 L stirring tank at room temperature. After sealing, the temperature was raised to 110° C. at the rotation speed of 1000 rpm, and the pressure was 0.15 MPa. 60 g of isopentene was added to the tank by means of a plunger pump at a feeding rate of 3 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

Both of step (II) and step (III) were the same as in Example B1.

Anthracene conversion $X_1$ and 2-pentylanthracene selectivity $S_{Ci\text{-}AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci\text{-}AO}$ in step (III) were shown in Table B.

Example B10

(I) Alkylation Reaction.

Anthracene and isopentene were subjected to the alkylation to prepare 2-pentylanthracene, wherein mesitylene was used as a solvent, and methanesulfonic acid was used as a catalyst. 229 g of anthracene, 800 mL of mesitylene, and 40 g of methanesulfonic acid were charged into a 2 L stirring tank at room temperature. After sealing, the temperature was raised to 130° C. at the rotation speed of 1000 rpm, and the pressure was 0.2 MPa. 18 g of isopentene was added to the tank by means of a plunger pump at a feeding rate of 2 g/min. When the feeding of isopentene was finished, the reaction was continued for 270 min while the reaction condition was kept unchanged, and then the reaction was terminated. 10 batches of reaction were performed under the same condition, and after the separation of the catalyst, the alkylation reaction products were uniformly collected and used as the feedstock for the alkylanthracene separation.

Both of step (II) and step (III) were the same as in Example B1.

Anthracene conversion $X_1$ and 2-pentylanthracene selectivity $S_{Ci\text{-}AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci\text{-}AO}$ in step (III) were shown in Table B.

Example B11

Both of step (I) and step (II) were the same as in Example B1. The exception was that, in step (III), the used amount of the oxidizing agent was changed to 150 g.

Anthracene conversion $X_1$ and 2-pentylanthracene selectivity $S_{Ci\text{-}AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci\text{-}AO}$ in step (III) were shown in Table B.

Example B12

Both of step (I) and step (II) were the same as in Example B1. The exception was that, in step (III), the used amount of the oxidizing agent was changed to 272.25 g.

Anthracene conversion $X_1$ and 2-pentylanthracene selectivity $S_{Ci\text{-}AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci\text{-}AO}$ in step (III) were shown in Table B.

Example B13

Both of step (I) and step (II) were the same as in Example B1. The exception was that, in step (III), the oxidation reaction solvent was 3000 mL of N,N-dimethylformamide, and the used amount of the catalyst was changed to 503 g.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B14

Both of step (I) and step (II) were the same as in Example B1. The exception was that, in step (III), the catalyst was changed to Cr/SiO$_2$—Al$_2$O$_3$ (92 wt %).

The preparation of the supported solid catalyst comprised the following steps: 58.68 g of ammonium chromate and 80 mL of water at 80° C. were uniformly mixed, 133 g of the support SiO$_2$—Al$_2$O$_3$ composite (the average particle diameter of microspheres was 100 m, wherein the content of Al$_2$O$_3$ was 92 wt %) was dispersed in the mixture and impregnated for 6 hours, the impregnated support was placed in a drying oven at 110° C. to be dried for 12 hours to obtain powder, the powder was heated to 500° C. at the heating rate of 5° C./min in a muffle furnace and calcined for 5 hours to obtain the supported solid catalyst. The amount of the supported metal Cr was 15 wt % in terms of the element based on the weight of the support. The catalyst was expressed as Cr/SiO$_2$—Al$_2$O$_3$ (92 wt %). The above steps were repeated for several times until enough catalysts were prepared.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B15

Both of step (I) and step (II) were the same as in Example B1. The exception was that, in step (III), the catalyst was changed to P (1.2 wt %)-Ni (13.8 wt %)/SiO$_2$—Al$_2$O$_3$ (92 wt %).

The preparation of the supported solid catalyst comprised the following steps: 7.6 g of ammonium phosphate, 57.3 g of nickelous nitrate and 80 mL of water were uniformly mixed, 133 g of the support SiO$_2$—Al$_2$O$_3$ composite (the average particle diameter of microspheres was 100 μm, wherein the content of Al$_2$O$_3$ was 92 wt %) was dispersed in the mixture and impregnated for 6 hours, the impregnated support was placed in a drying oven at 110° C. to be dried for 12 hours to obtain powder, the powder was heated to 500° C. at the heating rate of 5° C./min in a muffle furnace and calcined for 5 hours to obtain the supported solid catalyst. The total amount of the supported elements was 15 wt % in terms of the element based on the weight of the support. The content of the supported P was 1.2 wt %, the content of the supported metal Ni was 13.8 wt %, and the catalyst was expressed as P (1.2 wt %)-Ni (13.8 wt %)/SiO$_2$—Al$_2$O$_3$ (92 wt %). The above steps were repeated for several times until enough catalysts were prepared.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B16

Both of step (I) and step (II) were the same as in Example B1. The exception was that, in step (III), the catalyst was changed to P (0.8 wt %)-Cr (9.2 wt %)/SiO$_2$—Al$_2$O$_3$ (92 wt %).

The preparation of the supported solid catalyst comprised the following steps: 5.07 g of ammonium phosphate, 35.99 g of ammonium chromate and 80 mL of water at 80° C. were uniformly mixed, 133 g of the support SiO$_2$—Al$_2$O$_3$ composite (the average particle diameter of microspheres was 100 μm, wherein the content of Al$_2$O$_3$ was 92 wt %) was dispersed in the mixture and impregnated for 6 hours, the impregnated support was placed in a drying oven at 110° C. to be dried for 12 hours to obtain powder, the powder was heated to 500° C. at the heating rate of 5° C./min in a muffle furnace and calcined for 5 hours to obtain the supported solid catalyst. The total amount of the supported elements was 10 wt % in terms of the element based on the weight of the support. The content of the supported P was 0.8 wt %, the content of the supported metal Cr was 9.2 wt %, and the catalyst was expressed as P (0.8 wt %)-Cr (9.2 wt %)/SiO$_2$—Al$_2$O$_3$ (92 wt %). The above steps were repeated for several times until enough catalysts were prepared.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

Example B17

Both of step (I) and step (II) were the same as in Example B1. The exception was that, in step (III), the catalyst was changed to P (1.44 wt %)-Cr (16.56 wt %)/SiO$_2$—Al$_2$O$_3$ (92 wt %).

The preparation of the supported solid catalyst comprised the following steps: 9.12 g of ammonium phosphate, 64.78 g of ammonium chromate and 80 mL of water at 80° C. were uniformly mixed, 133 g of the support SiO$_2$—Al$_2$O$_3$ composite (the average particle diameter of microspheres was 100 μm, wherein the content of Al$_2$O$_3$ was 92 wt %) was dispersed in the mixture and impregnated for 6 hours, the impregnated support was placed in a drying oven at 110° C. to be dried for 12 hours to obtain powder, the powder was heated to 500° C. at the heating rate of 5° C./min in a muffle furnace and calcined for 5 hours to obtain the supported solid catalyst. The total amount of the supported elements was 18 wt % in terms of the element based on the weight of the support. The content of the supported P was 1.44 wt %, the content of the supported metal Cr was 16.56 wt %, and the catalyst was expressed as P (1.44 wt %)-Cr (16.56 wt %)/SiO$_2$—Al$_2$O$_3$ (92 wt %). The above steps were repeated for several times until enough catalysts were prepared.

Anthracene conversion $X_1$ and 2-pentylanthracene selectivity $S_{Ci-AN}$ in step (I); the purity $B_1$ of anthracene obtained by separation in step (II), the purity $B_2$ of intermediate product 2-pentylanthracene, the total yield Y for the 2-pentylanthracene separation; 2-pentylanthracene conversion $X_2$ and 2-pentylanthraquinone selectivity $S_{Ci-AO}$ in step (III) were shown in Table B.

TABLE B

| Step | Index % | Example B1 | Comparative Example B1 | Example B2 | Example B3 | Example B4 | Example B5 |
|---|---|---|---|---|---|---|---|
| I | $X_1$ | 51.14 | 51.14 | 51.14 | 51.14 | 51.14 | 51.14 |
|   | $S_{Ci-AN}$ | 61.72 | 61.72 | 61.72 | 61.72 | 61.72 | 61.72 |
| II | $B_1$ | 99.50 | 95.42 | 98.70 | 99.50 | 99.10 | 99.30 |
|    | $B_2$ | 99.30 | 98.01 | 99.30 | 99.23 | 97.50 | 99.50 |
|    | Y | 93.31 | 87.53 | 92.10 | 92.31 | 89.57 | 94.23 |
| III | $X_2$ | 91.03 | 97.53 | 91.03 | 91.03 | 91.03 | 91.03 |
|     | $S_{Ci-AO}$ | 98.77 | 98.14 | 98.77 | 98.77 | 98.77 | 98.77 |

| Step | Index % | Example B6 | Example B7 | Example B8 | Example B9 | Example B10 | Example B11 |
|---|---|---|---|---|---|---|---|
| I | $X_1$ | 51.14 | 56.36 | 47.73 | 75.14 | 20.63 | 51.14 |
|   | $S_{Ci-AN}$ | 61.72 | 67.52 | 69.37 | 35.85 | 71.39 | 61.72 |
| II | $B_1$ | 99.30 | 99.31 | 99.34 | 99.50 | 99.50 | 99.50 |
|    | $B_2$ | 98.10 | 99.42 | 99.36 | 99.03 | 99.11 | 99.30 |
|    | Y | 90.04 | 93.15 | 92.86 | 91.28 | 90.67 | 93.31 |
| III | $X_2$ | 91.03 | 96.29 | 79.02 | 91.03 | 91.03 | 80.8 |
|     | $S_{Ci-AO}$ | 98.77 | 98.67 | 98.71 | 98.77 | 98.77 | 98.79 |

| Step | Index % | Example B12 | Example B13 | Example B14 | Example B15 | Example B16 | Example B17 |
|---|---|---|---|---|---|---|---|
| I | $X_1$ | 51.14 | 51.14 | 51.14 | 51.14 | 51.14 | 51.14 |
|   | $S_{Ci-AN}$ | 61.72 | 61.72 | 61.72 | 61.72 | 61.72 | 61.72 |
| II | $B_1$ | 99.50 | 99.50 | 99.50 | 99.50 | 99.50 | 99.50 |
|    | $B_2$ | 99.30 | 99.30 | 99.30 | 99.30 | 99.30 | 99.30 |
|    | Y | 93.31 | 93.31 | 93.31 | 93.31 | 93.31 | 93.31 |
| III | $X_2$ | 73.01 | 84.62 | 87.84 | 20.1 | 87.05 | 93.5 |
|     | $S_{Ci-AO}$ | 98.63 | 95.4 | 95.08 | 68.31 | 98.51 | 98.84 |

It can be seen from the results in Table B that in the method provided by the present invention for preparing 2-alkylanthraquinone by catalytic oxidation of 2-alkylanthracene obtained by separation from the reaction of anthracene, with the melting crystallization-distillation coupling separation technology, the purity of the crystal anthracene obtained by separation, the purity of the intermediate product 2-pentylanthracene (2-butylanthracene, 2-hexylanthracene) and the total yield of the separation process of the 2-pentylanthracene (2-butylanthracene, 2-hexylanthracene) were obviously improved compared with the prior art, and the total yield of the finally obtained 2-alkylanthraquinone was also improved.

Furthermore, the 2-alkylanthracene oxidization technology in the method provided by the present invention for preparing 2-alkylanthraquinone by catalytic oxidation of 2-alkylanthracene obtained by separation from the reaction of anthracene, using the oxidizing agent tert-butyl hydroperoxide and the supported catalyst of the present invention in combination, compared with the prior art, despite the slightly lower feedstock conversion, had the advantages of good selectivity, no corrosivity, no generation of chlorine-containing wastewater, easy recovery of the catalyst, and simple and clean process. Therefore, the method provided by the present invention opened up a new direction for the green preparation of the 2-alkylanthraquinone.

In the following examples, the 2-pentylanthraquinone working fluid was prepared by mixing 2-pentylanthraquinone with a nonpolar solvent mesitylene and a polar solvent diisobutylmethanol, wherein the content of 2-pentylanthraquinone in the mixed solvent of the nonpolar solvent and the polar solvent was 220 g/L, and the volume ratio of the nonpolar solvent to the polar solvent in the mixed solvent was 3:2.

In the following examples, the method for determining the sulfur content in the 2-pentylanthraquinone working fluid was the total sulfur method: the total sulfur content measured by UV fluorescence method, SHT 0689-2000.

In the following examples, the method for measuring the content of impurities in the 2-pentylanthraquinone working fluid was the chromatographic analysis method, and the analysis conditions were as follows: Agilent company 7890A; chromatographic column: DB-1 (50 m×0.25 mm×0.25 μm). Sample inlet temperature: 330° C., sample size: 0.2 μL, the split ratio: 20:1, the carrier gas: nitrogen, the flow rate in constant flow mode: 0.7 mL/min, and the temperature programming: keeping the temperature at 110° C. for 10 min, then raising the temperature to 320° C. at the rate of 5° C./min, and keeping the temperature for 18 min. FID detector: temperature: 350° C., hydrogen flow rate: 35 mL/min, air flow: 350 mL/min, purge gas: nitrogen, and flow: 25 mL/min. Area normalization: the peak areas of anthraquinone-substances except the solvent were normalized, and the fraction of the chromatographic peak areas of the impurities represented the mass fraction thereof.

Preparation Example C1

This preparation example was used to illustrate the preparation of an amorphous alloy Ni—Fe—Al adsorbent. 25 g of nickel, 50 g of aluminum and 15 g of iron were added into a quartz tube, and heated to above 1300° C. in a high-frequency furnace to melt and alloy them. Then the alloy liquid was sprayed onto a copper roller with the rotation speed of 800 rpm from a nozzle below the quartz tube (the spraying pressure: 0.08 MPa). Cooling water was introduced into the copper roller. The alloy liquid was rapidly cooled, and threw out along the tangent line of the copper roller to form a scale-shaped strip. The scale-shaped strip was ground to the particle diameter of 60-80 micrometers to obtain the master alloy. XRD analysis was performed on the obtained master alloy by using an X-ray powder diffractometer (Japan Rigaku D/MAX-2500 X-ray diffractometer, CuKα-ray, current: 100 mA, the same applied hereinafter), and the obtained XRD pattern showed that a diffusion peak appeared at 45±1° within the 2θ angle range of 20-80°, which was a typical feature of amorphous alloy, indicating that the obtained Ni—Fe—Al alloy product was an alloy in an amorphous form.

The master alloy was subjected to a heat treatment in a hydrogen atmosphere, wherein the heat treatment temperature was 600° C. and the constant-temperature treatment time was 3 hours. The heat-treated master alloy was slowly added to a three-necked flask containing 1000 g of 20 wt % aqueous sodium hydroxide solution, and the temperature was controlled at 100° C. and stirred at the constant temperature for 1 hour. After the heating and stirring was stopped, the liquid was decanted, and the alloy was washed with distilled water at 80° C. to the pH value of 7. Then benzene was added, and water was removed by azeotropic distillation at atmospheric pressure (normal pressure). The alloy was stored in benzene until use. The compositions of the resulting adsorbents were shown in Table C.

Preparation Examples C2-C6

Amorphous alloy adsorbents were prepared according to the method of Preparation Example C1 except for the amount of the used metals and the alloy's composition, and the compositions of the resulting adsorbents were shown in Table C.

TABLE C

| Preparation Example # | Type and amount (g) of metals | | | | | | | Adsorbent Composition |
|---|---|---|---|---|---|---|---|---|
| | Ni | Al | Fe | Co | Mo | Cu | Cr | |
| Preparation Example C1 | 25 | 50 | 15 | — | — | — | — | $Ni_{58.4}Fe_{32.3}Al_{9.3}$ |
| Preparation Example C2 | 30 | 47 | 1.2 | — | — | — | 2 | $Ni_{82}Fe_{3.1}Cr_{6.2}Al_{8.7}$ |
| Preparation Example C3 | 30 | 50 | 0.9 | — | — | — | 1.5 | $Ni_{89}Fe_{2.8}Cr_{4.9}Al_{3.3}$ |
| Preparation Example C4 | 30 | 50 | 3.1 | — | — | — | 2.6 | $Ni_{75.4}Fe_{8.0}Cr_{7.3}Al_{9.3}$ |
| Preparation Example C5 | 30 | 50 | — | 3.1 | — | — | 3.3 | $Ni_{74.8}Co_{7.7}Cr_{9.3}Al_{8.2}$ |
| Preparation Example C6 | 30 | 50 | — | — | — | 1.7 | 2.2 | $Ni_{82.6}Cu_{3.7}Cr_{6.2}Al_{7.5}$ |
| Preparation Example C7 | 30 | 50 | — | — | 3.3 | — | 2.3 | $Ni_{79}Mo_{5.3}Cr_{7}Al_{8.7}$ |

Example C1

This example illustrated the pretreatment of the 2-alkylanthraquinone working fluid and the preparation of hydrogen peroxide.

300 mL of 2-pentylanthraquinone working fluid (the initial sulfur content was 2.5 mg/kg) was placed in a 1000 mL glass stirring tank, and an isometric aqueous sodium hydroxide solution and the nickel-based amorphous alloy $Ni_{82}Fe_{3.1}Cr_{6.2}Al_{8.7}$ prepared in Preparation Example C2 (as adsorbent) were added to perform the coupling treatment of the adsorption desulfurization and alkali-washing impurity removal. The concentration of aqueous sodium hydroxide solution was 10 wt %, the washing pressure was normal pressure, the washing temperature was 50° C., the rotation speed for stirring was 1000 rpm, based on the weight of the 2-alkylanthraquinone working fluid, the used amount of the adsorbent was 10 wt %, the number of washing was 4, and the time for each washing was 4 hours. After the completion of each coupling treatment (not the last) of the adsorption desulfurization and the alkali-washing impurity removal, the system was allowed to stand and separated into layers, the waste alkali liquor in the lower layer was discharged, and the adsorbent was remained in the stirring tank for the next operation of desulfurization and alkali washing. After the completion of the last coupling treatment of the adsorption desulfurization and the alkali-washing impurity removal, the system was allowed to stand and separated into layers, the waste alkali liquor in the lower layer was discharged, and the adsorbent was filtered and discharged. To the separated working fluid in the upper layer was added an isometric aqueous phosphoric acid solution for washing. The concentration of aqueous phosphoric acid solution was 10 wt %, the washing pressure was normal pressure, the washing temperature was 50° C., the rotation speed for stirring was 1000 rpm, the number of washing was 4, and the time for each washing was 4 hours. After the completion of each acid washing (not the last), the system was allowed to stand and separated into layers, the waste acid liquor in the lower layer was discharged. After the completion of the last acid washing, the system was allowed to stand and separated into layers, the waste acid liquor in the lower layer was discharged, and to the separated working fluid in the upper layer was added an isometric deionized water for washing. The washing pressure was normal pressure, the washing temperature was 50° C., the rotation speed for stirring was 1000 rpm, the number of washing was 4, and the time for each washing was 4 hours. After the completion of each water washing (not the last), the system was allowed to stand and separated into layers, the water-washing waste liquor in the lower layer was discharged. After the completion of the last water washing, the system was allowed to stand and separated into layers, the water-washing waste liquor in the lower layer was discharged, and the separated working fluid in the upper layer was sent to the subsequent process. The index parameters of the working fluid before and after the pretreatment were shown in Table D.

After the pretreated 2-pentylanthraquinone working fluid was dehydrated to ensure that the water content was less than 3000 mg/kg, the dehydrated working fluid was introduced into a small continuous experimental apparatus for producing hydrogen peroxide, and the production process of the hydrogen peroxide comprised: the adsorption of the working fluid with a white clay bed; the hydrogenation of the working fluid; the adsorption of the hydrogenated liquor with a white clay bed; the oxidation of the hydrogenated liquor; the extraction of the oxidation liquor; and the drying of the working fluid.

Hydrogenation condition: continuous hydrogenation process in the stirred tank, temperature: 60° C., pressure: 0.3 MPa, and hydrogen being fed in a constant-pressure hydrogen consumption mode. The residence time of the working fluid was 20 min, the catalyst was fine powder $Pd/Al_2O_3$ (the Pd content was 1.8 wt %), and the hydrogenation efficiency was 12 g/L.

Oxidation condition: countercurrent contact oxidation process, temperature: 60° C.; pressure: normal pressure; flow rate of hydrogenation liquor: 12.5 mL/min; flow rate of pure oxygen: 80 mL/min (standard condition); and residence time: 30 min.

Adsorption conditions with white clay bed for working fluid and hydrogenated liquor: temperature: 50° C.; pressure: normal pressure; flow rate of liquid phase: 12.5 mL/min; and residence time: 15 min.

Extraction conditions: continuous sieve-tray column extraction process, temperature: 40° C.; pressure: normal pressure. The flow rate of pure water was 0.25 mL/min, and the flow rate of the working fluid was 12.5 mL/min. The raffinate was dried in vacuum until the water content was less than 3000 mg/kg, and then recycled into the hydrogenation system. The extract was collected as product. The experimental results were shown in Table E.

Example C2

This example illustrated the pretreatment of the 2-alkylanthraquinone working fluid.

The pretreatment method of 2-pentylanthraquinone working fluid was the same as that of Example C1, except that among the conditions of the coupling treatment of alkali washing and adsorption desulfurization, the washing temperature was changed to 80° C. and other conditions were not changed.

The index parameters of the working fluid before and after the pretreatment were shown in Table D.

Example C3

This example illustrated the pretreatment of the 2-alkylanthraquinone working fluid.

The pretreatment method of 2-pentylanthraquinone working fluid was the same as that of Example C1, except that among the conditions of the coupling treatment of alkali washing and adsorption desulfurization, the washing temperature was changed to 30° C. and other conditions were not changed.

The index parameters of the working fluid before and after the pretreatment were shown in Table D.

Example C4

This example illustrated the pretreatment of the 2-alkylanthraquinone working fluid.

The pretreatment method of 2-pentylanthraquinone working fluid was the same as that of Example C1, except that among the conditions of the coupling treatment of alkali washing and adsorption desulfurization, the used amount of adsorbent was changed wherein based on the weight of the 2-alkylanthraquinone working fluid, the used amount of adsorbent was 7 wt %, and other conditions were not changed.

The index parameters of the working fluid before and after the pretreatment were shown in Table D.

Example C5

This example illustrated the pretreatment of the 2-alkylanthraquinone working fluid.

The pretreatment method of 2-pentylanthraquinone working fluid was the same as that of Example C1, except that among the conditions of the coupling treatment of alkali washing and adsorption desulfurization, the used amount of adsorbent was changed wherein based on the weight of the 2-alkylanthraquinone working fluid, the used amount of adsorbent was 5 wt %, and other conditions were not changed.

The index parameters of the working fluid before and after the pretreatment were shown in Table D.

Example C6

This example illustrated the pretreatment of the 2-alkylanthraquinone working fluid.

The pretreatment method of 2-pentylanthraquinone working fluid was the same as that of Example C1, except that among the conditions of the coupling treatment of alkali washing and adsorption desulfurization, the used amount of adsorbent was changed wherein based on the weight of the 2-alkylanthraquinone working fluid, the used amount of adsorbent was 1 wt %, and other conditions were not changed.

The index parameters of the working fluid before and after the pretreatment were shown in Table D.

Example C7

This example illustrated the pretreatment of the 2-alkylanthraquinone working fluid.

The pretreatment method of 2-pentylanthraquinone working fluid was the same as that of Example C1, except that the adsorbent was the nickel-based amorphous alloy $Ni_{89}Fe_{2.8}Cr_{4.9}Al_{3.3}$ prepared by the preparation example C3, based on the weight of the 2-alkylanthraquinone working fluid, the used amount of adsorbent was 5 wt %, and other conditions are not changed.

The index parameters of the working fluid before and after the pretreatment were shown in Table D.

Example C8

This example illustrated the pretreatment of the 2-alkylanthraquinone working fluid.

The pretreatment method of 2-pentylanthraquinone working fluid was the same as that of Example C1, except that the adsorbent was the nickel-based amorphous alloy $Ni_{75.4}Fe_{8.0}Cr_{7.3}Al_{9.3}$ prepared by the preparation example C4, based on the weight of the 2-alkylanthraquinone working fluid, the used amount of adsorbent was 5 wt %, and other conditions are not changed.

The index parameters of the working fluid before and after the pretreatment were shown in Table D.

Example C9

This example illustrated the pretreatment of the 2-alkylanthraquinone working fluid.

The pretreatment method of 2-pentylanthraquinone working fluid was the same as that of Example C1, except that the adsorbent was the nickel-based amorphous alloy $Ni_{58.4}Fe_{32.3}Al_{9.3}$ prepared by the preparation example C1, based on the weight of the 2-alkylanthraquinone working fluid, the used amount of adsorbent was 5 wt %, and other conditions are not changed.

The index parameters of the working fluid before and after the pretreatment were shown in Table D.

Example C10

This example illustrated the pretreatment of the 2-alkylanthraquinone working fluid.

The pretreatment method of 2-pentylanthraquinone working fluid was the same as that of Example C1, except that, the initial sulfur content of the 2-pentylanthraquinone working fluid was 6.0 mg/kg, the adsorbent was the Ni-based amorphous alloy $Ni_{75.4}Fe_{8.0}Cr_{7.3}Al_{9.3}$ prepared from Preparation Example C4, and the conditions of the coupling treatment of alkali washing and adsorption desulfurization comprise: the washing pressure was normal pressure, the washing temperature was 80° C., the rotation speed for stirring was 1000 rpm, based on the weight of the 2-alkylanthraquinone working fluid, the used amount of adsorbent was 10 wt %, the number of washing was 4, and the time for each washing was 4 hours.

The index parameters of the working fluid before and after the pretreatment were shown in Table D.

Example C11

This example illustrated the pretreatment of the 2-alkylanthraquinone working fluid.

The pretreatment method of 2-pentylanthraquinone working fluid was the same as that of Example C1, except that, the initial sulfur content of the 2-pentylanthraquinone working fluid was 1.0 mg/kg, the adsorbent was the Ni-based amorphous alloy $Ni_{75.4}Fe_{8.0}Cr_{7.3}Al_{9.3}$ prepared from Preparation Example C4, and the conditions of the coupling treatment of alkali washing and adsorption desulfurization comprise: the washing pressure was normal pressure, the washing temperature was 80° C., the rotation speed for stirring was 1000 rpm, based on the weight of the 2-alkylanthraquinone working fluid, the used amount of adsorbent was 10 wt %, the number of washing was 4, and the time for each washing was 4 hours.

The index parameters of the working fluid before and after the pretreatment were shown in Table D.

Example C12

This example illustrated the pretreatment of the 2-alkylanthraquinone working fluid.

The pretreatment method of 2-pentylanthraquinone working fluid was the same as that of Example C1, except that, the initial sulfur content of the 2-pentylanthraquinone working fluid was 2.0 mg/kg, the adsorbent was the Ni-based amorphous alloy $Ni_{75.4}Fe_{8.0}Cr_{7.3}Al_{9.3}$ prepared from Preparation Example C4, and the conditions of the coupling treatment of alkali washing and adsorption desulfurization comprise: the washing pressure was normal pressure, the washing temperature was 80° C., the rotation speed for stirring was 1000 rpm, based on the weight of the 2-alkylanthraquinone working fluid, the used amount of adsorbent was 10 wt %, the number of washing was 4, and the time for each washing was 4 hours.

The index parameters of the working fluid before and after the pretreatment were shown in Table D.

Example C13

This example illustrated the pretreatment of the 2-alkylanthraquinone working fluid.

The pretreatment method of 2-pentylanthraquinone working fluid was the same as that of Example C2, except that, the concentration of aqueous sodium hydroxide solution used in the coupling treatment of alkali washing and adsorption desulfurization was 20 wt %.

The index parameters of the working fluid before and after the pretreatment were shown in Table D.

Example C14

This example illustrated the pretreatment of the 2-alkylanthraquinone working fluid.

The pretreatment method of 2-pentylanthraquinone working fluid was the same as that of Example C2, except that, the concentration of aqueous sodium hydroxide solution used in the coupling treatment of alkali washing and adsorption desulfurization was 5 wt %.

The index parameters of the working fluid before and after the pretreatment were shown in Table D.

Example C15

This example illustrated the pretreatment of the 2-alkylanthraquinone working fluid.

The pretreatment method of 2-pentylanthraquinone working fluid was the same as that of Example C2, except that, the number of the coupling treatment of alkali washing and adsorption desulfurization was 2, the time for each contacting was 4 hours, and the rotation speed for stirring was 1000 rpm.

The index parameters of the working fluid before and after the pretreatment were shown in Table D.

Example C16

This example illustrated the pretreatment of the 2-alkylanthraquinone working fluid.

The pretreatment method of 2-pentylanthraquinone working fluid was the same as that of Example C2, except that, the condition of acid washing comprised: the washing temperature was 40° C., the rotation speed for stirring was 1000 rpm, the number of washing was 2, and the time for each washing was 4 hours.

The index parameters of the working fluid before and after the pretreatment were shown in Table D.

Example C17

This example illustrated the pretreatment of the 2-alkylanthraquinone working fluid.

The pretreatment method of 2-pentylanthraquinone working fluid was the same as that of Example C1, except that, the adsorbent was the Ni-based amorphous alloy $Ni_{74.8}Co_{7.7}Cr_{9.3}Al_{8.2}$ prepared from Preparation Example C5, based on the weight of the 2-alkylanthraquinone working fluid, the used amount of adsorbent was 5 wt %, and other conditions were not changed.

The index parameters of the working fluid before and after the pretreatment were shown in Table D.

Example C18

This example illustrated the pretreatment of the 2-alkylanthraquinone working fluid.

The pretreatment method of 2-pentylanthraquinone working fluid was the same as that of Example C1, except that, the adsorbent was the Ni-based amorphous alloy $Ni_{82.6}Cu_{3.7}Cr_{6.2}Al_{7.5}$ prepared from Preparation Example C6, based on the weight of the 2-alkylanthraquinone working fluid, the used amount of adsorbent was 5 wt %, and other conditions were not changed.

The index parameters of the working fluid before and after the pretreatment were shown in Table D.

Example C19

This example illustrated the pretreatment of the 2-alkylanthraquinone working fluid.

The pretreatment method of 2-pentylanthraquinone working fluid was the same as that of Example C1, except that the adsorbent was the Ni-based amorphous alloy $Ni_{79}Mo_{5.3}Cr_7Al_{8.7}$ prepared from Preparation Example C7, based on the weight of the 2-alkylanthraquinone working fluid, the used amount of adsorbent was 5 wt %, and other conditions were not changed.

The index parameters of the working fluid before and after the pretreatment were shown in Table D.

Example C20

This example illustrated the pretreatment of the 2-alkylanthraquinone working fluid.

The pretreatment method of 2-pentylanthraquinone working fluid was the same as that of Example C1, except that, the conditions of the coupling treatment of alkali washing and adsorption desulfurization comprise: the concentration of aqueous sodium hydroxide solution was 10 wt %, the temperature was 150° C., the pressure was 1.5 MPa, the rotation speed for stirring was 1000 rpm, based on the weight of the 2-alkylanthraquinone working fluid, the used amount of adsorbent was 10 wt %, the number of washing was 4, and the time for each washing was 4 hours.

The index parameters of the working fluid before and after the pretreatment were shown in Table D.

TABLE D

| Example C # | $C_0$/(mg/kg) | $C_1$/(mg/kg) | μ, % | $W_0$, wt % | $W_1$, wt % |
|---|---|---|---|---|---|
| Example C1 | 2.50 | <0.20 | >92.00 | 0.62 | 0.08 |
| Example C2 | 2.50 | <0.20 | >92.00 | 0.62 | 0.08 |
| Example C3 | 2.50 | 1.45 | 42.00 | 0.62 | 0.09 |
| Example C4 | 2.50 | 0.29 | 88.40 | 0.62 | 0.08 |
| Example C5 | 2.50 | 0.33 | 86.80 | 0.62 | 0.08 |
| Example C6 | 2.50 | 1.53 | 38.80 | 0.62 | 0.08 |
| Example C7 | 2.50 | <0.20 | >92.00 | 0.62 | 0.08 |
| Example C8 | 2.50 | 0.31 | 87.60 | 0.62 | 0.08 |
| Example C9 | 2.50 | 0.39 | 84.40 | 0.62 | 0.08 |
| Example C10 | 6.00 | <0.20 | >96.67 | 1.49 | 0.08 |
| Example C11 | 1.00 | <0.20 | >80.00 | 0.25 | 0.08 |
| Example C12 | 2.00 | <0.20 | >90.00 | 0.50 | 0.08 |
| Example C13 | 2.50 | <0.20 | >92.00 | 0.62 | 0.08 |
| Example C14 | 2.50 | <0.20 | >92.00 | 0.62 | 0.11 |
| Example C15 | 2.50 | <0.20 | >92.00 | 0.62 | 0.12 |
| Example C16 | 2.50 | <0.20 | >92.00 | 0.62 | 0.08 |
| Example C17 | 2.5 | 0.39 | 84.40 | 0.62 | 0.08 |
| Example C18 | 2.5 | 0.30 | 88.00 | 0.62 | 0.08 |
| Example C19 | 2.5 | 0.37 | 85.20 | 0.62 | 0.08 |
| Example C20 | 2.5 | <0.20 | >92.00 | 0.62 | 0.08 |

Note:
$C_0$: sulfur content of the working fluid before adsorption; $C_1$: sulfur content of the working fluid after adsorption; it: desulfurization rate, $\mu = (C_0 - C_1)/C_0$; $W_0$: impurity content in the working fluid before washing; $W_1$: impurity content in the working fluid after washing.

Comparative Example C1

This comparative example illustrated the effect of pretreatment of the 2-alkylanthraquinone working fluid on the activity of palladium catalyst.

Hydrogen peroxide was prepared according to the method of Example C1 by using the 2-alkylanthraquinone working fluid, except that the fresh-formulated 2-alkylanthraquinone working fluid was used directly in the production of hydrogen peroxide without the pretreatment. The experimental results were shown in Table E.

Comparative Example C2

This comparative example illustrated the effect of pretreatment of the 2-alkylanthraquinone working fluid on the activity of palladium catalyst.

Hydrogen peroxide was prepared according to the method of Example C1 by using the 2-alkylanthraquinone working fluid, except that in step of the coupling treatment of alkali washing and adsorption desulfurization, the fresh-formulated 2-alkylanthraquinone working fluid was mixed only with the alkali liquor to perform the alkali washing without the adsorption desulfurization, and then the pretreatment of acid washing and water washing according to the method of Example C1 was performed for the production of hydrogen peroxide. The experimental results were shown in Table E.

Comparative Example C3

This comparative example illustrated the effect of pretreatment of the 2-alkylanthraquinone working fluid on the activity of palladium catalyst.

Hydrogen peroxide was prepared according to the method of Example C1 by using the 2-alkylanthraquinone working fluid, except that in step of the coupling treatment of alkali washing and adsorption desulfurization, the fresh-formulated 2-alkylanthraquinone working fluid was mixed only with the adsorbent to directly perform the pretreatment of adsorption desulfurization, without the washing pretreatment including alkali washing, acid washing and water washing, for the production of hydrogen peroxide. The experimental results were shown in Table E.

TABLE E

| Example # | Service life of palladium catalyst, hours |
|---|---|
| Example C1 | 1600 |
| Comparative Example C1 | 350 |
| Comparative Example C2 | 645 |
| Comparative Example C3 | 960 |

It can be seen from the results in Tables D and E that the pretreatment method of the 2-alkylanthraquinone working fluid provided by the invention can remarkably reduce the content of impurity and the content of sulfur in the working fluid, and can prolong the service life of the catalyst if used in the production of hydrogen peroxide to ensure that the catalyst has higher activity and stability, so that the problem of poisoning and inactivation of the noble metal palladium catalyst in the hydrogenation of the working fluid can be effectively solved, and the method has good industrial application prospect.

The preferred embodiments of the present invention have been described above in detail, but the present invention is not limited thereto. Within the scope of the technical concept of the present invention, a variety of simple modifications can be made to the technical solution of the present invention, including the combination of various technical features in any other suitable manner. These simple modifications and combinations thereof should also be regarded as the disclosure of the present invention, all belonging to the protection scope of the present invention.

The invention claimed is:

1. A method of preparing a 2-alkylanthracene, comprising:
    carrying out an alkylation reaction of anthracene with an alkylation reagent under an alkylation condition and in the presence of an alkylation reaction solvent and a catalyst;
    obtaining a reaction product comprising anthracene and a plurality of alkylanthracenes,
    wherein the plurality of alkylanthracenes comprise 2-alkylanthracene; and
    separating 2-alkylanthracene from the reaction product,
    wherein the separation comprises separating anthracene by melting crystallization and separating 2-alkylanthracene by distillation, and
    the alkyl in the 2-alkylanthrance is one or more selected from $C_4$-$C_7$ alkyls.

2. The method of claim 1, wherein the separation includes:
    (a) heating the reaction product of the anthracene alkylation reaction to a molten state, cooling and crystallizing, separating to obtain an anthracene crystal and a product stream comprising the plurality of alkylanthracenes, heating the anthracene crystal to sweat, and separating a sweating liquor and the anthracene crystal; and
    (b) separating 2-alkylanthracene from the product stream comprising the plurality of alkylanthracenes by one-step distillation or multiple-step distillation.

3. The method of claim 2, wherein in step (a),
    a melting temperature of the reaction product is 200-270° C.;

a temperature for cooling and crystallizing is 180-210° C., and a temperature reduction rate for cooling and crystallizing is 0.1-10° C./h, a time for cooling and crystallizing is 1-5 hours;

a heating rate for sweating the anthracene crystal is 0.1-8° C./h;

and wherein the sweating is terminated prior to the reaction product reaching melting temperature of the anthracene crystal, the amount of the sweating liquor is 5-40% by weight of the anthracene crystal.

4. The method of claim 2, wherein step (a) further comprises adding anthracene crystal seeds to the molten reaction product in an amount of 0.1-10 wt % based on the mass of the molten reaction product.

5. The method of claim 2, further comprising recycling the sweating liquor back to the step of melting crystallization, and carrying out the melting crystallization together with the reaction product containing alkylanthracene.

6. The method of claim 2, wherein in step (b), when a boiling point of 2-alkylanthracene is the lowest or the highest among boiling points of the plurality of alkylanthracenes, performing the one-step distillation separation of 2-alkylanthracene.

7. The method of claim 2, wherein in step (b), when a boiling point of the 2-alkylanthracene is between a highest boiling point and a lowest boiling point of the plurality of alkylanthracenes, performing the multiple-step distillation, wherein the multiple-step distillation comprises:

subjecting the product steam comprising the plurality of alkylanthracenes to a first distillation separation in a first distillation column to produce a first distillate containing light component Cj1-anthracene and a first bottom product containing heavy component Cj2-anthracene; subjecting the first distillate to a second distillation in a second distillation column to produce a second distillate containing light component Cj3-anthracene and a second bottom product containing target product Ci-anthracene, wherein the light component Cj1-anthracene is a mixture comprising a plurality of alkylanthracenes, and for each alkylanthracene, the total carbon number j1 of alkyl side chain is $1 \leq j1 < i+1$; the heavy component Cj2-anthracene is one alkylanthracene or a mixture of a plurality of alkylanthracenes, and for each alkylanthracene, the total carbon number j2 of alkyl side chain is $i < j2 < 41$; the light component Cj3-anthracene is one alkylanthracene or a mixture of a plurality of alkylanthracenes, and for each alkylanthracene, the total carbon number j3 of alkyl side chain is $1 \leq j3 < i$, wherein the first distillation is carried out under conditions in which a top pressure of the first distillation column is 0.01-20 KPa, a bottom temperature at the first distillation column is 180-360° C., a theoretical plate number is 20-90, and a top reflux ratio is 0.5-8, and wherein the second distillation is carried out under conditions in which a top pressure of the second distillation column is 0.01-20 KPa, a bottom temperature at the second distillation column is 180-330° C., a theoretical plate number is 20-90, a top reflux ratio is 0.5-8.

8. The method of claim 2, wherein in step (b), when a boiling point of the 2-alkylanthracene is between a highest boiling point and a lowest boiling point of the plurality of alkylanthracenes, performing the multiple-step distillation, wherein the multiple-step distillation comprises:

subjecting the product stream comprising the plurality of alkylanthracenes to a first distillation in a first distillation column to produce a first distillate containing light component Cm1-anthracene and a first bottom product containing heavy component Cm2-anthracene; and subjecting the second bottom product containing heavy component Cm2-anthracene to a second distillation in a second distillation column to produce a second distillate containing target product Ci-anthracene and a second bottom product containing heavy component Cm3-anthracene, wherein the light component Cm1-anthracene is an alkylanthracene or a mixture of a plurality of alkylanthracenes, and for each alkylanthracene, the total carbon number m1 of alkyl side chain is $1 < m1 < i$, wherein the heavy component Cm2-anthracene is a mixture of a plurality of alkylanthracenes, and for each alkylanthracene, the total carbon number m2 of alkyl side chain is $i-1 < m2 < 41$, wherein the heavy component Cm3-anthracene is one alkylanthracene or a mixture of a plurality of alkylanthracenes, and for each alkylanthracene, the total carbon number m3 of alkyl side chain is $i < m3 < 41$, wherein j1, j2, j3, m1, m2 and m3 are integers, i in the target product Ci-anthracene represents the total carbon number of alkyl side chain, and i=an integer of 4-7, wherein the first distillation is carried out under conditions in which a top pressure of the first distillation column is 0.01-20 KPa, a bottom temperature at the first distillation column is 180-360° C., a theoretical plate number is 20-90, and a top reflux ratio is 0.5-8, and wherein the second distillation is carried out under conditions in which a top pressure of the second distillation column is 0.01-20 KPa, a bottom temperature at the second distillation column is 180-330° C., a theoretical plate number is 20-90, a top reflux ratio is 0.5-8.

9. The method of claim 1, further comprising, prior to the separation step, subjecting a product mixture from the alkylation reaction to distillation in a distillation column to produce a distillate containing the alkylation reaction solvent, and the reaction product comprising anthracene and the plurality of alkylanthracenes from a bottom of the distillation column, wherein a temperature at the bottom of distillation column is 100-300° C., and a pressure at a top of the distillation column is normal pressure.

10. The method of claim 1, wherein the alkylation reagent is one or more selected from alkene, alcohol, halohydrocarbon and ether substances containing 2-8 carbon atoms and a mole ratio of anthracene to the alkylation reagent is 0.2:1-20:1.

11. The method of claim 1, wherein the alkylation reaction is carried out by contacting a feedstock liquor containing anthracene, the catalyst, and the alkylation reaction solvent with the alkylation reagent at a reaction temperature of 100-250° C. and a reaction pressure of 0-1 MPa for 0.01-48 hours.

12. The method of claim 11, wherein the alkylation reaction solvent is a mixture of solvent A having a dielectric constant of 1-10 at 20° C. and solvent B having a dielectric constant of more than 10 to 50 or less at 20° C.;

a volume ratio of the solvent A to the solvent B is 0.01-100, a content of anthracene is 5-60 wt %, based on a total weight of anthracene and the alkylation reaction solvent, the catalyst is a solid acid catalyst comprising an active molecular sieve and a binder, and, based on a total weight of the solid acid catalyst, a content of the active molecular sieve is 30-95 wt %, a content of the binder is 5-70 wt %, the active molecular sieve is one or more selected from X zeolite, Y zeolite, beta zeolite, ZSM-5 zeolite, SAPO zeolite, and mesoporous zeolite, and the binder is a thermotolerant inorganic oxide and/or silicate; and based on a total weight of the feedstock liquor, a content of the catalyst is 0.01-50 wt %.

13. The method of claim 11, wherein the alkylation reaction solvent is a solvent having a dielectric constant of 1-10 at 20° C.;

based on a total weight of anthracene and alkylation reaction solvent, a content of anthracene is 5-60 wt %;

the catalyst is one or more of liquid acids; and based on a total weight of the feedstock liquor containing anthracene, the catalyst and the alkylation reaction solvent, the content of catalyst is 0.01-50 wt %.

14. A method for preparing 2-alkylanthraquinone, comprising:

preparing a 2-alkylanthracene according to the method of claim 1;

contacting the 2-alkylanthracene with an oxidizing agent under an oxidizing condition and in the presence of an oxidation reaction solvent and a catalyst to perform an oxidation reaction.

15. The method according to claim 14, wherein the solvent for the oxidation reaction is a solvent with a dielectric constant of more than 2.8 at 20° C., and based on the total weight of 2-alkylanthracene and the oxidation reaction solvent, the total content of 2-alkylanthracene is 0.1-80 wt %.

16. The method according to claim 14, wherein the oxidation reaction solvent is:

(1) solvent A having a dielectric constant of 1-10 at 20° C., or (2) a combination of solvent A having a dielectric constant of 1-10 at 20° C. and solvent B having a dielectric constant of more than 10 to 50 or less at 20° C., the volume ratio of solvent A to solvent B being 0.01-100;

wherein, based on the total weight of 2-alkylanthracene and the oxidation reaction solvent, the total content of 2-alkylanthracene is 0.1-80 wt %.

17. The method for preparing 2-alkylanthraquinone according to claim 14, wherein, according to a first set of conditions:

the oxidizing agent is hydrogen peroxide;

the catalyst is one or more of alkaline earth metal oxide, alkaline earth metal hydroxide, oxygen-containing compound of transition metal and oxygen-containing compound of lanthanide series metal;

the condition of oxidation reaction includes: the reaction temperature is 10-200° C.;

the reaction pressure is 0-1 MPa;

the reaction time is 0.01-48 hours;

the mole ratio of the oxidizing agent to 2-alkylanthracene is 0.01:1-100:1; and the mole ratio of the oxidizing agent to the catalyst is 0.01:1-100:1, or according to a second set of conditions:

the oxidizing agent is tert-butyl hydroperoxide;

the catalyst contains a support and an active component on the support;

the content of the active component is 0.01-40 wt %, based on the weight of the support in the catalyst and based on the element content;

the active component is one or more of elements under the group VA and transition metals;

based on the element content, the mass ratio of the transition metal to the element under the group VA is 1-20:1;

the support is a thermotolerant inorganic oxide;

the oxidation reaction solvent is one or more of $C_6$-$C_{12}$ alkane, cycloalkane and aromatic hydrocarbon, wherein, the aromatic hydrocarbon is substituted or unsubstituted benzenes, the substituent is one or more of $C_1$-$C_4$ alkyl and halogen;

the condition of oxidation reaction includes: the reaction temperature is 10-150° C.; the reaction pressure is 0-1 MPa; the reaction time is 0.01-48 hours;

the content of catalyst is 0.01-50 wt %, based on the total weight of catalyst and oxidation reaction solvent;

the mole ratio of the oxidizing agent to 2-alkylanthracene is 0.01:1-100:1; and the total content of 2-alkylanthracene is 0.1-80 wt %, based on the total weight of 2-alkylanthracene and the oxidation reaction solvent.

18. The method according to claim 17, wherein, according to the second set of conditions, the catalyst is obtained by the following preparation method: impregnating a support with a solution containing a soluble compound of active component, drying and calcining the impregnated support;

the impregnation temperature is 0-100° C.;

the impregnation time is 4-24 hours;

the drying temperature is 90-125° C., the drying time is 1-12 hours;

the calcining temperature is 300-700° C., the calcining time is 2-6 hours;

the support and the soluble compound of active component are used in such an amount that based on the weight of the support in the catalyst, the content of the active component as element is 0.01-40 wt %;

the soluble compound of active component is soluble compound(s) of one or more of elements under the group VA and transition metals;

the soluble compound of active component is used in such an amount that as element(s), in the catalyst, the mass ratio of the transition metal to the element under the group VA is 1-20:1;

the support is a thermotolerant inorganic oxide; or the thermotolerant inorganic oxide is one or more of silicon dioxide, magnesium oxide and silica-alumina composite oxide, in the silica-alumina composite oxide, as oxide, the content of $SiO_2$ is 0.01-70 wt %, the content of $Al_2O_3$ is 30-99.9 wt %.

19. A method for preparing hydrogen peroxide, comprising:

mixing the 2-alkylanthraquinone prepared according to the method of claim 14 with a mixed solvent comprising a nonpolar solvent and a polar solvent to obtain a 2-alkylanthraquinone working fluid;

subjecting the 2-alkylanthraquinone working fluid to hydrogenation, oxidation and extraction, characterized in that, prior to the hydrogenation, the 2-alkylanthraquinone working fluid is subjected to a pretreatment, wherein the pretreatment comprises: contacting the 2-alkylanthraquinone working fluid with an adsorbent in an alkali liquor to perform an adsorption desulfurization and impurity removal, and washing the 2-alkylanthraquinone working fluid that has been subjected to the adsorption desulfurization and impurity removal, and wherein the adsorbent is an amorphous alloy containing nickel, based on the total weight of amorphous alloy, the content of nickel is 35-95 wt %.

20. The method according to claim 19, wherein based on the total weight of amorphous alloy, the content of nickel is 35-95 wt %, and the total content of other metals is 5-65 wt %.

21. The method according to claim 19, wherein the amorphous alloy contains nickel and aluminum, and one or more metals selected from iron, chromium, copper, zinc, molybdenum, and cobalt; and based on the total weight of amorphous alloy, the content of nickel is 35-95 wt %, the content of aluminum is 0.5-40 wt %, and the total content of one or more metals of iron, chromium, copper, zinc, molybdenum and cobalt is 0.1-50 wt %.

22. The method according to claim 19, wherein, in the X-ray diffraction pattern of the adsorbent, a diffuse peak appears at 45±1° in the 2θ angle range of 20-80°.

23. The method according to claim 19, wherein the condition for contacting the 2-alkylanthraquinone working fluid with the adsorbent in the alkali liquor comprises:

the temperature is 10-200° C., the pressure is 0-3 MPa;

the number of contact is 1-5, and the time for each contact is 0.01-24 hours;

the contact is performed under stirring, and the rotation speed of the stirring is 500-2000 rpm;

the used amount of the adsorbent is 0.01-40 wt %, based on the weight of the 2-alkylanthraquinone working fluid, the alkali in the alkali liquor is an inorganic base, the inorganic base is at least one of sodium hydroxide, potassium hydroxide, sodium carbonate and potassium carbonate; or the volume ratio of the alkali liquor to the 2-alkylanthraquinone working fluid is 0.1-10.

24. The method according to claim 19, wherein the washing condition is such one that the pH value of the washed 2-alkylanthraquinone working fluid is neutral, and the washing comprises acid washing using an inorganic acid and water washing in sequence, the inorganic acid being selected from at least one of sulfuric acid, hydrochloric acid, nitric acid, and phosphoric acid, and the acid is used in the form of acid liquor;

the condition for acid washing comprises:

the temperature is 5-100° C., the pressure is 0-1 MPa;

the volume ratio of the acid liquor to the 2-alkylanthraquinone working fluid is 0.1-10; and the number of acid washing is 1-5, and the time for each acid washing is 0.01-24 hours;

the acid washing is performed under stirring, and the rotation speed of the stirring is 500-2000 rpm, or the condition for water washing comprises: the pressure is 0-1 MPa; the temperature is 5-100° C.; the volume ratio of water to the 2-alkylanthraquinone working fluid is 0.1-10;

the number of water washing is 1-5, and the time for each water washing is 0.01-24 hours; and the water washing is performed under stirring, and the rotation speed of the stirring is 500-2000 rpm.

* * * * *